(12) United States Patent
Juge et al.

(10) Patent No.: US 9,242,925 B2
(45) Date of Patent: Jan. 26, 2016

(54) VERSATILE AND STEREOSPECIFIC SYNTHESIS OF γ,δ-UNSATURATED AMINO ACIDS BY WITTIG REACTION

(75) Inventors: Sylvain Juge, Dijon (FR); Jerome Bayardon, Dijon (FR); Emmanuelle Remond, Mailleroncourt-Charette (FR); Marie-Joelle Ondel-Eymin, Arc sur Tille (FR)

(73) Assignees: CENTRE NATIONAL DE LA RECHERCHE SCIENTIFIQUE (CNRS), Paris (FR); UNIVERSITE DE BOURGOGNE, Dijon (FR)

( * ) Notice: Subject to any disclaimer, the term of this patent is extended or adjusted under 35 U.S.C. 154(b) by 43 days.

(21) Appl. No.: 14/241,561

(22) PCT Filed: Aug. 28, 2012

(86) PCT No.: PCT/EP2012/066686
§ 371 (c)(1),
(2), (4) Date: Feb. 27, 2014

(87) PCT Pub. No.: WO2013/030193
PCT Pub. Date: Mar. 7, 2013

(65) Prior Publication Data
US 2014/0364339 A1    Dec. 11, 2014

Related U.S. Application Data

(60) Provisional application No. 61/528,376, filed on Aug. 29, 2011.

(30) Foreign Application Priority Data

Oct. 10, 2011    (FR) ...................... 11 59112

(51) Int. Cl.
| | |
|---|---|
| C07C 229/22 | (2006.01) |
| C07C 271/22 | (2006.01) |
| C07F 9/54 | (2006.01) |
| C07F 17/02 | (2006.01) |
| C07D 307/54 | (2006.01) |
| C40B 40/04 | (2006.01) |
| C07F 5/02 | (2006.01) |
| C07C 227/02 | (2006.01) |

(52) U.S. Cl.
CPC ............. C07C 229/22 (2013.01); C07C 227/02 (2013.01); C07C 271/22 (2013.01); C07D 307/54 (2013.01); C07F 5/027 (2013.01); C07F 9/5435 (2013.01); C07F 9/5442 (2013.01); C07F 17/02 (2013.01); C40B 40/04 (2013.01); C07B 2200/07 (2013.01)

(58) Field of Classification Search
CPC .................................................. C07C 229/22
USPC ........................................... 549/505; 506/15
See application file for complete search history.

(56) References Cited

FOREIGN PATENT DOCUMENTS

WO    WO 2010/068371    *    6/2010

OTHER PUBLICATIONS

Beaulieu et al., Biorg. Med. Chem. Lets (2010), vol. 20(24), pp. 7444-7449.*
Lin et al., e-ROS Encyclop. of Reagents for Org. Synthes. (2007), John Wiley & Sons, Ltd. Chichester UK.*
Denmark et al., e-ROS Encyclop. of Reagents for Org. Synthes. (2007), John Wiley & Sons, Ltd. Chichester UK.*
Clerici et al., "5-(4H)-oxazolones. Part VIII. An efficient synthesis of Δ1-pyrroline-2-carboxylic acid derivatives through Mickael and Wittig condensation", Tetrahedron, vol. 51, No. 36, 1995, pp. 9985-9994.
Moussaoui et al., "Anionic activation of the Wittig reaction using a solid-liquid phase transfer: examination of the medium-, temperature-, base- and phase-transfer catalyst effects", Arkivoc, Jun. 2006, pp. 1-22.

(Continued)

Primary Examiner — Taofiq A Solola
(74) Attorney, Agent, or Firm — Young & Thompson

(57) ABSTRACT

The γ,δ-unsaturated α-amino acids of general formula (I). Also, a versatile process for the stereospecific synthesis of said compounds of formula (I), involving a Wittig reaction. Further, intermediate products of general formulae (II) and (III), as shown below, which are involved in the synthesis of compounds (I).

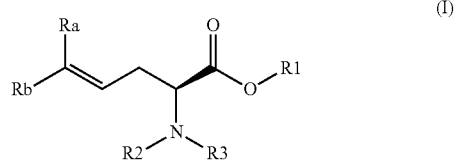

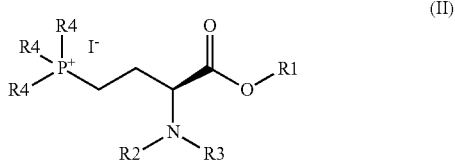

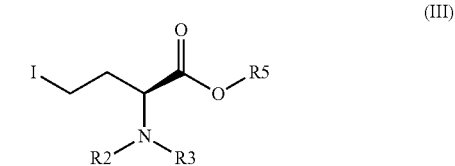

Compounds of general formula (I) may be useful as therapeutic substances, or as reagents or intermediates for fine chemistry.

15 Claims, No Drawings

(56) References Cited

OTHER PUBLICATIONS

Malachowski et al., "The chemistry of phosphapeptides: investigations on the synthesis of phosphonamidate, phosphonate and phosphinate analogues of glutamyl-, gamma- glutamate", the Journal of Organic Chemistry, vol. 59, No. 25, Dec. 1, 1994, pp. 7625-7634.

Kennedy et al., "Progress towards the synthesis of piperazimycin A: synthesis of the non-protenogenic amino acids and elaboration into dipeptides", Tetrahedron Letters, vol. 51, No. 18, May 5, 2010, pp. 2493-2496.

Meyer et al., "Triphenylphosphonium salts bearing an L-alanyl substituent: short synthesis and enantiomeric analysis by NMR", Tetrahedron Letters, vol. 42, No. 24, Jun. 11, 2001, pp. 3981-3984.

Sibi et al., "A new nucleophilic alaninol synthon from serine", Tetrahedron Letters, vol. 31, No. 51, Jan. 1, 1990, pp. 7407-7410.

Itaya et al., "Synthesis of (S)-(-)-wybutine, the fluorescent minor base from yeast phenylalanine transfer ribonucleic acids", Tetrahedron Letters, vol. 26, No. 3, Jan. 1, 1985, pp. 347-350.

Itaya et al., "Synthesis and absolute configuration of wybutine, the fluorescent minor base from phenylalanine transfer ribonucleic acids", Chemical & Pharmaceutical Bulletin, vol. 39, No. 6, Jan. 1, 1991, pp. 1407-1414.

Kokotos et al., "A general approach to the asymmetric synthesis of unsaturated lipidic [alpha]-amino acids. The First synthesis of [alpha]-aminoarachidonic acid", the Journal of Organic Chemistry, vol. 63, No. 11, May 1, 1998, pp. 3741-3744.

Doyle et al., "Highly effective catalytic methods for ylide generation from diazo compounds. Mechanism of the rhodium- and copper-catalyzed reactions with allylic compounds", the Journal of Organic Chemistry, vol. 46, No. 25, Dec. 1, 1981, pp. 5094-5102.

Elaridi et al., "Controlled synthesis of (S,S)-2,7-diaminosuberic acid: a method for regioselective construction of dicarba analogues of multicystine-containing peptides", the Journal of Organic Chemistry, vol. 71, No. 20, Sep. 1, 2006, pp. 7538-7545.

Otani et al., "Effect of acylated amino acids and acylated amino acid analogs on microbial antitumor screen", Journal of Pharmaceutical Sciences, American Pharmaceutical Association, Washington, vol. 67, No. 4, Apr. 1, 1978, pp. 520-526.

Noguchi et al., "The isolation and identification of nicotianine: a new amino acid from tobacco leaves", Phytochemistry, Pergamon Press, vol. 7, No. 10, Oct. 1968, pp. 1861-1866.

Sibi et al., "Investigations of a nucleophilic alaninol synthon derived from serine", J. Am. Chem. Soc., vol. 121, Feb. 1999, pp. 7509-7516.

Baldwin et al., "Nucleophilic ring opening of aziridine-2-carboxylates with Wittiog reagents: an enantioefficient synthesis of unsaturated amino acids", J. Chem. Soc., Chem. Comm., 1987, pp. 153-155.

Baldwin et al., "Amino acid synthesis via ring opening of N-sulphonyl aziridine-2-carboxylate esters with organometallic reagents", Tetrahedron, vol. 49, No. 28, 1993, pp. 6309-6330.

Guibé, Francois, "Allylic protecting groups and their use in a complex environment. Part II: Allylic Protecting Groups and Their Removal through Catalytic Palladium π-Allyl Methodology", Tetrahedron report No. 444, vol. 54, 1998, pp. 2967-3042.

Vazquez et al., "Photophysics and biological applications of the environment sensitive fluorophore 6-N,N-dimethylamino-2,3-naphthalimide", J. Am. Chem. Soc., vol. 127, 2005, pp. 1300-1306.

Hebbe et al., "NMR enantiodifferentiation of triphenylphosphonium salts by chiral hexacoordinated phosphate anions", Tetrahedron Letters, vol. 44, 2003, pp. 2467-2471.

Brown et al., "Matrix metalloproteinase inhibitors containing a (carboxyalkyl)amino zinc ligand: modification of the P1 and P2' residues", J. Med. Chem., vol. 37, No. 5, Jul. 1994, pp. 674-688.

Ramalingam et al., "Synthesis of stereospecific deuterium-labeled homoserines and homoserine lactones", J. Org. Chem., vol. 53, No. 9, 1988, pp. 1900-1903.

Stein et al., "Enzyme-catalyzed regioselective hydrolysis of aspartate diesters", J. Org. Chem., vol. 60, No. 24, 1995, pp. 8110-8112.

Adamczyk et al., "A concise synthesis of (S)-(-)-3-(2-carboxy-4-pyrrolyl)-alanine", Tetrahedron: Asymmetry, vol. 11, Jun. 2000, pp. 3063-3068.

Werner et al., "The C-glycosyl analog of an N-linked glycoamino acid", Tetrahedron Letters, Sep. 1998, vol. 39, pp. 9135-9138.

Fowler et al., "A one-pot reductive amination/6-endo-trig cyclisation for the stereoselective synthesis of 6-substituted-4-oxopipecolic acids", Chem. Commun., vol. 47, Apr. 2011, pp. 6569-6571.

Fowler et al., "Synthesis of fluorescent enone derived alpha-amino acids", Org. Biomol. Chem., vol. 7, Jul. 2009, pp. 4309-4316.

International Search Report, dated Oct. 12, 2012, from corresponding PCT application, PCT/EP2012/066686.

Padron et al., "Enantiospecific synthesis of alpha-amino acid semialdehydes: a key step for the synthesis of unnatural unsaturated and saturated alpha-amino acids", Tetrahedron: Asymmetry 9, Sep. 1998, pp. 3381-3394, Elsevier Science.

\* cited by examiner

VERSATILE AND STEREOSPECIFIC SYNTHESIS OF γ,δ-UNSATURATED AMINO ACIDS BY WITTIG REACTION

FIELD OF INVENTION

The present invention relates to γ,δ-unsaturated α-amino acids of general formula (I). The present invention also provides a versatile process for the stereospecific synthesis of said compounds of formula (I), involving a Wittig reaction. The present invention also relates to intermediate products of general formulae (II) and (III), as shown below, which are involved in the synthesis of compounds (I).

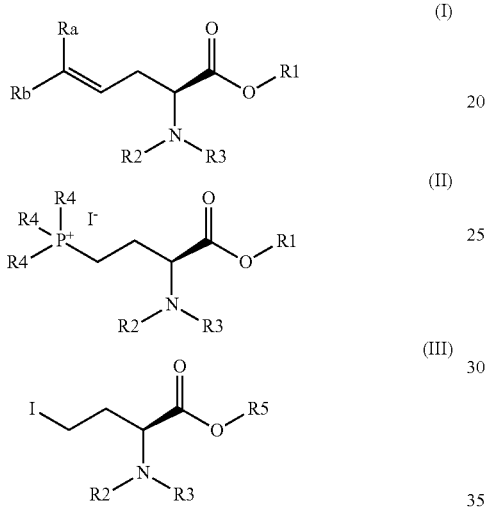

wherein
- R1 represents a hydrogen atom or R5, wherein R5 is a substituted or unsubstituted group selected from alkyl, cycloalkyl, aryl and alkenyl;
- R2 and R3 may be the same or different and represent each a hydrogen atom or a substituted or unsubstituted group selected from alkyl, cycloalkyl, aryl, alkenyl and —COR, wherein R is a substituted or unsubstituted group selected from alkyl, cycloalkyl, aryl, alkenyl, alkyloxy, cycloalkyloxy and aryloxy;
- R4 represent a substituted or unsubstituted group selected from alkyl, cycloalkyl, aryl and alkenyl;
- Ra and Rb may be the same or different and represent each a hydrogen atom or a substituted or unsubstituted group selected from alkyl, alkenyl, cycloalkyl, aryl, metallocenyl and —COR, wherein R is a substituted or unsubstituted group selected from alkyl, cycloalkyl, aryl, alkenyl, alkyloxy, cycloalkyloxy and aryloxy.

Compounds of general formula (I) may useful as therapeutic substances, or as reagents or intermediates for fine chemistry.

BACKGROUND OF INVENTION

α-amino acids present an important biological interest, because they constitute peptides and proteins. As they play an important role in the organism, the chemist seeks to synthesize structural analogous, in order to obtain new biological properties or modified peptides. The use of non-natural amino acids allow for example to conduct studies of metabolism and of enzymatic cycles. Non-natural amino acids are also implied in the development of new drugs.

Among different strategies to develop analogous of natural amino acids, it is possible to introduce an unsaturation on the lateral chain. The unsaturation may be more or less distant from the alpha carbon. In the present invention, the Applicant has focused his interest on γ,δ-unsaturated α-amino acids.

The introduction of an unsaturation into amino acids implies structural modifications that can induce new biological properties. Especially, peptide chains comprising an unsaturated amino acid present a rigid secondary structure with a β-turn configuration. Such a structure is interesting to develop new drugs or to improve the fixation of bioactive molecules. Consequently, unsaturated amino acids are important for the synthesis of modified peptides, useful in biology or in medicinal chemistry. Unsaturated amino acids may also be used to develop new markers useful in medical imaging or for diagnosis.

For example, β,γ-unsaturated α-amino acids such as trans-3,4-dehydroarginine or rhizobitoxine have been shown to be enzyme inhibitors.

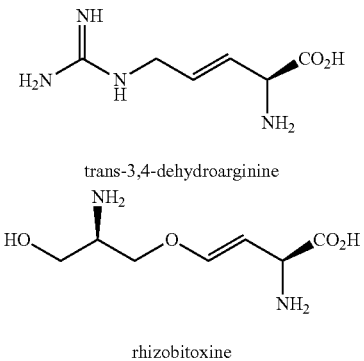

trans-3,4-dehydroarginine rhizobitoxine

Unsaturated amino acids have also been used for the preparation of antibiotics, such as Phomopsin (A), which is a hexapeptide constituted by two fragments. Fragment A is a cyclodedihydrotripeptide constituted only by non-classical amino acids whose β,γ-unsaturated L-Valine, and fragment B, which is a linear didehydrotripeptide with exocyclic framework.

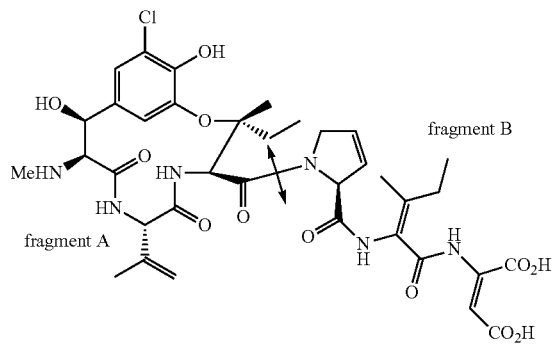

Phomopsin (A)

Unsaturated amino acids may also have applications for the preparation of peptide derivatives useful as sweeteners, in polyamide materials, in nanomaterials, as surfactants or as phytosanitary products.

Amino acids bearing an unsaturation on the lateral chain are also used in organic synthesis, in particular in Diels-Alder reactions, in cyclo-additions or in catalytic reactions (hydroformylation, metathesis, Heck coupling, Suzuki-Miyaura coupling). Especially, metathesis reactions on unsaturated amino acids may be used to obtain higher unsaturated homologues.

Unsaturated amino acids may also be used in total synthesis of products of biological interest, as it is the case in the synthesis of Nothapodytine B, a compound useful as antiviral drug, or in the case of the synthesis of the α-amino-arachidonic acid, a fatty acid.

Moreover, unsaturated amino acids may be functionalized by transition metals and resulting complexes may be used as contrast agents for medicinal imaging, as therapeutic agents, as synthesis intermediates or as chiral catalysts.

The presence of a double bond on the lateral chain of amino acid offers the possibility to further functionalize the molecule with a wide variety of chemical groups, such as aryl, alkyl, calixarenyl, azido or boronato groups, and therefore to obtain numerous compounds useful in high throughput synthesis.

Among the syntheses of unsaturated amino acids described in the literature, allylation of Shiff base with creation of $C_\alpha$-$C_\beta$ carbon bonds, catalyzed by palladium complex or under phase transfer conditions, is one of the methods the most used to access to such compounds (Scheme 1). This strategy allows the highly stereoselective synthesis of allylglycine derivatives, in the presence of an organocatalyst such as the ammonium salt depicted in Scheme 1. However, this method applies only to some allylic groups and it is mainly the Shiff base with a t-butyl ester that is employed. Therefore, this method is not versatile. Moreover, reactants and catalysts used in this method are expensive or difficult to prepare.

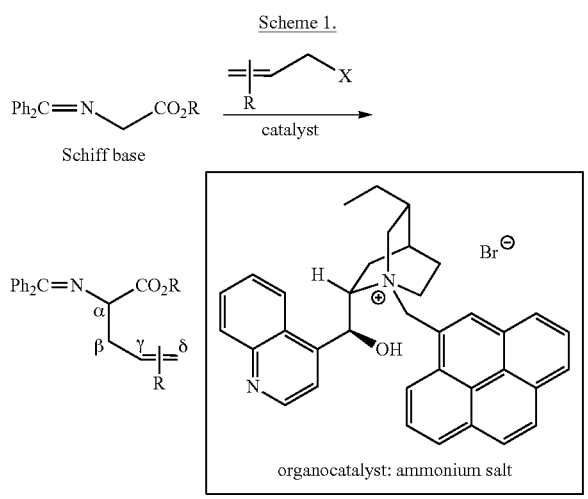

Other routes of synthesis of unsaturated amino acids are available, such as Mitsunobu reactions with hydroxyacid derivatives, beta-elimination reactions, the use of cuprozincic derivatives of serine or Strecker reaction. However, the syntheses require numerous steps with uncertain yields and unguaranteed stereoselectivities. Especially, these methods are often associated with loss of reagents and are dedicated to the synthesis of a single compound. Therefore, these methods are not adapted to the synthesis of series of compounds. In the case of cuprozincic derivatives of serine, the use of cuprozincic products is difficult, depends of the substrats and requires expertise in the manipulation of such reagents.

The synthesis of γ,δ-unsaturated amino acids has also been envisaged by Wittig reaction. However, up to now, few examples of Wittig reaction involving amino acid moiety were described. Indeed, the basic conditions of reaction cause racemization and are incompatible with the polyfunctionality of an amino acid, even protected.

One example of synthesis of unsaturated amino acids through a Wittig reaction involves aldehydes derived from aspartic or glutamic acid (Kokotos G., Padron J. M., Martin T., Gibbons W. A. and Martin V. S., *J. Org. Chem.*, 1998, 63, 3741-3744).

In this synthesis, represented in scheme 2, a Wittig reaction between a phosphonium ylide and the aldehyde derived from glutamic acid affords, after deprotection of acid and amine functions, the enantiomerically pure α-amino-arachidonic acid in 88% yield.

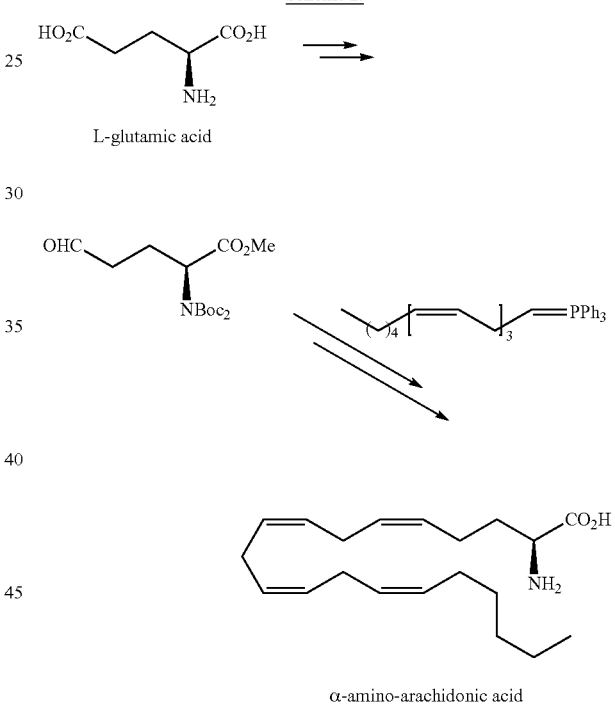

Starting from aspartic acid instead of glutamic acid, this method may lead to γ,β-unsaturated amino acids. However, this strategy presents the inconvenient not to be versatile. Indeed, the introduction of different moieties after the double bond on the lateral chain of the amino acid requires the synthesis of each corresponding phosphonium salts. Therefore, this method is not adapted to synthesize a wide variety of unsaturated amino acid for high throughput synthesis.

An alternative method involving a Wittig reaction was proposed in a pioneering work of Itaya depicted in scheme 3 (Itaya T. and Mizutani A., *Tetrahedron Lett.*, 1985, 26(3), 347-350). In this example, a phosphonium chloride was prepared in seven steps starting from L-serine. The phosphonium chloride was then reacted with an aldehyde, affording the corresponding β,γ-unsaturated amino acid with a yield of 5%, in a stereoselective manner.

Scheme 3.

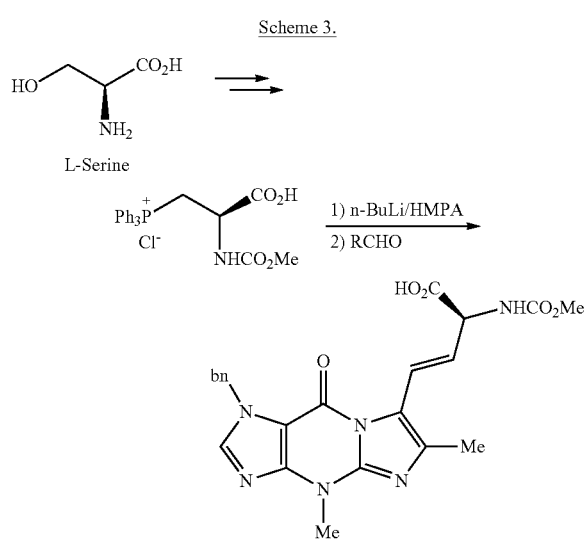

In further work on the synthesis of this particular unsaturated amino acid implied in the synthesis of Wybutine, Itaya improved the yield of the Wittig reaction to modest yields (<30%) by some optimizations of the conditions (Itaya T, Mizutani A. and Lida T., *Chem. Pharm. Bull.*, 1991, 39(6), 1407-1414).

Therefore the method developed by Itaya does not allow obtaining satisfying yields, as required in high throughput synthesis. Moreover, conditions used by Itaya are drastic and the reaction is performed in presence of HMPT, a solvent suspected to be mutagen.

Alternatives to Itaya method were proposed by Sibi and by Baldwin to use a Wittig reaction in the synthesis of unsaturated amino acids, starting from a phosphonium salt derivative of amino acid.

The method developed by Sibi consists in protecting the carboxylic acid function of the amino acid by reduction in alcohol, in order to avoid the deprotonation of the ester in the basic conditions of the Wittig reaction (scheme 4) (Sibi M. P. and Renhowe P. A., *Tetahedron Lett.*, 1990, 31(51), 7407-7410; Sibi M. P., Rutherford D., Renhowe P. A. and Li B., *J. Am. Chem. Soc.*, 1999, 121, 7509-7516). The L-serine is first protected into an oxazolidinone derivative with phosgene. The intermediate is then transformed into iodo-derivative after reduction, and finally in the phosphonium salt represented on scheme 4. After deprotonation of the phosphonium salt, the ylide reacts with aldehydes to afford the unsaturated derivatives which are then hydrolyzed into amino alcool. The β,γ-unsaturated amino acid is finally obtained after oxidation by pyridinium dichromate (PDC).

Scheme 4.

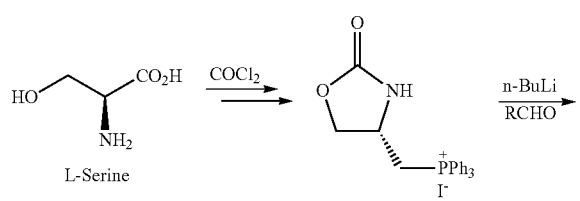

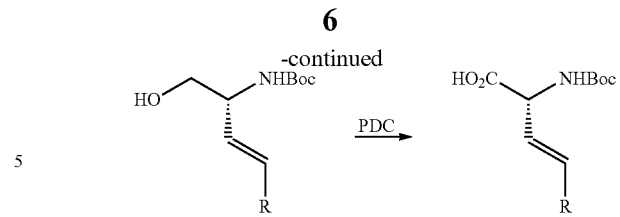

The inconvenient of the method developed by Sibi lies in the fact of using phosgene and a chrome oxidizing agent. On the other hand, this reaction leads to unsaturated amino acids with the inverse absolute configuration D. Consequently, the synthesis of unsaturated L-amino acids requires using D-serine which is very expensive.

The method of Baldwin to synthesize γ,β-unsaturated amino acids by Wittig reaction consists in reacting an aziridine derived from L-serine, successively with a stabilized ylide and with an aldehyde (Scheme 5) (Baldwin J. E., Adlington R. M. and Robinson N. G., *JCS Chem. Corn.*, 1987, 153-155; Baldwin J. E., Spivey A. C., Schofield C. J. and Sweeney J. B., *Tetrahedron*, 1993, 43, 6309-6330).

Scheme 5.

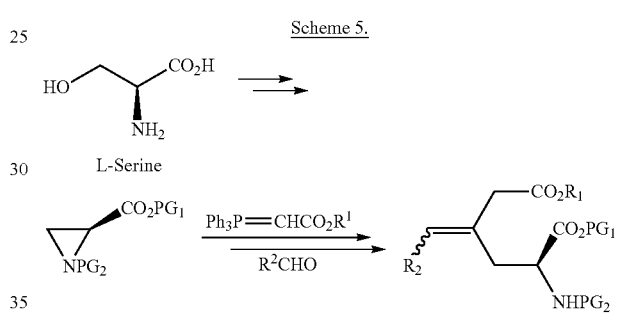

One inconvenient of the synthesis developed by Baldwin lies in the fact that the adequately protected aziridine should first be synthesized. This preliminary step is not easy, all the more that the aziridine is not very stable. Moreover, the reaction implying an ylide stabilized by an ester function is not very general and lead to moderate yields. Another drawback of this method is the presence in all products of an ester group in γ-position.

Intramolecular Wittig reactions have also been described to yield substituted pyrroline derivatives starting from oxazolone compounds (Scheme 6) (Clerici, F.; Gelmi, M. L.; Pocar, D.; Rondene, R. *Tetrahedron* 1995, 51, 9985). In this method, oxazolone derivatives are first reacted with triphenylvinylphosphonium bromide to afford the intermediate phosphonium functionalized oxazolone derivatives through Michael addition. The quenching of the reaction with methanol and p-toluenesulfonic acid as catalyst affords the corresponding acylamino methyl ester. In a second step, this latter phosphonium salt undergoes an intramolacular Wittig reaction to yield the expected pyrroline derivatives.

Scheme 6.

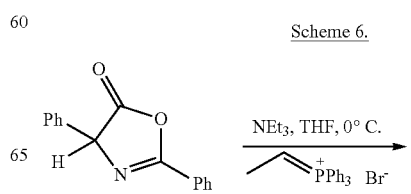

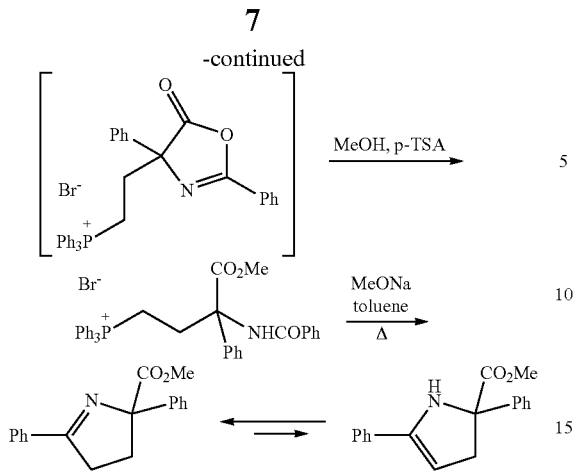

The phosphonium bromide used by Clerici et al. is a derivative of amino acid wherein the alpha carbon is quaternary, which promotes the cyclization by Thorpe Ingold effect. The conditions used for the Wittig reaction are harsch, with the use of a strong base and reflux conditions. These conditions are known to be racemizing conditions and there is nothing in this document relative to the stereoselectivity of the reaction.

TECHNICAL PROBLEM AND SOLUTION

As shown above, synthesis known in the prior art to obtain unsaturated amino acids are not adapted to the synthesis of libraries of compounds: either they are compound-specific, or involve multiple steps, or are not stereoselective, or have unsatisfying yields and more generally lack of versatility.

Therefore, there remains a need for the development of new methods of synthesis of libraries of unsaturated α-amino acids, and especially of γ,δ-unsaturated amino acids. Such methods should be versatile enough to easily lead to broad libraries of unnatural amino acids that may be tested for synthetic applications as well as for their biological activity.

In continuity to the phosphorus chemistry developed by the Applicant, intensive research was conducted on the synthesis of amino acids bearing organophosphorus group or metallophosphorus group on the lateral chain. These syntheses led the Applicant to study their application for the preparation of unsaturated amino acids by creation of a C=C double bond by Wittig or Wittig-Horner reaction.

As a result, the Applicant found an optimized process of synthesis of γ,β-unsaturated amino acids of general formula (I) implying a Wittig reaction between a phosphonium salt of general formula (II) derived from aspartic acid and various compounds (IV), said compounds (IV) being ketones or aldehydes of general formula $R_aCOR_b$ or ketones derivatives such as $[R_a, R_b]$-trisubstituted trioxanes, imines of general formula $R_aR_bC=NR_c$ or bisulfitic combinations of general formula $R_aR_bC(OH)(SO_3Na)$ (Scheme 7).

Scheme 7.

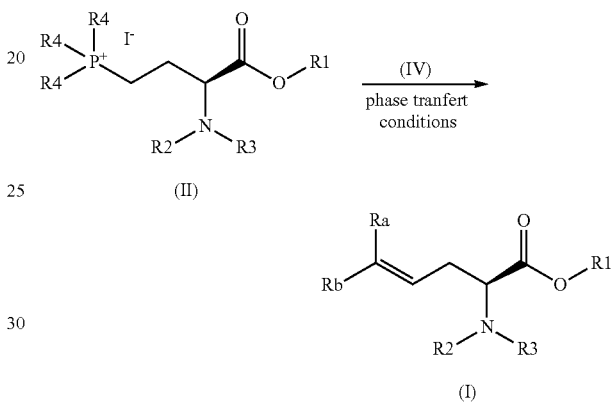

As depicted in scheme 8, when R1 is different from a hydrogen atom, compound (I) corresponds to the general formula (I') wherein R5 is not an hydrogen atom and is obtained from compound (II') which is yielded from compound (III). When R1 is a hydrogen atom, compound (I) corresponds to the general formula (I") and is obtained from compound (II") which is yielded from compound (II').

Scheme 8.

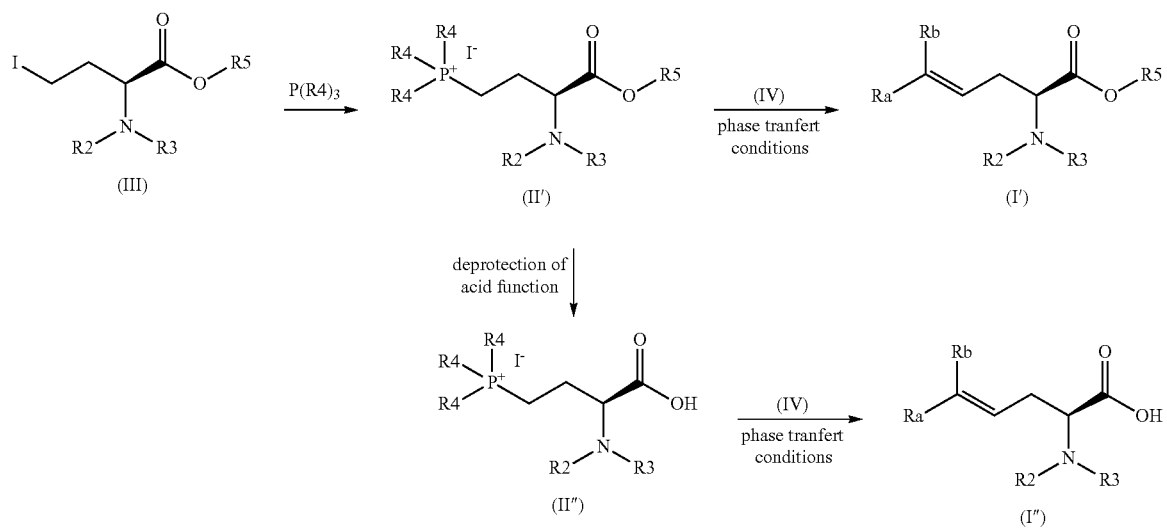

The process developed by the Applicant for producing compound (I') or (I") from (II') and (II") respectively, involves specific preliminary steps depending on the nature of R1 group. Compound (II') results from the quaternization of a phosphine P(R4)₃ by the iodo derivative (III). Compound (II") results from the deprotection of the acid function of compound (II').

Applications of γ,β-unsaturated amino acids (I) as intermediates in organic synthesis have been explored. Especially, compounds (I) may be used as reactants in Suzuki-Miyaura coupling, Diels Alder reaction, Michael addition or in click chemistry. Compounds (I) may also have applications as contrast agents in medical imaging, especially in IRM or in PET, and may also presents interesting bioactivity.

DEFINITIONS

In the present invention, the following terms have the following meanings:

"alkyl", refers to any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl. The alkyl group may be substituted by a substituted or unsubstitued aryl group;

"cycloalkyl", refers to a substituted or not substituted cyclic alkyl substituent such as cyclopropyl, cyclopentyl, or cyclohexyl;

"aryl", refers to a mono- or polycyclic system of 5 to 20, and preferably 6 to 12, carbon atoms having one or more aromatic rings (when there are two rings, it is called a biaryl) among which it is possible to cite the phenyl group, the biphenyl group, the 1-naphthyl group, the 2-naphthyl group, the tetrahydronaphthyl group, the indanyl group and the binaphthyl group. The term aryl also means any aromatic ring including at least one heteroatom chosen from an oxygen, nitrogen or sulfur atom. The aryl group can be substituted by 1 to 3 substituents chosen independently of one another, among a hydroxyl group, a substituted or unsubstituted linear or branched alkyl group comprising 1, 2, 3, 4, 5 or 6 carbon atoms, in particular methyl, ethyl, propyl, butyl, a cycloakyl group, an alkanoyl, an arylalkyl, an aralkyloxy, an alkoxy group, a halogen atom, in particular bromine, chlorine and iodine, a nitro group, a cyano group, an azido group, an adhehyde group, a boronato group, a phenyl, trifluoromethyl CF₃, methylenedioxy, ethylenedioxy, SO₂NRR', NRR', COOR (where R and R' are each independently selected from the group consisting of H and alkyl), an second aryl group which may be substituted as above;

"alkyloxy", refers to any O-alkyl group;

"cycloalkyloxy", refers to any O-cycloalkyl group;

"aryloxy", refers to any O-aryl group;

"alkenyl", refers to any linear or branched hydrocarbon chain having at least one double bond, of 2 to 12 carbon atoms, and preferably 2 to 6 carbon atoms. The alkenyl group may be substituted by a substituted or unsubstituted aryl group;

"metallocenyl" refers to a group comprising a metal sandwiched between two cyclopentadienyl groups;

"Boc" refers to tert-butyloxycarbonyl, commonly used to protect the α-amino group in peptide synthesis;

"electroattractive group" refers to a functional group having the ability to attract electrons, such as—but not limitatively—ester group, tosyl group or phosphonyl group.

"about" preceding a figure means plus or less 10% of the value of said figure.

SUMMARY

The present invention relates to a process for producing a compound of formula (I),

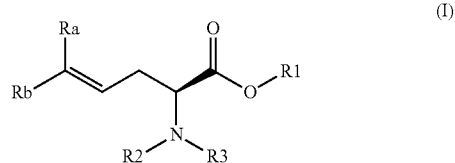

comprising performing a Wittig reaction by reacting a phosphonium salt of general formula (II)

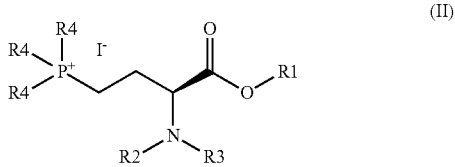

wherein
R1 represents a hydrogen atom or R5, wherein R5 is a substituted or unsubstituted group selected from alkyl, cycloalkyl, aryl, alkenyl;

R2 and R3 may be the same or different and represent each a hydrogen atom or a substituted or unsubstituted group selected from alkyl, cycloalkyl, aryl, alkenyl, —COR, wherein R is a substituted or unsubstituted group selected from alkyl, cycloalkyl, aryl, alkenyl, alkyloxy, cycloalkyloxy, aryloxy;

R4 represents a substituted or unsubstituted group selected from alkyl, cycloalkyl, aryl, alkenyl;

with compound (IV), wherein compound (IV) is selected in the group consisting of a ketone or aldehyde of formula RaCORb, an imine of formula RaRbC=NRc, a [Ra,Rb]-trisubstituted trioxane and a RaRbC(OH)(SO₃Na); wherein Ra and Rb may be the same or different and representent each a hydrogen atom or a substituted or unsubstituted group selected from alkyl, alkenyl, cycloalkyl, aryl, metallocenyl and —COR, wherein R is a substituted or unsubstituted group selected from alkyl, cycloalkyl, aryl, alkenyl, alkyloxy, cycloalkyloxy and aryloxy; and wherein Rc represent a hydrogen atom, a substituted or unsubstituted group selected from alkyl, cycloalkyl, aryl or an electroattractive group;

in presence of a weak base and of a solvent suitable for phase transition conditions, resulting in compound (I), wherein the weak base is selected in the group comprising Cs₂CO₃, Li₃PO₄, NaH, K₃PO₄ and K₂CO₃.

According to one embodiment, the process of the invention comprises reacting phosphonium salt (II') and leading to compound (I')

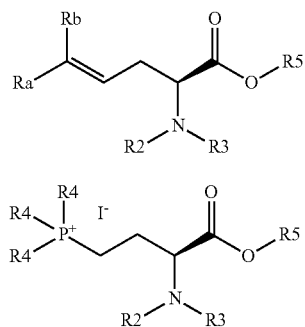

(I')

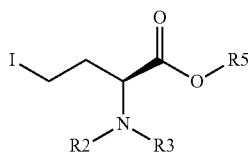

(II')

wherein Ra, Rb, R2, R3, R4 and R5 are as defined above;
further comprises a preliminary step comprising the quaternization of a phosphine P(R4)₃, wherein R4 is as defined above;
with a iodo derivative of general formula (III)

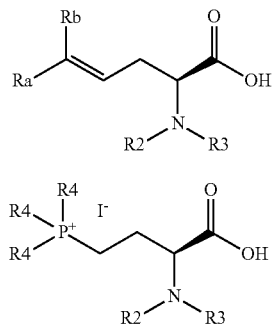

(III)

wherein R2, R3 and R5 are as defined above,
resulting in the phosphonium salt of formula (II').

According to another embodiment, the process of the invention comprises reacting phosphonium salt (II") and leading to compound (I")

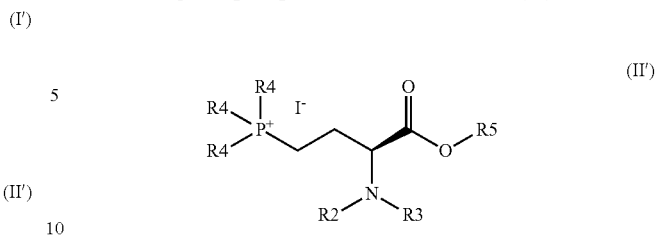

(I")

(II")

wherein Ra, Rb, R2, R3 and R4 are as defined above,
further comprises two preliminary steps:
a) quaternization of a phosphine P(R4)₃, wherein R4 is as defined above, with a iodo derivative of general formula (III)

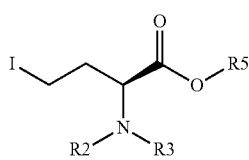

(III)

wherein R2, R3 and R5 are as defined above, resulting in a phosphonium salt of formula (II')

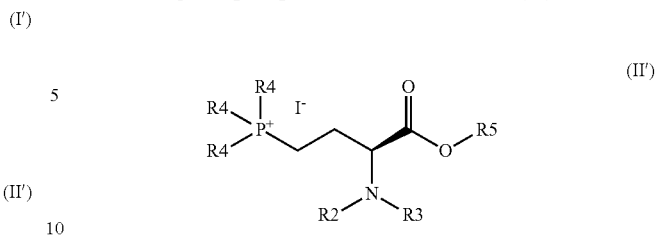

(II')

wherein R2, R3, R4 and R5 are as defined above, and
b) deprotecting the carboxylic acid function of phosphonium salt (II'), resulting in the corresponding phosphonium salt of formula (II").

According to one embodiment, R2 is a hydrogen atom, R3 is a Boc group, R4 is phenyl and R5 is allyl.

According to one preferred embodiment, the weak base is $K_3PO_4$, $Cs_2CO_3$ or $K_2CO_3$, more preferably the weak base is $K_3PO_4$.

According to one embodiment, the solvent suitable for phase transition conditions is selected from the group comprising chlorobenzene, dichloromethane, chloroform, dichlorobenzene, dichloroethane, dioxane, preferably is chlorobenzene or dioxane.

According to one embodiment, R1 is selected from the group consisting of hydrogen atom, allyl group and benzyl group.

According to one embodiment, R2 is a hydrogen atom or Boc and R3 is Boc.

According to one embodiment, phosphine P(R4)₃ is selected from the group comprising tricyclohexylphosphine, triphenylphosphine, trifurylphosphine, tri(4-methoxyphenyl)phosphine, tri(4-trifluoromethylphenyl)phosphine, tri(4-fluorophenylphosphine) and tri(4-chlorophenyl)phosphine, preferably phosphine P(R4)₃ is triphenylphosphine.

According to one embodiment, RaCORb is selected from the group comprising benzaldehyde, 4-trifluoromethylbenzaldehyde, 4-nitrobenzaldehyde, 4-cyanobenzaldehyde, 4-methoxybenzaldehyde, 3,4-dimethoxybenzaldehyde, 2-furaldehyde, 3-phenylpropanal, paraformaldehyde, phenylacetaldehyde, 4-(4,4,5,5-tetramethyl-1,3,2-dioxaborolan-2-yl)benzaldehyde, aldehyde derived from calix-[4]-arene, ferrocene-carboxaldehyde, m-phthaldialdehyde, trans-cinnamaldehyde, (E)-4-azidophenylprop-2-enal, 4-oxo-2-butenoate, 3-methylbutenal, 4-nitro-trans-cinnamaldehyde, thiophene propenal, furyl propenal, and trifluoromethylacetophenone.

According to one embodiment, R5 is an allyl group and wherein the deprotection of the carboxylic acid function of compound (II') is performed in presence of $Pd_2(dba)_3$, dppe and $HNEt_2$.

The present invention also relates to a process for manufacturing iodo derivative (III) wherein R2 is hydrogen and R3 is Boc group of general formula (III')

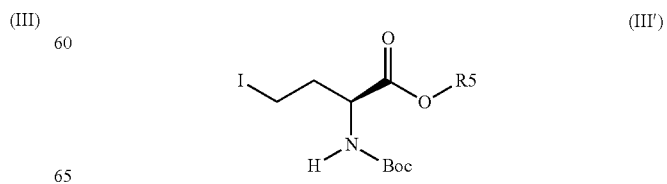

(III')

wherein R5 is as defined above, comprising:
  protecting the acid function of the lateral chain of L-aspartic acid by transformation into monoester by esterification with methanol;
  protecting the amino function with a Boc group;
  protecting the remaining acid function by esterification in the presence of the bromide derivative R5-Br to lead to the corresponding diester;
  further protecting the amino function with a second Boc group;
  reducing the terminal ester in aldehyde using DIBAL;
  further reducing the aldehyde group with NaBH$_4$ to lead to the N,O protected homoserine derivative;
  reacting with iodine in the presence of triphenylphosphine and imidazole to lead to the N-diprotected amino ester;
  reacting with NaI in presence of CeCl$_3$ and further hydrolysing to obtain the N-monoprotected compound (III').

The present invention also relates to a compound of general formula (I)

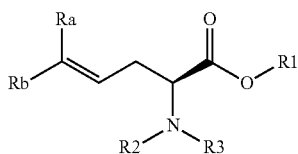

(I)

wherein
  Ra and Rb may be the same or different and representent each a hydrogen atom or a substituted or unsubstituted group selected from alkyl, alkenyl, cycloalkyl, aryl, metallocenyl and —COR, wherein R is a substituted or unsubstituted group selected from alkyl, cycloalkyl, aryl, alkenyl, alkyloxy, cycloalkyloxy and aryloxy;
  R1 represents a hydrogen atom or R5, wherein R5 is a substituted or unsubstituted group selected from alkyl, cycloalkyl, aryl, alkenyl;
  R2 and R3 may be the same or different and represent each a hydrogen atom or a substituted or unsubstituted group selected from alkyl, cycloalkyl, aryl, alkenyl, —COR, wherein R is a substituted or unsubstituted group selected from alkyl, cycloalkyl, aryl, alkenyl, alkyloxy, cycloalkyloxy, aryloxy;
  provided that when R1 is t-butyl and {R2, R3} is {H, PhF} or {PhF, H}, then {Ra, Rb} is not {H, —COOMe}, {—COOMe, H}, {H, —CO(CH$_2$)$_n$CH(NHPhF)(CO$_2$tBu) with n is 1, 2 or 3} or {—CO(CH$_2$)$_n$CH(NHPhF)(CO$_2$tBu) with n is 1, 2 or 3, H};
  provided that when Ra is an aryl group or a group comprising an aryl substituent, Rb is not an aryl group or a group comprising an aryl substituent;
  provided that when Ra is a unsubstitued or alkyl-substituted α,ω-alkylene having from 0 to 3 carbon atoms substituted by a phosphino, phosphonyl or phosphono group, Rb is not selected from the group consisting of hydrogen, alkyl, haloalkyl, hydroxyalkyl, alkoxyalkyl, arylalkyl, akenyl or aryl;
  provided that when R1 is a hydrogen atom and {R2,R3} is {H, H}, then {Ra, Rb} is not {H, H};
  provided that when R1 is a hydrogen atom and {R2,R3} is {Troc, H} or {H, Troc}, then {Ra, Rb} is not {H, —CH=CH—CH(Me)$_2$} or {—CH=CH—CH(Me)$_2$, H};
  provided that when R1 is a methyl group and {R2,R3} is {Boc, H} or {H, Boc}, then {Ra, Rb} is not {H, H};
  provided that when R1 is a methyl group and {R2,R3} is {H, H}, then {Ra, Rb} is not {H, —CH=CH—CH(Me)$_2$} or {—CH=CH—CH(Me)$_2$, H}.

The present invention also relates to a compound of general formula (II)

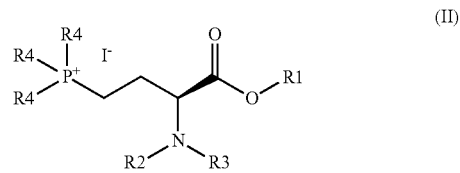

(II)

wherein
  R1 represents a hydrogen atom or R5, wherein R5 is a substituted or unsubstituted group selected from alkyl, cycloalkyl, aryl, alkenyl;
  R2 and R3 may be the same or different and represent each a hydrogen atom or a substituted or unsubstituted group selected from alkyl, cycloalkyl, aryl, alkenyl, —COR, wherein R is a substituted or unsubstituted group selected from alkyl, cycloalkyl, aryl, alkenyl, alkyloxy, cycloalkyloxy, aryloxy;
  R4 represents a substituted or unsubstituted group selected from alkyl, cycloalkyl, aryl, alkenyl.

The present invention also relates to a compound of general formula (III)

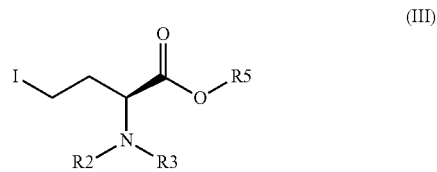

(III)

wherein
  R2 and R3 may be the same or different and represent each a hydrogen atom or a substituted or unsubstituted group selected from alkyl, cycloalkyl, aryl, alkenyl, —COR, wherein R is a substituted or unsubstituted group selected from alkyl, cycloalkyl, aryl, alkenyl, alkyloxy, cycloalkyloxy, aryloxy;
  R5 represents a substituted or unsubstituted group selected from alkyl, cycloalkyl, aryl, alkenyl;
  provided that when R5 is methyl, R2 and R3 are not both Boc groups;
  provided that when R5 is benzyl, {R2,R3} is not {H, Boc} or {Boc, H};
  provided that when R5 is ethyl, {R2,R3} is not {H,C(=O)—O—CH$_2$-Ph} or {C(=O)—O—CH$_2$-Ph, H}.

The present invention also relates to a library of two or more compounds of formula (I) as described above.

DETAILED DESCRIPTION

It is appreciated that in any of the mentioned reactions, any reactive group in the substrate molecules may be protected according to conventional chemical practice. Suitable protecting groups in any of the mentioned reactions are those used conventionally in the art. The methods of formation and removal of such protecting groups are those conventional methods appropriate to the molecule being protected.

Synthesis of γ,β-Unsaturated Amino Acids (I) by Wittig Reaction

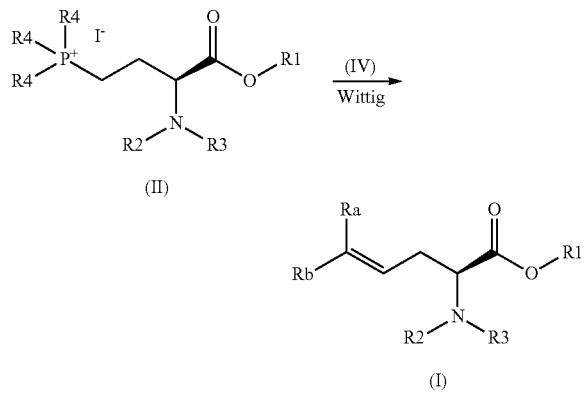

In the present invention, γ,β-unsaturated α-amino acids of general formula (I) are obtained by a Wittig reaction between a phosphonium salt of general formula (II) and a compounds (IV), said compound (IV) being a ketone or aldehyde of general formula $R_aCOR_b$ or ketones derivatives such as $[R_a, R_b]$-trisubstituted trioxanes, imines of general formula $R_aR_bC=NR_c$ or bisulfitic combinations of general formula $R_aR_bC(OH)(SO_3Na)$.

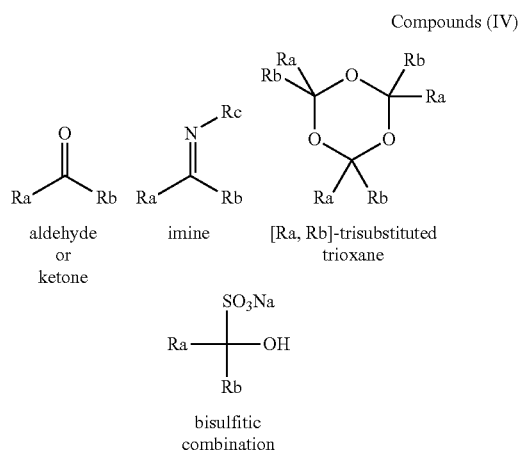

Classical conditions for Wittig reaction involve a phosphonium salt, an aldehyde or a ketone and a strong base. Therefore, the Applicant first performed the synthesis of compound (I) in classical conditions, using t-BuLi, LDA or LiHMDS as strong base. Surprisingly, compound (I) was obtained with yields ranging from 10 to 30% and, in some cases, partial racemization occurred. Optimization of these results was considered necessary in view of developing a process for the synthesis of libraries of compounds (I).

As a result of intensive research, the Applicant found that phase transfer conditions in combination with the use of a weak base give interesting results with yields over 50% (often over more than 70%) and with very few, if any, racemization.

These results are all the more surprising as the phosphonium ylide formed from compound (II) during the Wittig reaction is not stabilized and as it is usually admitted than Wittig reaction implying weak bases are only possible with stabilized ylides.

Therefore, the present invention relates to a process for producing a compound of formula (I), comprising performing a Wittig reaction by reacting a phosphonium salt of general formula (II)

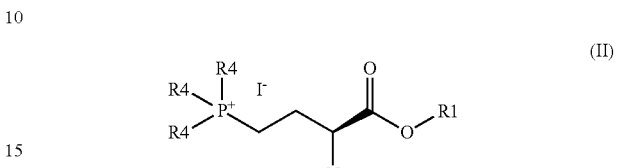

wherein

R1 represents a hydrogen atom or R5, wherein R5 is a substituted or unsubstituted group selected from alkyl, cycloalkyl, aryl, alkenyl;

R2 and R3 may be the same or different and represent each a hydrogen atom or a substituted or unsubstituted group selected from alkyl, cycloalkyl, aryl, alkenyl, —COR, wherein R is a substituted or unsubstituted group selected from alkyl, cycloalkyl, aryl, alkenyl, alkyloxy, cycloalkyloxy, aryloxy;

R4 represents a substituted or unsubstituted group selected from alkyl, cycloalkyl, aryl, alkenyl;

with compound (IV), wherein compound (IV) is selected in the group consisting of a ketone or aldehyde of formula RaCORb, an imine of formula RaRbC=NRc, a [Ra,Rb]-trisubstituted trioxane and a RaRbC(OH)(SO₃Na); wherein Ra and Rb may be the same or different and representent each a hydrogen atom or a substituted or unsubstituted group selected from alkyl, alkenyl, cycloalkyl, aryl, metallocenyl and —COR, wherein R is a substituted or unsubstituted group selected from alkyl, cycloalkyl, aryl, alkenyl, alkyloxy, cycloalkyloxy and aryloxy; and wherein Rc represent a hydrogen atom, a substituted or unsubstituted group selected from alkyl, cycloalkyl, aryl or an electroattractive group.

in presence of a weak base and of a solvent suitable for phase transition conditions, resulting in compound (I).

According to one embodiment, the synthesis of compound (I) is carried out in presence of 1 to 10 equivalents, preferably of 1 to 5 of compound (IV). According to an embodiment, the synthesis of compound (I) is carried out in presence of 1.5 equivalents of compound (IV). According to another embodiment, the synthesis of compound (I) is carried out in presence of 1.2 equivalents of compound (IV). According to another embodiment, the synthesis of compound (I) is carried out in presence of 2 equivalents of compound (IV).

According to a preferred embodiment, compound (IV) is an aldehyde. According to a preferred embodiment, compound (IV) is selected from the group comprising benzaldehyde, 4-trifluoromethylbenzaldehyde, 4-nitrobenzaldehyde, 4-cyanobenzaldehyde, 4-methoxybenzaldehyde, 3,4-dimethoxybenzaldehyde, 2-furaldehyde, 3-phenylpropanal, paraformaldehyde, phenylacetaldehyde, 4-(4,4,5,5-tetramethyl-1,3,2-dioxaborolan-2-yl)benzaldehyde, aldehyde derive from calix-[4]-arene, ferrocene-carboxaldehyde, m-phthaldialdehyde, trans-cinnamaldehyde, (E)-4-azidophenylprop-2-enal, 4-oxo-2-butenoate, 3-methylbutenal, 4-nitro-trans-cinnamaldehyde, thiophene propenal, furyl propenal.

According to another embodiment, compound (IV) is a ketone. According to a preferred embodiment, compound (IV) is trifluoromethylacetophenone.

According to an embodiment, the synthesis of compound (I) is carried out in presence of a base. According to an embodiment, the base is a strong base selected from the group comprising n-BuLi, t-BuLi, lithium diisopropylamine (LDA), lithium bis(trimethylsilyl)amide (LiHMDS), KHMDS, NaHMDS, sec-BuLi, PhLi. According to another embodiment, the base is a weak inorganic base selected from the group comprising $Cs_2CO_3$, $Li_3PO_4$, NaH, $K_3PO_4$, $K_2CO_3$. According to a preferred embodiment, the base is $K_3PO_4$. According to a particular embodiment, the weak base is not $NEt_3$.

According to one embodiment, the synthesis of compound (I) is carried out in presence of 1 to 10 equivalents of base. In one embodiment, the synthesis of compound (I) is carried out in presence of 2 to 6, preferably 6 equivalents of base. In another embodiment, the synthesis is carried out in presence of 1 to 2 equivalents of base, preferably 1.2 equivalents of base.

According to one embodiment, the base used in the synthesis of compound (I) is in a solid or liquid form. According to a preferred embodiment, the base is in a solid form.

According to one embodiment, the synthesis of compound (I) is carried out in anhydrous conditions. According to another embodiment, the synthesis of compound (I) is carried out in presence of less than 1 equivalent of water, preferably about 0.8 equivalent of water.

According to one embodiment, the synthesis of compound (I) is carried out in a solvent selected from the group comprising tetrahydrofuran, ethanol, dimethylformamide, chlorobenzene, dichlorobenzene, dichloromethane, chloroform, dichloroethane, dioxane, dimethylether (DME), ethylene glycol ethers, propylene glycol ethers, diglyme. According to one embodiment, the synthesis of compound (I) is usually carried out in a solvent suitable for phase transfer conditions. According to a preferred embodiment, the synthesis of compound (I) is carried out in a solvent selected from the group comprising chlorobenzene, dichlorobenzene, dichloromethane, chloroform, dichloroethane, dioxane. According to a preferred embodiment the solvent used is chlorobenzene. According to another preferred embodiment, the solvent used is dioxane.

According to one embodiment, the synthesis of compound (I) is carried out at a temperature ranging from 25 to 140° C., preferably from 50 to 120, more preferably 90° C.

According to one embodiment, the synthesis of compound (I) is carried out for a time ranging from 1 to 48 hours, preferably from 12 to 24 hours, more preferably 12 hours.

According to a preferred embodiment, the synthesis of compound (I) is carried out in chlorobenzene as solvent, in anhydrous conditions, by heating the reaction at 90° C. overnight, using 6 equivalent of $K_3PO_4$, and 1.5 equivalent of aldehyde.

According to another preferred embodiment, the synthesis of compound (I) is carried out in dioxane as solvent, in anhydrous conditions, by heating the reaction at 90° C. overnight, using 6 equivalent of $K_3PO_4$, and 1.2 equivalent of aldehyde.

According to one embodiment, the yield of the synthesis of compound (I) is ranging from 10 to 100%, preferably from 50 to 100%.

According to one embodiment, the synthesis of compound (I) is stereoselective.

According to one embodiment, compound (I) is purified by using chromatographic techniques or by recrystallization.

Compounds (I) with R1 Different from a Hydrogen Atom: (I')

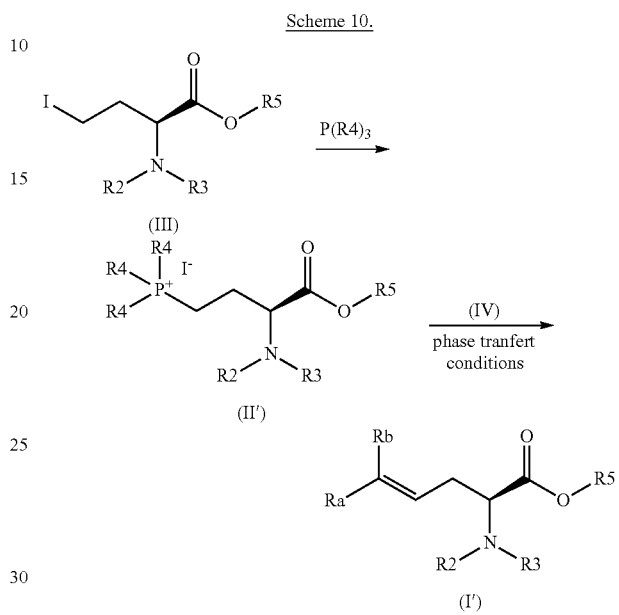

Scheme 10.

In a particular embodiment of the invention, substituent R1 is different of a hydrogen atom. In this specific case, compounds (I) have the specific general formula (I') wherein R5 is as defined above. Compounds (I') are obtained as described above by Wittig reaction from the phosphonium salt of particular formula (II').

In one embodiment, phosphonium salt (II') is obtained by the quaternization of a phosphine $P(R4)_3$, wherein R4 is as defined above with a iodo derivative of general formula (III) wherein R2, R3 and R5 are as defined above.

According to a preferred embodiment, R5 is allyl or benzyl, more preferably allyl. According to another preferred embodiment, R2 and R3 are each Boc groups. According to another preferred embodiment, R2 is a hydrogen atom and R3 is a Boc groups.

According to a preferred embodiment, the phosphine $P(R4)_3$ is selected from the group comprising tricyclohexylphosphine, triphenylphosphine, trifurylphosphine, tri(4-methoxyphenyl)phosphine, tri(4-trifluoromethylphenyl)phosphine, tri(4-fluorophenylphosphine), tri(4-chlorophenyl)phosphine. According to a very preferred embodiment, the phosphine $P(R4)_3$ is triphenylphosphine.

According to one embodiment, the synthesis of compound (II') is carried out in presence of 2 to 5 equivalents, preferably of 2 to 3, more preferably 2 equivalents of phosphine $P(R4)_3$.

According to one embodiment, the synthesis of compound (II') is performed in a solvent selected from the group comprising tetrahydrofuran, acetonitrile, chloroforme, acetone, or mixtures thereof. According to another embodiment, the synthesis of compound (II') is performed without solvent.

According to one embodiment, the synthesis of compound (II') is performed at a temperature ranging from 70 to 120° C., preferably from 70 to 90, more preferably at 80° C.

According to one embodiment, the synthesis of compound (II') is performed for a time ranging from 1 to 24 hours, preferably from 1 to 4 hours, more preferably for 2 hours.

According to one embodiment, compound (II') is purified by using chromatographic techniques or by recrystallization.

According to a preferred embodiment, R4 is phenyl.

According to a preferred embodiment, when R4 is phenyl, the synthesis of the corresponding compound (II') is performed without solvent by heating 2 hours at 80° C., using 2.5 equivalent of PPh₃.

According to one embodiment, the synthesis of compound (II') is stereoselective.

According to one embodiment, the yield of the synthesis of compound (II') is ranging from 30 to 80%, preferably from 40 to 70%.

Compounds (I) with R1 is a Hydrogen Atom: (I")

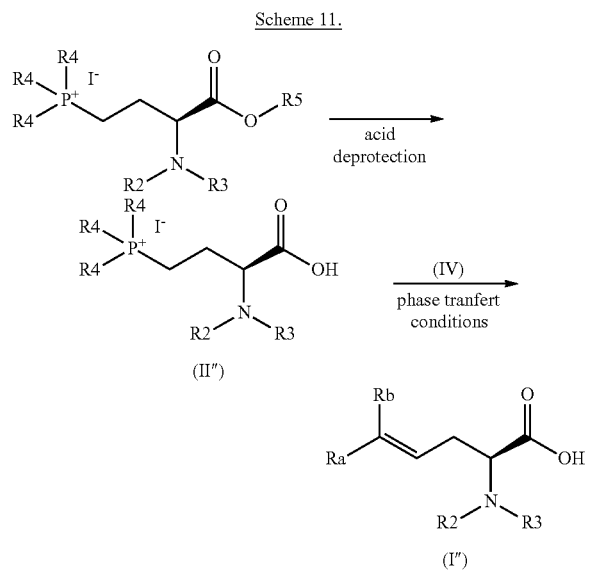

In a particular embodiment of the invention, substituent R1 is a hydrogen atom. In this specific case, compounds (I) have the general formula (I") and is obtained as described above by Wittig reaction from the phosphonium salt of particular formula (II").

In one embodiment, phosphonium salt (II") is obtained by deprotecting the carboxylic acid function of phosphonium salt (II'). Protected phosphonium salt (II') may be obtained as described above.

According to a preferred embodiment, R2 and R3 are each Boc groups. According to another preferred embodiment, R2 is a hydrogen atom and R3 is a Boc group.

In a particular embodiment, substituent R5 of compound (II') is a allyl group. In this embodiment, the deprotection of carboxylic acid function of compound (II') is performed by deallylation with diethylamine. According to a preferred embodiment, the deallylation is performed with diethylamine and is catalyzed by tris(dibenzylideneacetone)dipalladium (0) (Pd₂(dba)₃) in presence of 1,2-bis(diphenylphosphino)ethane (dppe). According to an embodiment, the catalysis is obtained in presence of 2.5% mol of Pd₂(dba)₃. According to a preferred embodiment, the deallylation is performed in the conditions described in Guibé, F. *Tetrahedron*, 1998, 54, 2967-3042.

According to one embodiment, the deallylation is carried out in a solvent selected from the group comprising THF, dioxane, benzene, dichloromethane, chloroforme, DMF, toluene.

According to one embodiment, the deallylation is carried out at a temperature ranging from 0 to 50° C., preferably at 25° C.

According to one embodiment, the deallylation is carried out for a time ranging from 4 to 48 hours, preferably from 12 to 24 hours.

According to one embodiment, the yield of the deallylation is ranging from 30 to 90%, preferably from 50 to 90%.

According to another embodiment, the deprotection of carboxylic acid function of compound (II') is performed by deallylation reaction with phenylsilane. According to a preferred embodiment, the deallylation is performed with phenylsilane and is catalyzed by tetrakistriphenylphosphinepalladium(0) (Pd(PPh₃)₄). According to an embodiment, the catalysis is obtained in presence of 3.5% mol of Pd(PPh₃)₄. According to a preferred embodiment, the deallylation is performed according to the procedure described in Vazquez M. E., Blanco J. B. and Imperiali B., *J. Am. Chem. Soc.* 2005, 127, 1300-1306.

According to one embodiment, the enantiomeric purity of compound (II") is determined by $^{31}$P NMR by comparison with a racemic sample in presence of the commercially available complexing agent (M,R)-BINPHAT, in conditions described in Hebbe V., Londez A., Goujon-Gonglinger C., Meyer F., Uziel J., Jugé S, and Lacour J., *Tetrahedron Lett.*, 2003, 44, 2467-2471.

According to one embodiment, the synthesis of compound (II") is stereoselective.

According to one embodiment, compound (II") is purified by using chromatographic techniques or by recrystallization.

Synthesis N-Protected γ-Iodo Aminoester (III)

In a particular embodiment of the invention, R2 is a hydrogen atom and R3 is a Boc group and compound (III) is of general formula (III'). In this case, the corresponding iodo derivatives (III') may be synthesized according to scheme 12.

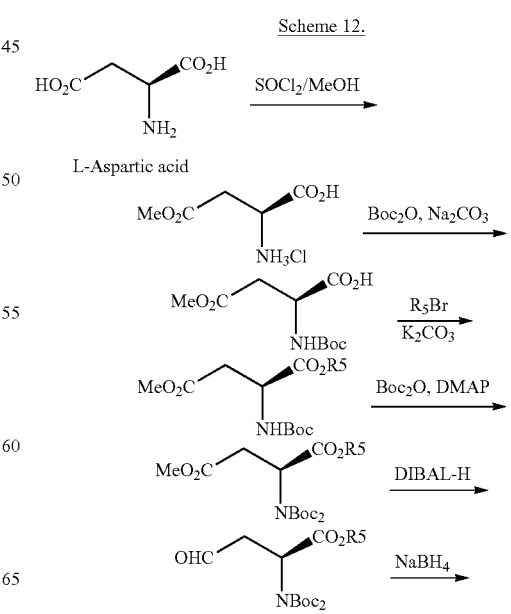

-continued

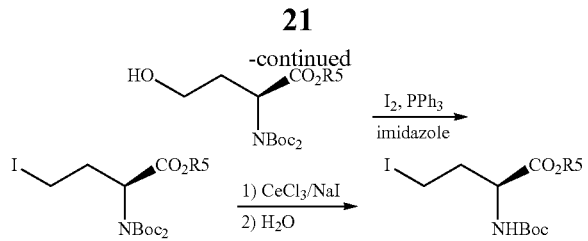

According to a preferred embodiment of the present invention, iodo derivative (III) is prepared with an overall yield ranging from 20 to 40%, starting from L-aspartic acid according to Scheme 12.

According to this embodiment, the first step consists in protecting the acid function of the lateral chain of L-aspartic acid by transformation into monoester by esterification with methanol (Brown F. K., Brown P. J., Bickett D. B., Chambers C. L., Davies H. G., Deaton D.N., Drewry D., Foley M., McElroy A. B., Gregson M., McGeehan G. M., Myers P. L., Norton D., Salovich J. M., Schoenen F. J., Ward P., *J. Med. Chem.*, 1994, 37, 674-688).

The second step consists in the protection of the amino group with a t-butyloxycarbonyl group (Ramalingam K. and Woodard R. W., *J. Org. Chem.*, 1988, 53, 1900-1903).

The third step consists in the protection of the remaining acid function by esterification in the presence of the bromide derivative R5-Br to lead to the corresponding diester (Stein K. A. and Toogood P. L., *J. Org. Chem.*, 1995, 60, 8110-8112).

The N-protected γ-iodo aminoester (III') is obtained after four supplementary steps according to a strategy described in the literature (Adamczyk M., Johnson D. and Reddy R. E., *Tetrahedron: Asymmetry*, 2000, 11, 3063-3068). The amino group is first further protected with $Boc_2O$. The terminal ester is then reduced in aldehyde using DIBAL. A further reduction with $NaBH_4$ leads to the N,O protected homoserine derivative. The iodo amino ester is finally obtained by reaction with iodine in presence of triphenylphosphine and imidazole.

The last step consists in the transformation of the N,N-diprotected γ-iodo aminoester into the corresponding N-monoprotected γ-iodo aminoester (III'), by reaction of NaI in presence of $CeCl_3.7H_2O$ and further hydrolysis (Yadav J. S., Dubba Reddy B. V. and Reddy K. S., *Synlett*, 2002, 3, 468-470).

According to one embodiment, the analysis of the N-protected γ-iodo aminoester and of the N-monoprotected γ-iodo aminoester (III') by HPLC on chiral column shows that no racemization occurs during all these steps of synthesis.

Applications of Compounds (I)

Applications of γ,β-unsaturated amino acids (I) as intermediates in organic synthesis have been explored. Especially, compounds (I) may be used as reactants in Suzuki-Miyaura coupling, Diels Alder reaction, Michael addition or in click chemistry. Compounds (I) may also have applications as contrast agents in medical imaging, especially in IRM or in PET, and may also presents interesting bioactivity.

EXAMPLES

The present invention is further illustrated by the following examples which are provided by way of illustration only and should not be considered to limit the scope of the invention.

A. Generalities

Material and Methods

Chiral HPLC analysis were performed on SHIMADZU 10-series apparatus, using chiral columns (Chiralcel OD-H, Chiralcel AD, Chiralcel OJ, Lux 5 µm cellulose-2), and with hexane/propan-2-ol mixtures as the mobile phase (Flow rate 1 mL $min^{-1}$; UV detection λ=254 nm). Thin layer chromatography (TLC) was performed on 0.25 mm E Merck pre-coated silica gel plates and exposed by UV, potassium permanganate, ninhydrine or iodine treatment. Flash chromatography was performed with the indicated solvents using silica gel 60 A, (35-70 µm; Acros) or aluminium oxide 90 standardized (Merck). All NMR spectra data were recorded on BRUKER AVANCE 300, 500 and 600 spectrometers at ambient temperature. Data are reported as s=singlet, d=doublet, t=triplet, q=quartet, m=multiplet, brs=broad singlet, brd=broad doublet, dhept=doublet of heptuplet, coupling constant(s) in Hertz. Melting points were measured on a Kofler bench melting point apparatus and are uncorrected. Optical rotations values were recorded at 20° C. on a Perkin-Elmer 341 polarimeter, using a 10 cm quartz vessel. Infrared spectra were recorded on a Bruker Vector 22 apparatus. Mass and HRMS spectra were recorded on Mass, Bruker ESI micro TOF-Q apparatus, at the Universite de Bourgogne (Dijon). Elemental analyses were measured with a precision superior to 0.3% at the Microanalysis Laboratories of the University of Bourgogne (Analyseur CHNS/O Thermo Electron Flash EA 1112 Serie).

B. Synthesis of N-Protected γ-Iodo Aminoester (III)

B.1. Synthesis of (S)-2-(t-butyloxycarbonylamino) allyl-4-iodobutanoate (III')

B.1.1 Synthesis of (S)-aspartate methyl monoester chlorhydrate

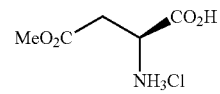

To 3.8 mL (41.2 mmol) of $SOCl_2$ in 26 mL of dry methanol, were added at −10° C., 5 g of L-aspartic acid (37.6 mmol). The mixture was stirred two hours at room temperature and 75 mL of diethyl ether were added. The white solid was filtered and washed with 2×50 mL of diethyl ether to afford (S)-aspartate methyl monoester chlorhydrate in 85% yield. White solid. $^1H$ NMR (300 MHz, DMSO): δ (ppm)=3.05 (dd, J=3.4, 4.7 Hz, 2H, $CH_2$), 3.78 (s, 3H, $OCH_3$), 4.31-4.35 (m, 1H, CHN).

B.1.2. Synthesis of 2-(S)-(t-butyloxycarbony-lamino)-(methoxycarbonyl)butanoic acid

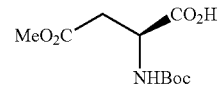

To a solution of 3.74 g (20.5 mmol) of (S)-aspartate methyl monoester chlorhydrate in 85 mL of a mixture dioxane/$H_2O$ (2:1), were added at 0° C., 2.21 g (20.8 mmol) of $Na_2CO_3$. After 30 minutes, 2.21 g (20.8 mmol) of $Na_2CO_3$ and 5 g (25.7 mmol) of $Boc_2O$ were added to the mixture which was stirred overnight at room temperature. The solvent was concentrated under vacuum, and the residue was poured into a mixture ice-water (60 mL). The aqueous layer was washed with 2×25 mL of diethyl ether and acidified until pH=3 with 100 mL of NaHSO$_4$ (1M). The aqueous layer was extracted with diethyl ether (3×75 mL) and the organic layer dried over MgSO$_4$. After filtration and evaporation, the residue was purified by chromatography with ethyl acetate as eluent to afford 2-(S)-(t-butyloxycarbonylamino)-(methoxycarbonyl)butanoic acid in 75% yield. White solid —R$_f$: 0.50 (Ethyl acetate)-[α]$_D$=+28.6 (c=0.3; CHCl$_3$). IR (cm$^{-1}$): 3429 (N—H), 2979 (C—H), 1714 (C=O), 1509, 1438, 1394, 1367, 1156, 1057, 1026, 843, 780, 734. $^1$H NMR (300 MHz, CDCl$_3$): δ (ppm)=1.42 (s, 9H, CH$_3$), 2.82 (dd, J=4.8, 17.2 Hz, 1H, CH$_2$), 3.02 (dd, J=17.2, 4.1 Hz, 1H, CH$_2$), 3.69 (s, 3H, OCH$_3$), 4.59-4.62 (m, 1H, CHN), 5.57 (d, J=8.5 Hz, 1H, NHBoc), 10.8 (sl, 1H, COOH). $^{13}$C NMR (75 MHz, CDCl$_3$): δ (ppm)=28.2 (CH$_3$), 36.4 (CH$_2$), 49.7 (CHN), 52.1 (OCH$_3$), 80.5 (C(CH$_3$)$_3$), 155.6 (COO), 171.6 (COO), 175.8 (COO). Analysis calculated for C$_{10}$H$_N$NO$_6$ (337.15): C, 48.58; H, 6.93; N, 5.67. found C, 48.64; H, 7.04; N, 5.68.

B.1.3. Synthesis of (S)-2-(t-butyloxycarbonylamino)-4-(methoxycarbonyl)allyl butanoate

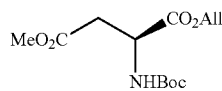

To a solution of 5.62 g (22.7 mmol) of 2-(S)-(t-butyloxycarbonylamino)-(methoxycarbonyl)butanoic acid in 70 mL of DMF, were introduced, under argon, 7.53 g (54.5 mmol) of K$_2$CO$_3$ and 3.9 mL (45.4 mmol) of allyl bromide. After stirring overnight, 70 mL of water were added and the aqueous layer was extracted with 3×75 mL of ethyl acetate. The organic layer was dried over MgSO$_4$ and the solvent evaporated to afford a residue which was purified by chromatography with a mixture of petroleum ether/ethyl acetate (4:1) as eluent. Compound (S)-2-(t-butyloxycarbonylamino)-4-(methoxycarbonyl)allyl butanoate was isolated in 79% yield. Colorless oil —R$_f$: 0.29 (Ethyl acetate/petroleum ether 2:8) [α]$_D$=+17.7 (c=0.7; CHCl$_3$). IR (cm$^{-1}$): 3370 (N—H), 2980 (C—H), 1716 (C=O), 1502, 1439, 1367, 1339, 1286, 1246, 1209, 1161, 1049, 1026, 992. $^1$H NMR (300 MHz, CDCl$_3$): δ (ppm)=1.41 (s, 9H, CH$_3$), 2.79 (dd, J=17.0, 4.7 Hz, 1H, CH$_2$), 2.98 (dd, J=17.1, 4.6 Hz, 1H, CH$_2$), 3.65 (s, 3H, OCH$_3$), 4.53-4.57 (m, 1H, CHN), 4.60 (dt, J=1.3, 5.7 Hz, 2H, OCH$_2$), 5.20 (dq, J=1.2, 10.4 Hz, 1H, CH$_2$=), 5.28 (dq, J=1.4, 17.2 Hz, 1H, CH$_2$=), 5.79-5.92 (m, 1H, CH=). $^{13}$C NMR (75 MHz, CDCl$_3$): δ (ppm)=28.3 (CH$_3$), 36.6 (CH$_2$), 50.0 (CHN), 52.0 (OCH$_3$), 66.2 (OCH$_2$), 80.1 (C(CH$_3$)$_3$), 118.6 (CH$_2$=), 131.5 (CH=), 155.4 (COO), 170.7 (COO), 171.4 (COO). Analysis calculated for C$_{13}$H$_{21}$NO$_6$ (227.14): C, 54.35; H, 7.37; N, 4.88. found C, 54.50; H, 7.38; N, 4.93.

B.1.4. Synthesis of (S)-2-[bis(t-butyloxycarbonyl)amino]-4-(methoxycarbonyl)allyl butanoate

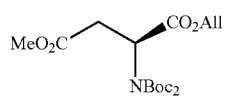

To a solution of 4.86 g (16.9 mmol) of diester (S)-2-(t-butyloxycarbonylamino)-4-(methoxycarbonyl)allyl butanoate in 80 mL of acetonitrile, were added successively under argon, 643 mg (5.2 mmol) of DMAP and 9.3 g (42.6 mmol) of Boc$_2$O. After stirring overnight at room temperature, the solvent was removed under vacuum and the residue was purified by chromatography with a mixture ethyl acetate/petroleum ether (1:4) to afford the diester N,N-diprotected (S)-2-[bis(t-butyloxycarbonyl)amino]-4-(methoxycarbonyl)allyl butanoate in 88% yield. Colorless oil—R$_f$: 0.32 (Ethyl acetate/petroleum ether 1:4)-[α]$_D$=−54.1 (c=0.7; CHCl$_3$). IR (cm$^{-1}$): 2982-2954 (C—H), 1742 (C=O), 1702 (C=O), 1458, 1439, 1368, 1314, 1269, 1243, 1168, 1142, 1116, 993, 934. $^1$H NMR (300 MHz, CDCl$_3$): δ (ppm)=1.47 (s, 18H, CH$_3$), 2.71 (dd, J=16.4, 8.5 Hz, 1H, CH$_2$), 3.23 (dd, J=7.1, 16.4 Hz, 1H, CH$_2$), 3.67 (s, 3H, OCH$_3$), 4.59 (dt, J=1.3, 5.6 Hz, 2H, OCH$_2$), 5.19 (dq, J=1.3, 10.5 Hz, 1H, CH$_2$=), 5.28 (dq, J=1.5, 17.2 Hz, 1H, CH$_2$=), 5.42-5.47 (m, 1H, CHN), 5.79-5.90 (m, 1H, CH=). $^{13}$C NMR (75 MHz, CDCl$_3$): δ (ppm)=27.9 (CH$_3$), 35.6 (CH$_2$), 51.9 (CHN), 55.0 (OCH$_3$), 66.1 (OCH$_2$), 83.5 (C(CH$_3$)$_3$), 118.3 (CH$_2$=), 131.5 (CH=), 151.6 (COO), 169.5 (COO), 171.0 (COO). Analysis calculated for C$_{18}$H$_{28}$NO$_8$ (387.19): C, 55.80; H, 7.54; N, 3.62. found C, 56.16; H, 7.75; N, 3.53.

B.1.5. Synthesis of (S)-2-[bis(t-butyloxycarbonyl)amino]allyl-4-oxobutanoate

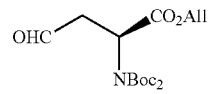

To a solution of 2 g (5.2 mmol) of diester (S)-2-[bis(t-butyloxycarbonyl)amino]-4-(methoxycarbonyl)allyl butanoate in 60 mL of distilled diethyl ether, were introduced under argon, at −78° C., 8.2 mL (8.2 mmol) of DIBAL. The mixture was stirred one hour at −78° C. and hydrolyzed with 10 mL of distilled water at 0° C. After 5 minutes, the mixture was filtered on celite and washed with 3×25 mL of diethyl ether. After removing the solvent, the crude product was dried under vacuum, to afford the aldehyde (S)-2-[bis(t-butyloxycarbonyl)amino]allyl-4-oxobutanoate and traces of the corresponding alcohol. This crude mixture was directly used for the second reduction with NaBH$_4$. Colorless oil —R$_f$: 0.45 (ethyl acetate/petroleum ether 2:8).

B.1.6. Synthesis of (S)-2-[bis(t-butyloxycarbonyl)amino]allyl-4-hydroxybutanoate

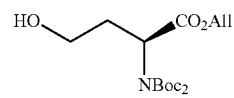

To a solution of 1.83 g (5.1 mmol) aldehyde (S)-2-[bis(t-butyloxycarbonyl)amino]allyl-4-oxobutanoate in 50 mL of a mixture THF/H$_2$O (4:1) under argon, were added 225 mg (5.9 mmol) of NaBH$_4$. The mixture was stirred thirty minutes at 0° C. and the aqueous layer extracted with 3×75 mL of ethyl acetate. The organic layer was dried over MgSO$_4$, filtered and evaporated. The crude product was purified by chromatography with ethyl acetate/petroleum ether (2:8 then 3:7 then 5:5) as eluent, to afford the homoserine derivative (S)-2-[bis(t-butyloxycarbonyl)amino]allyl-4-hydroxybutanoate in 71% yield. Colorless oil —$R_f$: 0.31 (Ethyl acetate/petroleum ester 1:2). $[\alpha]_D$=−27.9 (c=0.7; CHCl$_3$). IR (cm$^{-1}$): 3524 (OH), 2980-2934 (C—H), 1740 (C=O), 1700 (C=O), 1457, 1368, 1272, 1254, 1144, 1119, 1049, 989, 930, 855. $^1$H NMR (300 MHz, CDCl$_3$): δ (ppm)=1.47 (s, 18H, CH$_3$), 1.97-2.07 (m, 1H, CH$_2$), 2.36-2.44 (m, 1H, CH$_2$), 3.54-3.61 (m, 1H, CH$_2$OH), 3.68-3.73 (m, 1H, CH$_2$OH), 4.59 (dt, J=1.4, 5.5 Hz, 2H, OCH$_2$), 4.99 (dd, J=4.7, 9.8 Hz, 1H, CHN), 5.20 (dq, J=1.3, 10.4 Hz, 1H, CH$_2$=), 5.30 (dq, J=1.5, 17.2 Hz, 1H, CH$_2$=), 5.81-5.92 (m, 1H, CH=). $^{13}$C NMR (75 MHz, CDCl$_3$): δ (ppm)=27.9 (CH$_3$), 32.8 (CH$_2$), 55.6 (CHN), 59.0 (CH$_2$OH), 65.8 (OCH$_2$), 83.6 (C(CH$_3$)$_3$), 118.2 (CH$_2$=), 131.7 (CH=), 152.5 (COO), 170.5 (COO). Analysis calculated for C$_{17}$H$_{29}$NO$_4$ (359.19): C, 56.81; H, 8.13; N, 3.90. found C, 56.52; H, 8.32; N, 3.93.

B.1.7. Synthesis of (S)-2-[bis(t-butyloxycarbonyl) amino]allyl-4-iodobutanoate (IIIa)

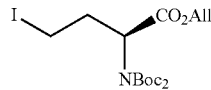

In a flask, containing a solution of 1.33 g (3.7 mmol) of homoserine derivative (S)-2-[bis(t-butyloxycarbonyl)amino] allyl-4-hydroxybutanoate in 20 mL of dry THF, were added 600 mg (8.8 mmol) of imidazole. In a second flask containing 1.52 g (5.8 mmol) of PPh$_3$ in 15 mL of dry THF, were added 1.55 g (6.1 mmol) of iodine. The precedent solution was then added, and the resulting mixture was stirred for two hours at room temperature. The reaction mixture was then hydrolyzed with 100 mL of 20% aqueous NaCl. The aqueous layer was extracted by 3×50 mL of ethyl acetate. After drying over MgSO$_4$, filtration and evaporation, the crude product was purified by chromatography using a mixture of ethyl acetate/petroleum ether (1:9 then 8:2) to afford iodo aminoester (S)-2-[bis(t-butyloxycarbonyl)amino]allyl-4-iodobutanoate (IIIa) in 91% yield. Pale yellow oil —$R_f$: 0.75 (Ethyl acetate/petroleum ether 1:9) $[\alpha]_D$=−44.6 (c=0.7; CHCl$_3$). IR (cm$^{-1}$): 2981-2936 (C—H), 1747 (C=O), 1704 (C=O), 1479, 1457, 1368, 1236, 1171, 1131, 988, 930, 853. $^1$H NMR (300 MHz, CDCl$_3$): δ (ppm)=1.52 (s, 18H, CH$_3$), 2.36-2.48 (m, 1H, CH$_2$), 2.66-2.78 (m, 1H, CH$_2$), 3.16-3.25 (m, 2H, CH$_2$I), 4.63 (dt, J=1.4, 5.5 Hz, 2H, OCH$_2$), 5.03 (dd, J=5.5, 8.5 Hz, 1H, CHN), 5.24 (dq, J=1.3, 10.5 Hz, 1H, CH$_2$=), 5.33 (dq, J=1.5, 17.2 Hz, 1H, CH$_2$=), 5.84-5.97 (m, 1H, CH=). $^{13}$C NMR (75 MHz, CDCl$_3$): δ (ppm)=0.0 (CH$_2$I), 26.2 (CH$_3$), 32.6 (CH$_2$), 52.8 (CHN), 64.1 (OCH$_2$), 87.7 (C(CH$_3$)$_3$), 116.5 (CH$_2$=), 129.8 (CH=), 150.2 (COO), 167.9 (COO). Analysis calculated for C$_{17}$H$_{29}$NO$_6$I (469.10): C, 43.51; H, 6.01; N, 2.98. found C, 43.31; H, 6.24; N, 2.92.

B.1.8. Synthesis of (S)-2-(t-butyloxycarbonylamino) allyl-4-iodobutanoate (III')

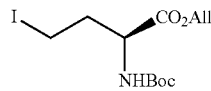

To a solution of 1.6 g (3.4 mmol) of (S)-2-[bis(t-butyloxycarbonyl)amino]allyl-4-iodobutanoate (IIIa) in 20 mL of acetonitrile, were added 1.3 g (3.4 mmol) of CeCl$_3$.7H$_2$O and 513 mg (3.4 mmol) of NaI. The reaction mixture was stirred overnight at room temperature and hydrolyzed with 20 mL of water. The aqueous layer was extracted with 3×20 mL of ethyl acetate and the organic layer was dried over MgSO$_4$. After evaporation, the crude product was purified by chromatography with ethyl acetate/petroleum ether (2:8) as eluent to afford the mono N-protected iodo aminoester (S)-2-(t-butyloxycarbonylamino)allyl-4-iodobutanoate (III') in 86% yield. Pale yellow oil —$R_f$: 0.31 (Ethyl acetate/petroleum ether 1:4) $[\alpha]_b$=+11.7 (c=0.5; CHCl$_3$) IR (cm$^{-1}$): 2981-2936 (C—H), 1747 (C=O), 1704 (C=O), 1479, 1457, 1368, 1236, 1171, 1131, 988, 930, 853. $^1$H NMR (300 MHz, CDCl$_3$): δ (ppm)=1.42 (s, 9H, CH$_3$), 2.10-2.23 (m, 1H, CH$_2$), 2.37-2.43 (m, 1H, CH$_2$) 3.13-3.18 (m, 2H, CH$_2$I) 4.32-4.34 (m, 1H, CHN), 4.62 (d, J=5.8 Hz, 2H, OCH$_2$), 5.05 (d, J=6.2 Hz, 1H, NH), 5.24 (dd, J=1.1, 10.4 Hz, 1H, CH$_2$=), 5.31 (dd, J=1.4, 17.2 Hz, 1H, CH$_2$=), 5.82-5.95 (m, 1H, CH=). $^{13}$C NMR (75 MHz, CDCl$_3$): δ (ppm)=0.0 (CH$_2$I), 28.9 (CH$_3$), 37.8 (CH$_2$), 55.0 (CHN), 66.9 (OCH$_2$), 80.9 (C(CH$_3$)$_3$), 119.8 (CH$_2$=), 132.0 (CH=), 155.9 (COO), 171.9 (COO). Analysis calculated for C$_{12}$H$_{20}$NO$_4$I (369.09): C, 39.04; H, 5.46; N, 3.79. found C, 39.14; H, 5.59; N, 3.84.

B.2. Synthesis of (S)-2-(t-butyloxycarbonylamino) benzyl-4-iodobutanoate (III")

B.2.1. Synthesis of 2-(S)-(t-butyloxycarbonylamino)-4-(methoxycarbonyl)benzyl butanoate diester

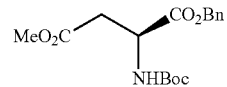

To a solution of 1.42 g (5.7 mmol) of diester 2-(S)-(t-butyloxycarbonylamino)-(methoxycarbonyl)butanoic acid in 50 mL of DMF, were added under argon 1.15 g (8.3 mmol) of K$_2$CO$_3$ and 1.48 mL (12.4 mmol) of benzyl bromide. After stiffing overnight at room temperature, 60 mL H$_2$O were added and the aqueous layer was extracted with 3×75 mL of ethyl acetate. The organic layer was dried over MgSO$_4$ and the solvent removed under vacuum to afford a residue which was purified by chromatography with a mixture petroleum ether/ethyl acetate (4:1) as eluent. The 2-(S)-(t-butyloxycarbonylamino)-4-(methoxycarbonyl)benzyl butanoate diester was isolated in 85% yield. White solid —$R_f$: 0.56 (Ethyl acetate/petroleum ether 1:4). Enantiomeric excess >99%*–$[\alpha]_D$=+4.4 (c=0.5; CHCl$_3$). IR (cm$^{-1}$): 3429 (N—H), 2997-2850 (C—H), 1732 (C=O), 1693 (C=O), 1457, 1388, 1320, 1265, 1240, 1220, 1146, 1130, 1098, 1084, 998, 980, 923, 869, 840, 817, 762, 739. $^1$H NMR (300 MHz, CDCl$_3$): δ (ppm)=1.36 (s, 9H, CH$_3$), 2.75 (dd, J=17.0, 4.7 Hz, 1H, CH$_2$), 2.94 (dd, J=17.1, 4.6 Hz, 1H, CH$_2$), 3.55 (s, 3H, OCH$_3$), 4.51-4.57 (m, 1H, CHN), 5.05-5.16 (m, 2H, OCH$_2$Ph), 5.45 (d, J=8.4 Hz, 1H, NHBoc), 7.24-7.30 (m, 5H, Harom). $^{13}$C NMR (75 MHz, CDCl$_3$): δ (ppm)=28.3 (CH$_3$)$_3$, 36.7 (CH$_2$), 48.1 (CHN), 50.1 (OCH$_3$), 67.4 (OCH$_2$Ph), 80.2 (C(CH$_3$)$_3$), 128.3 (Carom), 128.4 (Carom), 128.6 (Carom), 135.3 (C arom), 170.9 (COO), 171.3 (COO). Mass exact calculated for C$_{17}$H$_{24}$NO$_6$ [M+H]$^+$: 338.1598. found 338.1618. Analysis calculated for C$_{17}$H$_{23}$NO$_6$ (337.15): C, 60.52; H, 6.87; N, 4.15. found C, 60.42; H, 6.95; N, 4.15. The enantiomeric excess was determined by HPLC (Chiralpack AD, hexane: iPrOH 98:2, 1 mL·min$^{-1}$, λ=210 nm, 24° C., $t_R$ (R)=45.8 min, $t_R$ (S)=55.6 min)

B.2.2. Synthesis of 2-(S)-[bis(t-butyloxycarbonyl) amino]-4-(methoxy carbonyl)benzyl butanoate diester

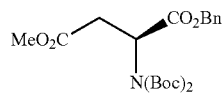

To a solution of 1.60 g (4.7 mmol) of 2-(S)-(t-butyloxycarbonylamino)-4-(methoxycarbonyl)benzyl butanoate diester in 50 mL of acetonitrile, were added successively under argon 185 mg (1.5 mmol) of DMAP and 2.5 g (11.6 mmol) of Boc$_2$O. After stiffing overnight at room temperature, the solvent was removed under vacuum and the residue purified by chromatography with a solvent mixture ethyl acetate/petroleum ether (1:4) to afford the diester 2-(S)-[bis(t-butyloxycarbonyl)amino]-4-(methoxy carbonyl)benzyl butanoate diester in 98% yield. White solid —$R_f$: 0.60 (Ethyl acetate/ petroleum ether 1:4). Enantiomeric excess >99%–$[α]_D$=–40.4 (c=0.2; CHCl$_3$). IR (cm$^{-1}$): 2982 (C—H), 1732 (C=O), 1693 (C=O), 1457, 1388, 1366, 1320, 1265, 1240, 1220, 1146, 1128, 1098, 1014, 998, 980, 923, 869, 840, 817, 762, 739. $^1$H NMR (300 MHz, CDCl$_3$): δ (ppm)=1.47 (s, 18H, CH$_3$), 2.76 (dd, 1H, J=16.5, 6.5 Hz, CH$_2$), 3.30 (dd, 1H, J=16.5, 7.2 Hz, CH$_2$), 3.69 (s, 3H, OCH$_3$), 5.13-5.23 (m, 2H, OCH$_2$Ph), 5.50-5.54 (t, J=6.8 Hz, 1H, CHN), 7.34-7.35 (m, 5H, Harom). $^{13}$C NMR (75 MHz, CDCl$_3$): δ (ppm)=27.9 (CH$_3$), 35.5 (CH$_2$), 51.9 (OCH$_3$), 55.0 (CHN), 67.2 (OCH$_2$Ph), 83.5 (C(CH$_3$)$_3$), 128.1 (C arom), 128.2 (C arom), 128.5 (C arom), 135.3 (C arom), 151.7 (COO), 169.7 (COO), 171 (COO). Mass exact calculated for C$_{22}$H$_{31}$NO$_8$Na [M+Na]$^+$: 460.1942. found 460.1963. Analysis calculated for C$_{22}$H$_{31}$NO$_8$ (437.20): C, 60.40; H, 7.14; N, 3.20. found C, 60.55; H, 7.26; N, 3.23.*The enantiomeric excess was determined by HPLC (Chiralcel OD, hexane:iPrOH 95:5, 0.5 mL·min$^{-1}$, λ=210 nm, 24° C., $t_R$ (R)=76.7 min, $t_R$ (S)=83.1 min)

B.2.3. Synthesis of (S)-2-[bis(t-butyloxycarbonyl)amino]-4-benzyl oxobutanoate ester

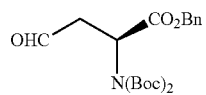

To a solution of 5.57 g (10.8 mmol) of 2-(S)-[bis(t-butyloxycarbonyl)amino]-4-(methoxy carbonyl)benzyl butanoate diester in 100 mL of distilled diethyl ether, were introduced under argon at −78° C. 17.3 mL (17.6 mmol) of DIBAL. The mixture was stirred one hour at −78° C. and hydrolyzed with 17 mL of distilled water at 0° C. After 5 minutes, the mixture was filtered on celite and washed with 3×25 mL of diethyl ether. After removing the solvent the crude product was purified by chromatography with a mixture of ethyl acetate/petroleum ether (1:9 then 1.5:8.5). The aldehyde (S)-2-[bis(t-butyloxycarbonyl)amino]-4-benzyl oxobutanoate ester was isolated in 96% yield. Colorless oil —$R_f$: 0.45 (Ethyl acetate/petroleum ether 2:8). $[α]_D$=–32.0 (c=0.1; CHCl$_3$). IR (cm$^{-1}$): 2982-2936 (C—H), 1741 (C=O), 1703 (C=O), 1457, 1370, 1253, 1146, 1126, 1047, 853, 783, 738, 700. $^1$H NMR (300 MHz, CDCl$_3$): δ (ppm)=1.41 (s, 18H, CH$_3$), 2.80 (ddd, 1H, J=17.4, 6.0, 1.1 Hz, CH$_2$), 3.26 (ddd, 1H, J=17.9, 6.8, 1.1 Hz, CH$_2$), 5.11 (m, 2H, OCH$_2$Ph), 5.55 (t, J=6.4 Hz, 1H, CHN), 7.25-7.29 (m, 5H, Harom), 9.71 (t, 1H, J=1.1 Hz, CHO). $^{13}$C NMR (75 MHz, CDCl$_3$): δ (ppm)=27.9 (CH$_3$), 44.7 (CH$_2$), 53.0 (CHN), 67.4 (OCH$_2$Ph), 83.7 (C(CH$_3$)$_3$), 127.0-129.8 (m, Carom), 135.3 (Carom), 151.7 (COO), 169.7 (COO), 198.5 (CHO). Analysis calculated for C$_{21}$H$_{29}$NO$_7$ (407.46): C, 61.90; H, 7.17; N, 3.44. found C, 62.07; H, 7.46; N, 3.05.

B.2.4. Synthesis of (S)-2-[bis(t-butyloxycarbonyl)amino]-4-hydroxybutanoate benzyl ester

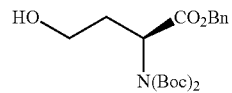

To a solution of 3.62 g (8.9 mmol) of aldehyde (S)-2-[bis(t-butyloxycarbonyl)amino]-4-benzyl oxobutanoate ester in 100 mL of a mixture THF/H$_2$O (4:1) under argon, were added 1.30 g (18.5 mmol) of NaBH$_4$. The mixture was stirred thirty minutes at 0° C. and the aqueous layer extracted with 3×75 mL of ethyl acetate. The organic layer was dried over MgSO$_4$, filtered and evaporated. The crude product was purified by chromatography with a mixture ethyl acetate/petroleum ether (2:8 then 3:7 then 5:5), to afford the homoserine derivative (S)-2-[bis(t-butyloxycarbonyl)amino]-4-hydroxybutanoate benzyl ester in 83% yield. Colorless oil —$R_f$: 0.30 (Ethyl acetate/petroleum ether 3:7). Enantiomeric excess >99%*– $[α]_D$=–19.8 (c=0.6; CHCl$_3$). IR (cm$^{-1}$): 3528 (OH), 2980-2885 (C—H), 1744 (C=O), 1702 (C=O), 1500, 1479, 1457, 1369, 1315, 1274, 1145, 1122, 1047, 904, 853, 783, 750, 698. $^1$H NMR (300 MHz, CDCl$_3$): δ (ppm)=1.46 (s, 18H, CH$_3$), 1.99-2.08 (m, 1H, CH$_2$), 2.40-2.53 (m, 1H, CH$_2$), 3.58-3.63 (m, 1H, CH$_2$OH), 3.72-3.76 (m, 1H, CH$_2$OH), 5.03 (dd, 1H, J=9.7, 4.7 Hz, CHN), 5.14-5.19 (m, 2H, OCH$_2$Ph), 7.26-7.36 (m, 5H, Harom). $^{13}$C NMR (75 MHz, CDCl$_3$): δ (ppm)=27.9 (CH$_3$)$_3$, 32.6 (CH$_2$), 55.7 (CHN), 59.0 (CH$_2$OH), 66.9 (OCH$_2$Ph), 83.6 (C(CH$_3$)$_3$), 127.0-129.8 (m, Carom), 135.6 (Carom), 152.6 (COO), 170.7 (COO). Mass exact calculated for C$_{21}$H$_{31}$NO$_7$Na [M+Na]$^+$: 432.1998. found: 432.2007. Analysis calculated for C$_{21}$H$_{31}$NO$_7$ (409.48): C, 61.60; H, 7.63; N, 3.42. found C, 61.75; H, 7.85; N, 3.35.*The enantiomeric excess was determined by HPLC (Chiralcel OD, hexane:iPrOH 90:10, 0.5 mL·min$^{-1}$), λ=210 nm, 20° C., $t_R$ (R)=16.2 min, $t_R$ (S)=18.4 min).

B.2.5. Synthesis of (S)-2-[bis(t-butyloxycarbonyl)amino]-4-iodobutanoate benzyl ester (IIIb)

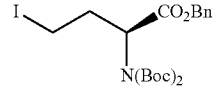

In a flask, containing a solution of 2.71 g (6.6 mmol) of homoserine derivative (S)-2-[bis(t-butyloxycarbonyl)

amino]-4-hydroxybutanoate benzyl ester in 20 mL of dry THF, were added 1.08 g (15.8 mmol) of imidazole. In a second flask containing 3.12 g (11.9 mmol) of PPh$_3$ in 14 mL of dry THF, were added 3.16 g (12.5 mmol) of iodine. The precedent solution was then added, and the resulting mixture was stirred for two hours at room temperature. The reaction mixture was then hydrolyzed with 100 mL of 20% aqueous NaCl. To the aqueous layer was added 3×50 mL of ethyl acetate. After drying over MgSO$_4$, filtration and evaporation of the solvent, the crude product was purified by chromatography using a mixture of ethyl acetate/petroleum ether (1:9 then 8:2) to afford the iodine derivative (S)-2-[bis(t-butyloxycarbonyl)amino]-4-iodobutanoate benzyl ester (Mb) in 91% yield. Pale yellow oil —R$_f$: 0.75 (Ethyl acetate/petroleum ether 1:9). Enantiomeric excess >99%*-[α]$_D$=-41.9 (c=0.6; CHCl$_3$); IR (cm$^{-1}$): 2984-2937 (C—H), 1736 (C=O), 1690 (C=O), 1381, 1366, 1351, 1317, 1264, 1226, 1167, 1150, 1130, 1113, 1056, 976, 955, 896, 866, 851, 831, 789, 763, 752, 722, 700. $^1$H NMR (300 MHz, CDCl$_3$): δ (ppm)=1.46 (s, 18H, CH$_3$), 2.42 (m, 1H, CH$_2$), 2.71 (m, 1H, CH$_2$), 3.16-3.21 (m, 1H, CH$_2$I), 3.27-3.31 (m, 1H, CH$_2$I), 5.04 (dd, 1H, J=8.6, 5.5 Hz), 5.13-5.18 (m, 2H, CH$_2$Ph), 7.37-7.33 (m, 5H, Harom). $^{13}$C NMR (75 MHz, CDCl$_3$): δ (ppm)=0.2 (CH$_2$I), 26.2 (CH$_3$), 32.4 (CH$_2$), 56.8 (CHN), 65.2 (OCH$_2$Ph), 81.7 (C(CH$_3$)$_3$), 126.2-126.9 (m, Carom), 133.6 (Carom), 150.2 (COO), 168.1 (COO). Mass exact calculated for C$_{21}$H$_{31}$NO$_6$NI [M+H]$^+$: 520.1196. found: 520.1202. Analysis calculated for C$_2$H$_{30}$NO$_6$I (519.38): C, 48.56; H, 5.82; N, 2.70. found C 48.61, H 5.89, N 2.89.*The enantiomeric excess was determined by HPLC (Chiralpack AD, hexane: iPrOH 98: 2, 0.5 mL·min$^{-1}$, λ=210 nm, 10° C., t$_R$ (S)=21.7 min, t$_R$ (R)=29.2 min)

B.2.6. Synthesis of (S)-2-(t-butyloxycarbonylamino) benzyl-4-iodobutanoate (III'')

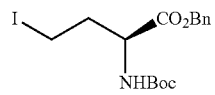

To a solution of 0.80 g (1.9 mmol) of Synthesis of (S)-2-[bis(t-butyloxycarbonyl)amino]-4-iodobutanoate benzyl ester (IIIb) in 20 mL of acetonitrile, were added 0.70 g (1.9 mmol) of CeCl$_3$.7H$_2$O and 0.28 g (1.9 mmol) of NaI. The reaction mixture was stirred overnight at room temperature and hydrolyzed with 10 mL of water. The aqueous layer was extracted with 3×20 mL of ethyl acetate and the organic layer was dried over MgSO$_4$. After evaporation of the solvent, the crude product was purified by chromatography with a mixture of ethyl acetate/petroleum ether (2:8) as eluant to afford the mono N-protected iodo derivative (S)-2-(t-butyloxycarbonylamino)benzyl-4-iodobutanoate (III'') in 86% yield. Pale yellow oil —R$_f$: 0.60 (Ethyl acetate/petroleum ether 2:8); Enantiomeric excess >99%*-[α]$_b$=+4.8 (c=0.4; CHCl$_3$); IR (cm$^-$): 3366 (N—H), 2985 (C—H), 1755 (C=O), 1682 (C=O), 1515, 1453, 1425, 1367, 1349, 1288, 1254, 1225, 1155, 1080, 1047, 1025, 954, 862, 791, 748, 694. $^1$H NMR (300 MHz, CDCl$_3$): δ (ppm)=1.37 (s, 9H, CH$_3$), 2.05-2.18 (m, 1H, CH$_2$), 2.32-2.38 (m, 1H, CH$_2$), 3.04-3.09 (m, 2H, CH$_2$I), 4.30-4.32 (m, 1H, CHN), 5.00-5.16 (m, 3H, OCH$_2$Ph/NH); 7.26-7.31 (m, 5H, Harom). $^{13}$C NMR (75 MHz, CDCl$_3$): δ (ppm)=0.0 (CH$_2$I), 27.0 (CH$_3$), 32.4 (CH$_2$), 55.1 (CHN), 68.2 (OCH$_2$Ph), 81.0 (C(CH$_3$)$_3$), 129.1 (Carom), 129.3 (Carom), 129.4 (Carom), 135.8 (Carom), 156.0 (COO), 172.1 (COO). Mass exact calculated for C$_{21}$H$_{31}$NO$_6$NI [M+Na]±: 442.0486. found 442.0507. Analysis calculated for C$_{16}$H$_{22}$NO$_4$I (419.06): C 45.84, H 5.29, N 3.34. found C, 45.72; H, 5.42; N, 3.47.*The enantiomeric excess was determined by HPLC (Chiralpack AD, hexane:iPrOH 98:2, 0.5 mL min$^{-1}$, λ=210 nm, 10° C., t$_R$ (R)=22.5 min t$_R$ (S)=28.7 min,).

C. Synthesis of Compounds (II')

C.1. Synthesis of allyl 2-[(t-butyloxycarbonyl) amino]-4-(triphenylphosphonium iodure)-butanoate (II'a)

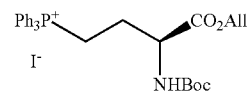

A mixture of 1.1 g (3.1 mmol) of iodo aminoester (S)-2-(t-butyloxycarbonylamino)allyl-4-iodobutanoate (III') and 1.9 g (7.1 mmol) of triphenylphosphine was stirred under argon at 80° C. two hours. Then, 5 mL of toluene followed by 30 mL of diethyl ether were added to the mixture after cooling to room temperature. The white precipitate was washed with 2×25 mL of diethyl ether and purified by chromatography with a mixture of acetone/petroleum ether (7:3) as eluent. The phosphonium salt (II'a) iodo 2-(t-butyloxycarbonyl)amino]-4-triphenyl phosphonium allyl butanoate was isolated in 72% yield. Pale yellow solid —R$_f$: 0.57 (acetone/petroleum ether 7:3)–mp: 84-86° C. Enantiomeric excess=97%-[α]$_b$=-17.5 (c=0.4; CHCl$_3$). IR (cm$^-$): 3249 (NH), 3053-2870 (C—H), 1699 (C=O), 1648 (C=O), 1587, 1508, 1486, 1437, 1391, 1366, 1340, 1309, 1251, 1229, 1158, 1111, 1052, 995, 931, 857, 785, 739, 723, 688, 606. $^1$H NMR (300 MHz, CDCl$_3$): δ (ppm)=1.39 (s, 9H, CH$_3$), 2.26-2.30 (m, 2H, CH$_2$), 3.58-3.73 (m, 1H, CH$_2$P), 3.79-3.95 (m, 1H, CH$_2$P), 4.53-4.60 (m, 3H, OCH$_2$+CHN), 5.15-5.29 (m, 2H, CH$_2$=), 5.78-5.89 (m, 1H, CH=), 6.32 (d, J=7.5 Hz, 1H, NH), 7.65-7.83 (m, 15H, Harom). $^{13}$C NMR (75 MHz, CDCl$_3$): δ (ppm)=20.3 (d, J=53.6 Hz, CH$_2$P), 23.8 (CH$_2$), 28.3 (CH$_3$), 53.2 (d, J=17.3 Hz, CHN), 66.2 (OCH$_2$), 80.0 (C(CH$_3$)$_3$), 117.8 (d, J=86 Hz, Carom), 118.6 (CH$_2$=), 130.6 (d, J=12.8 Hz, Carom), 131.7 (CH=), 133.6 (d, J=9.8 Hz, Carom), 135.2 (d, J=3 Hz, Carom), 135.7 (COO), 170.7 (COO). $^{31}$P NMR (121 MHz, CDCl$_3$): δ (ppm)=+25.2 (s). Mass exact calculated for C$_{30}$H$_{35}$N$_1$O$_4$P$_1$ [M-I]$^+$: 504.2298. found: 504.2278.

C.2. Synthesis of allyl 2-[(t-butyloxycarbonyl) amino]-4-[tri-(4-trifluoromethyl phenyl)-(phosphonium iodure)]-butanoate (II'b)

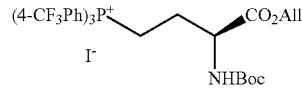

A mixture of 0.23 g (0.6 mmol) of iodo aminoester (S)-2-(t-butyloxycarbonylamino)allyl-4-iodobutanoate (III') and 0.56 g (1.2 mmol) of [tri-(4-trifluoromethylphenyl)]phosphine was stirred under argon at 80° C. three hours. Then, 3 mL of toluene followed by 30 mL of diethyl ether were added to the mixture after cooling to room temperature. The white precipitate was washed with 2×25 mL of diethyl ether and purified by chromatography with a mixture of acetone/petroleum ether (2:7) as eluent. The phosphonium salt (II'b) was isolated in 39% yield. $^{31}$P NMR (121 MHz, CDCl$_3$): δ (ppm)=+27 (s).

C.3. Synthesis of allyl 2-[(t-butyloxycarbonyl)amino]-4-[tri-(4-methoxyphenyl)-(phosphonium iodide)]-butanoate (II'c)

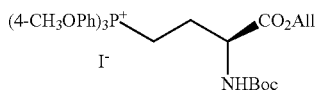

A mixture of 0.23 g (0.6 mmol) of iodo aminoester (S)-2-(t-butyloxycarbonylamino)allyl-4-iodobutanoate (III') and 0.42 g (1.2 mmol) of [tri-(4-methoxyphenyl)]phosphine in 0.5 mL of dry THF was stirred under argon at 80° C. After three hours, 3 mL of toluene followed by 30 mL of diethyl ether were added to the mixture at room temperature. The white precipitate was washed with 2×25 mL of diethyl ether and purified by chromatography with a mixture of acetone/petroleum ether (3:7) as eluent. The phosphonium salt (We) was isolated in 70% yield. Pale yellow solid $^{31}$P NMR (121 MHz, CDCl$_3$): δ (ppm)=+21 (s).

C.4. Synthesis of allyl 2-[(t-butyloxycarbonyl)amino]-4-[tri-(4-fluorophenyl)-phosphonium iodide]-butanoate (II'd)

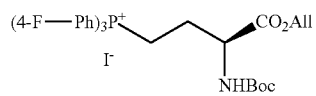

A mixture of 0.28 g (0.76 mmol) of iodo aminoester (S)-2-(t-butyloxycarbonylamino)allyl-4-iodobutanoate (III') and 0.48 g (1.5 mmol) of [tri-(4-fluorophenyl)]phosphine in THF was stirred 24 h under argon at 80° C. Then, 3 mL of toluene followed by 30 mL of diethyl ether were added to the mixture at room temperature. The white precipitate was filtered off and washed with 2×25 mL of diethyl ether and purified by chromatography with a mixture of acetone/petroleum ether (2:7) as eluent. The phosphonium salt (II'd) was isolated in 63% yield. Pale yellow solid. $^{31}$P NMR (121 MHz, CDCl$_3$): δ (ppm)=+26 (s).

C.5. Synthesis of allyl 2-[bis(t-butyloxycarbonyl)amino]-4-(tricyclohexyl phosphonium iodide)-butanoate (II'e)

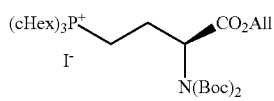

A mixture of 0.20 g (0.43 mmol) of iodo aminoester (Ma) and 0.24 g (0.85 mmol) of tricyclohexylphosphine was stirred under argon in a mixture of acetonitrile/THF (1:2). After 5 days stirring, 5 mL of toluene were added followed by 30 mL of diethyl ether. The white precipitate was filtered off and washed with 2×25 mL of diethyl ether to afford the phosphonium salt (II'e) in 79% yield. $^1$H NMR (300 MHz, CDCl$_3$): δ (ppm)=1.22-2.2 (m, 50H, CH$_2$, cHex, Boc), 2.4-2.6 (m, 2H, P$^+$CH$_2$), 2.7-2.9 (m, 3H, P+CH), 4.65 (d, J=6 Hz, 2H, OCH$_2$), 4.94 (t, J=7 Hz, 1H, CHN), 5.27 (d, J=11 Hz, 1H, CH(H)=), 5.34 (d, J=17 Hz, 1H, C(H)H=), 5.92 (m, 1H, —CH=). $^{31}$P NMR (121 MHz, CDCl$_3$): δ (ppm)=+32.5 (s).

C.6. Synthesis of allyl 2-[bis(t-butyloxycarbonyl)amino]-4-(triphenylphosphonium iodide)-butanoate (II'f)

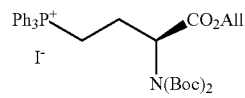

A mixture of 0.12 g (0.26 mmol) of iodo aminoester (Ma) and 0.17 g (0.65 mmol) of triphenylphosphine was stirred under argon at 55° C. After 16 h stiffing at this temperature, the residue was purified by chromatography with a mixture of ethyl acetate/petroleum ether (7:3) as eluent. The phosphonium salt (II'f) was then obtained in 66% yield. Pale yellow solid —R$_f$: 0.50 (Ethyl acetate/petroleum ether 7:3). Enantiomeric excess >99%. $^1$H NMR (300 MHz, CDCl$_3$): δ (ppm)=1.48 (s, 18H, CH$_3$), 2.18 (m, 1H, CH(H)), 2.6 (m, 1H, C(H)H), 3.5-3.75 (m, 1H, CH$_2$P), 3.8-3.95 (m, 1H, CH$_2$P), 4.62 (d, 2H, CH$_2$O), 5.15 (t, J=6 Hz, 1H, CHN), 5.21-5.34 (2d, 2H, CH$_2$=), 5.83-5.93 (m, 1H, —CH=) .7.71-7.88 (m, 15H, Harom). $^{31}$P NMR (121 MHz, CDCl$_3$): δ (ppm)=+24.1 (s). Mass exact calculated for C$_{35}$H$_{43}$NO$_6$PI [M-I]: 604.2855. found 604.2813.

C.7. Synthesis of benzyl[2-(t-butyloxycarbonyl)amino]-4-(triphenylphosphonium iodure)-butanoate (II'g)

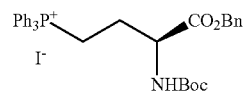

A mixture of 0.60 g (1.4 mmol) of iodo aminoester (III") and 1.0 g (4 mmol) of triphenylphosphine was stirred under argon at 80° C. for two hours. Then, 5 mL of toluene followed by 30 mL of diethyl ether were added to the mixture after cooling to room temperature. The white precipitate was washed with 2×25 mL of diethyl ether and purified by chromatography with a mixture of acetone/petroleum ether (7:3) as eluent. The phosphonium salt (II'g) was then obtained in 70% yield. Enantiomeric excess=97%–[α]$_D$=−15.8 (c=0.3; CHCl$_3$). IR (cm$^{-1}$): 3243 (NH), 3057 (C=CH), 2977-2931 (CH$_2$, CH$_3$), 1737 (COO), 1699 (COO), 1500, 1437, 1365, 1158, 1111, 996, 738, 723, 688. $^1$H NMR (300 MHz, CDCl$_3$): δ (ppm)=1.30 (s, 9H, CH$_3$), 2.16-2.28 (m, 2H, CH$_2$), 3.54-3.75 (m, 1H, CH$_2$P), 3.81-3.89 (m, 1H, CH$_2$P), 4.53-4.55 (m, 1H, CHN), 5.09 (sl, 2H, OCH$_2$Ph), 6.28 (d, J=6.5 Hz, 1H, NH), 7.20-7.26 (m, 5H, Harom), 7.59-7.73 (m, 15H, Harom). $^{13}$C NMR (75 MHz, CDCl$_3$): δ (ppm)=20.4 (d, J=53.1 Hz, CH$_2$P), 24.0 (CH$_2$), 28.0 (CH$_3$), 53.3 (d, J=16.8 Hz, CHN), 67.4 (OCH$_2$Ph), 80.0 (C(CH$_3$)$_3$), 117.8 (d, J=86.6 Hz, Carom), 128.2 (Carom), 128.5 (Carom), 130.6 (d, J=12.6 Hz, Carom), 133.6 (d, J=10.0 Hz, Carom), 135.2 (d, J=2.9 Hz, Carom), 135.4 (Carom), 155.7 (COO); 170.9 (COO). $^{31}$P NMR (121 MHz, CDCl$_3$): δ (ppm)=+24.7 (s). Mass exact calculated for C$_{34}$H$_{37}$NO$_4$PI [M-I]: 554.2455. found 554.2461. Analysis calculated for C$_{34}$H$_{37}$NO$_{4I\ I}$ (681.67): C 59.92, H 5.47 N 2.06. found C 59.20, H 5.68, N 2.05.

D. Synthesis of Compounds (II"a)

D.1. Synthesis of 2-[(t-butyloxycarbonyl)amino]-4-(triphenylphosphonium iodide)-butanoic acid (II"a)

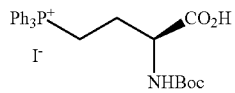

To a solution of 1.28 g (2 mmol) of phosphonium salt (II'a) in 20 mL of dry THF, were successively added under argon at room temperature 46 mg (0.05 mmol) of Pd$_2$ dba$_3$ and 40 mg (0.1 mmol) of dppe. After five minutes stiffing 0.42 mL (4.2 mmol) of HNEt$_2$ was introduced and the mixture was stirred at room temperature overnight. After hydrolysis, extraction with dichloromethane, the combined organic layers were dried over MgSO$_4$, evaporated under vacuum and purified by chromatography with a mixture of acetone/methanol (1:1) as eluent to afford the phosphonium salt (II"a) in 80% yield. White solid —R$_f$: 0.50 (acetone/MeOH 1:1)–mp=152° C. Enantiomeric excess=97%–[α]$_D$=+48.5 (c=0.4; CHCl$_3$); IR (cm$^{-1}$): 3387 (NH), 3060-2932 (C—H), 1695 (C=O), 1605 (C=O), 1483, 1438, 1386, 1365, 1251, 1161, 1112, 1053, 1025, 997, 859, 830, 781, 739, 723, 689, 609. $^1$H NMR (300 MHz, CDCl$_3$): δ (ppm)=1.33 (s, 9H, CH$_3$), 2.13-2.32 (m, 2H, CH$_2$), 3.13-3.30 (m, 2H, CH$_2$P), 4.08 (t, J=3.6 Hz, 1H, CHN), 6.27 (dl, J=2.7 Hz, 1H, NH), 7.52-7.64 (m, 12H, Harom), 7.70-7.77 (m, 3H, Harom). $^{13}$C NMR (75 MHz, CDCl$_3$): δ (ppm)=18.4 (d, J=9.8 Hz, CH$_2$P), 25.7 (CH$_2$), 28.4 (CH$_3$)$_3$, 54.9 (d, J=17.3 Hz, CHN), 78.6 (C(CH$_3$)$_3$), 118.3 (d, J=86 Hz, Carom), 130.5 (d, J=12.8 Hz, Carom), 133.3 (d, J=9.8 Hz, Carom), 135.1 (d, J=3 Hz, Carom), 156 (COO), 172.6 (COO). $^{31}$P NMR (121 MHz, CDCl$_3$): δ (ppm)=+24.3 (s). Mass exact calculated for C$_{27}$H$_{31}$N$_1$O$_4$P$_1$ [M-I]$^+$: 464.1985. found: 464.1963.

D.2. Synthesis of 2-[(t-butyloxycarbonyl)amino]-4-[tri-(4-methoxyphenyl)-phosphonium iodide]-butanoic acid (II"c)

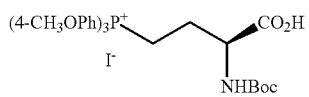

To a solution of 0.2 g (0.3 mmol) of phosphonium salt (We) in 2 mL of dry THF were introduced successively under argon at room temperature, 6 mg (0.006 mmol) of Pd$_2$ dba$_3$ and 5 mg (0.013 mmol) of dppe. After five minutes stirring, 0.13 mL (1.2 mmol) of HNEt$_2$ was added and the solution was stirred during 16 hours at room temperature. The solvent was evaporated and the residue was purified by chromatographic column with acetone then a mixture of acetone/methanol (1:1) as eluent to afford the phosphonium salt (II"c) with 50% yield. $^{31}$P NMR (121 MHz, CDCl$_3$): δ (ppm)=+21 (s).

D.3. Synthesis of 2-[(t-butyloxycarbonyl)amino]-4-[tri-(4-fluorophenyl)-phosphonium iodide]-butanoic acid (II"d)

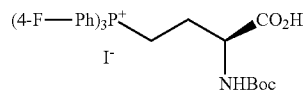

To a solution of 0.33 g (0.47 mmol) of phosphonium salt (II'd) in 4 mL of dry THF were introduced successively under argon at room temperature, 10 mg (0.011 mmol) of Pd$_2$ dba$_3$ and 9 mg (0.022 mmol) of dppe. After two hours stiffing, 0.17 mL (1.6 mmol) of HNEt$_2$ was added and the solution was stirred during 16 hours at room temperature. The solvent was evaporated and the residue was purified by chromatographic column using acetone then a mixture of acetone/methanol (1:1) as eluent to afford the phosphonium salt (II"d) with 50% yield. $^{31}$P NMR (121 MHz, CDCl$_3$): δ (ppm)=+26 (s).

D.4. Synthesis of 2-[bis(t-butyloxycarbonyl)amino]-4-(tricyclohexyl phosphonium iodide)-butanoïc acid (II"e)

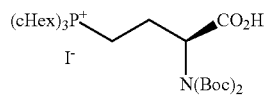

To a solution of 0.11 g (0.15 mmol) phosphonium salt (II'e) in 3 mL of dry THF, were successively added under argon, at room temperature 3.4 mg (0.004 mmol) of Pd$_2$ dba$_3$ and 3 mg (0.007 mmol) of dppe. After five minutes stiffing, 0.031 mL (0.3 mmol) of HNEt$_2$ was introduced and the stiffing was maintained 16 hours at room temperature. After hydrolysis, extraction with dichloromethane, the combined organic layers were dried over MgSO$_4$, evaporated under vacuum and purified by chromatography with a mixture of acetone/methanol (1:1) as eluent to afford the phosphonium salt (Ire) in 50% yield. $^{31}$P NMR (121 MHz, CDCl$_3$): δ (ppm)=+32 (s).

D.5. Synthesis of 2-[bis(t-butyloxycarbonyl)amino]-4-(triphenylphosphonium iodide)-butanok acid (II"f)

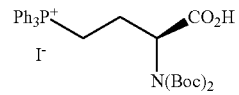

To a solution of 0.65 mg (0.9 mmol) of phosphonium salt (III) in 2 mL of dry THF, were successively added under argon, at room temperature 4.6 mg (0.0025 mmol) of Pd$_2$ dba$_3$ and 1.9 mg (0.005 mmol) of dppe. After five minutes stiffing 0.022 mL (0.21 mmol) of HNEt$_2$ was introduced and the stirring was maintained for 16 hours at room temperature. After hydrolysis, extraction with dichloromethane, the combined organic layers were dried over MgSO$_4$, evaporated under vacuum and purified by chromatography with a mixture of acetone/methanol (1:1) as eluent to afford the phosphonium salt (II'f) in 80% yield. $^{31}$P NMR (121 MHz, CDCl$_3$): δ (ppm)=+24 (s).

E. Synthesis of Compounds (I')

E.1 Synthesis of (S)-allyl-2-(t-butyloxycarbonylamino)-5-phenylpent-4-enoate (I' a)

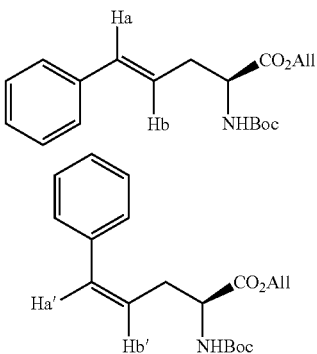

To a solution of 140 mg (0.2 mmol) of phosphonium (II'a) in chlorobenzene (1.5 mL) were added successively 31 mg of benzaldehyde (0.3 mmol, 1.5 eq.) and Cs$_2$CO$_3$ (370 mg, 1.2 mmol, 6 eq.). The reaction mixture was stirred 16 hours at 50° C., hydrolyzed with distilled water (5 mL) and extracted with ethyl acetate (3×5 mL). The organic layers were dried over magnesium sulfate, and the solvent evaporated under vacuum. The crude product was then purified by chromatography on silica with a mixture of ethyl acetate/petroleum ether (1:9 then 1:4) as eluent to afford the corresponding amino ester (I' a) in 83% yield in a ratio cis/trans=88:12. Colorless oil. Enantiomeric excess=83%*. $^1$H NMR (300 MHz, CDCl$_3$): δ (ppm)=1.45-1.48 (2s, 18H, CH$_3$), 2.87-3.20 (m, 2H, CH$_2$), 5.12-5.18 (m, 1H, CHN), 5.63-5.72 (m, 0.12H, CH=cis), 6.13-6.24 (m, 0.88H, CH=trans), 6.45 (d, J=15.8 Hz, 0.88H, CH=trans), 6.58 (d, J=11.6 Hz, 0.12H, CH=cis), 7.18-7.37 (m, 5H, Harom), 10.7 (sl, 1H, COOH).*The enantiomeric purity was determined by HPLC (Lux 5u cellulose-2, hexane:iPrOH 98:2, 0.7 mL·min$^{-1}$, λ=254 nm, 20° C.

F. Synthesis of Compounds (I″)

F.1. Use of Cs$_2$CO$_3$ as Weak Base

F.1.1.(S)-2-[Bis(t-butyloxycarbonyl)amino]-5-phenylpent-4-enoïc acid

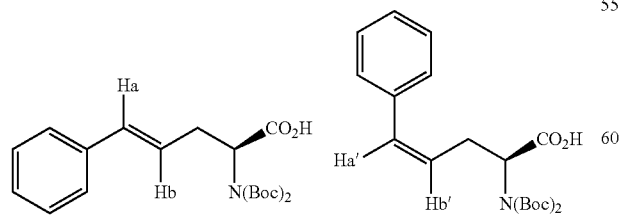

To a solution of 300 mg (0.43 mmol) of phosphonium (II″f) in chlorobenzene (2.5 mL) were added successively 68 mg of benzaldehyde (0.65 mmol, 1.5 eq.) and Cs$_2$CO$_3$ (706 mg, 2.2 mmol). The reaction mixture was stirred 16 hours at 50° C., hydrolyzed with distilled water (5 mL) and extracted with ethyl acetate (3×5 mL). The aqueous layer was acidified with a solution of KHSO$_4$ (1M) until pH=3, and extracted with ethyl acetate (3×5 mL). The organic layers were dried over magnesium sulfate, and the solvent evaporated under vacuum. The crude product was then purified by chromatography on silica with a mixture of ethyl acetate/petroleum ether (1:1)+1% acetic acid as eluent to afford the corresponding amino acid in 87% yield. Colorless oil. Enantiomeric excess >99%. $^1$H NMR (300 MHz, CDCl$_3$): δ (ppm)=1.53 (s, 9H, CH$_3$), 2.64-2.95 (m, 2H, CH$_2$), 4.42-4.49 (m, 1H, CHN), 4.60-4.62 (m, 2H, OCH$_2$), 5.10-5.12 (m, 1H, NH), 5.22-5.37 (m, 2H, CH$_2$=), 5.47-5.56 (m, 0.85H, CH=CH=cis), 5.80-5.99 (m, 1.15H, CH=+CH=CH=trans), 6.41 (d, J=15.8 Hz, 0.15H, CH=CH=trans), 6.53 (d, J=11.6 Hz, 0.85H, CH=CH=cis), 7.18-7.32 (m, 5H, Harom).

F.2. Use of K$_3$PO$_4$ as Weak Base

General Procedure

To a solution of 120 mg (0.2 mmol) of phosphonium (II″a) in chlorobenzene (1.5 mL) were added successively aldehyde (0.4 mmol, 2 eq.), and K$_3$PO$_4$ (254 mg, 1.2 mmol, 6 eq.). The reaction mixture was stirred 16 hours at 90° C., hydrolyzed with distilled water (5 mL) and extracted with diethyl ether (3×5 mL). The aqueous layer was acidified with a solution of KHSO$_4$ (1M) until pH=3, and extracted with ethyl acetate (3×5 mL). The organic layers were dried over magnesium sulfate, and the solvent evaporated under vacuum. The crude product was then purified by chromatography on silica with a mixture of ethyl acetate/petroleum ether (3:7) with 1% acetic acid as eluent to afford the corresponding amino acid (I″).

TABLE 1

Wittig reactions of the phosphonium salt (II″a) with various aldehydes RCHO

| entry | RCHO | γ, δ-in-saturated amino acids (I″) | Yield (%)$^a$ | cis/trans (%) |
|---|---|---|---|---|
| 1 | PhCHO | (I″a) | 72 | 30:70 |
| 2 | 4-CF$_3$-C$_6$H$_4$-CHO | (I″b) | 98 | 10:90 |
| 3 | 4-O$_2$N-C$_6$H$_4$-CHO | (I″c) | 75 | 15:85 |
| 4 | 4-NC-C$_6$H$_4$-CHO | (I″d) | 96 | 20:80 |

TABLE 1-continued

Wittig reactions of the phosphonium salt (II″a) with various aldehydes RCHO

| entry | RCHO | γ, δ-in-saturated amino acids (I″) | Yield (%)[a] | cis/trans (%) |
|---|---|---|---|---|
| 5 | 4-MeO-C6H4-CHO | (I″e) | 67 | 24:76 |
| 6 | 3,4-(MeO)2-C6H3-CHO | (I″f) | 76 | 20:80 |
| 7 | 2-furyl-CHO | (I″g) | 80 | —[b] |
| 8 | PhCH2CH2-CHO | (I″h) | 57 | —[b] |
| 9 | (CH2O)n | (I″i) | 55 | —[b] |
| 10 | PhCH2-CHO | (I″j) | 10 | —[b] |
| 11 | 4-(pinacolboronate)-C6H4-CHO | (I″k) | 57 | 25:75 |
| 12 | calix[4]arene-CHO (tetrapropoxy) | (I″l) | 25 | —[b] |
| 13 | ferrocene-CHO | (I″m) | 51[c] | 50:50 |
| 14 | 1,3-(OHC)2-C6H4 | (I″n) | 85 | —[b] |
| 15 | PhCH=CH-CHO (cinnamaldehyde) | (I″o) | 77 | —[b] |
| 16 | 4-N3-C6H4-CH=CH-CHO | (I″p) | 57 | —[b] |
| 17 | EtO2C-CH=CH-CHO | (I″q) | 58 | —[b] |
| 18 | (CH3)2C=CH-CHO | (I″r) | 70 | —[b] |
| 19 | 4-O2N-C6H4-CH=CH-CHO | (I″s) | 70 | —[b] |
| 20 | 2-thienyl-CH=CH-CHO | (I″t) | 80 | —[b] |
| 21 | 2-furyl-CH=CH-CHO | (I″u) | 73 | —[b] |

[a] isolated yield, e.e. > 98%.
[b] ratio not determined.
[c] isolated as methyl ester product F2.1. (S)-2-(t-butyloxycarbonylamino)-5-phenyl-pent-4-enoïc acid (I″a)

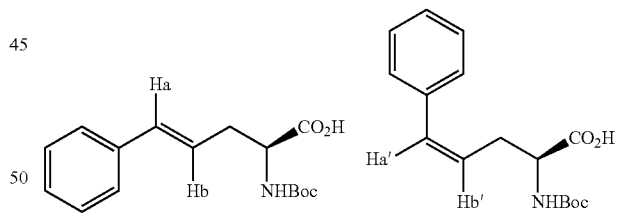

120 mg of phosphonium salt (II″a) and 42.4 mg of benzaldehyde were used to afford the unsaturated amino acid (I″a) in 72% yield in a ratio cis/trans=30:70. Pale yellow oil —$R_f$: 0.52 (Ethyl acetate/petroleum ether 3:7+1% acetic acid). Enantiomeric excess >98%*–$[\alpha]_D$=+21.5 (c=0.6; CHCl3). IR (cm$^{-}$): 3422 (N—H), 3026-2930 (CH2, CH3), 1711 (C=O), 1496, 1450, 1395, 1368, 1249, 1163, 1053, 1026, 966, 910, 853, 774, 735, 694, 648, 609. $^1$H NMR (300 MHz, CDCl3): δ (ppm)=1.45 (s, 9H, CH3), 2.65-2.81 (m, 1.4H, CH2 trans), 2.92-2.98 (m, 0.6H, CH2 cis), 4.28-4.38 (m, 0.3H, CHN cis), 4.49-4.51 (m, 0.7H, CHN trans), 5.05 (d, J=8.1 Hz, 0.3H, NH cis), 5.12 (d, J=7.8 Hz, 0.7H, NH trans), 5.60-5.69 (m, 0.3H, Hb'), 6.08-6.23 (m, 0.7H, Hb), 6.5 (d, J=15.9 Hz, 0.7H, Ha), 6.63 (d, J=11.7 Hz, 0.3H, Ha'), 7.22-7.38 (m, 5H, Harom). $^{13}$C NMR (75 MHz, CDCl$_3$): δ (ppm)=28.3 (CH$_3$), 31.1 (CH$_2$ cis), 35.8 (CH$_2$ trans), 53.1 (CHN), 80.2 (C(CH$_3$)$_3$ trans), 80.4 (C(CH$_3$)$_3$ cis), 123.5 (CH=), 125.6 (CH=), 126.3 (Carom), 126.4 (Carom), 127.1 (Carom), 127.6 (Carom), 128.3 (Carom), 128.4 (Carom), 128.5 (Carom), 128.6 (Carom), 128.7 (Carom), 129.7 (Carom), 130.2 (Carom), 132.8 (CH=), 134.2 (CH=), 136.8 (Carom), 155.6 (COO), 176.5 (COO). Mass exact calculated for C$_{16}$H$_{21}$N$_1$Na$_1$O$_4$ [M+Na]$^+$: 314.1363. found 314.1343.*The enantiomeric purity was determined by HPLC after esterification with TMSCHN$_2$ (Lux 5 μm cellulose-2, hexane:iPrOH 98:2, 1.3 mL min$^{-1}$, λ=210 nm, 20° C., t$_R$ (cis (S))=13.1 min, t$_R$ (trans (S))=16.5 min, t$_R$ (cis (R))=23.3 min, t$_R$ (trans (R))=32.2 min)

F2.2. (S)-2-(t-bityloxycarbonylamino)-5-[4-trifluoromethyl)phenyl]pent-4-enoïc acid (I"b)

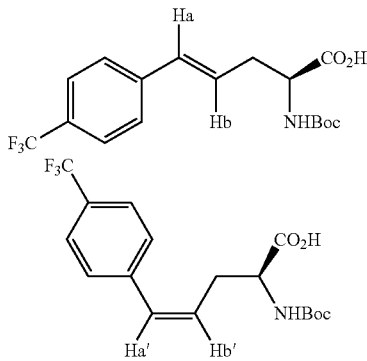

120 mg of phosphonium salt (II"a) and 69.6 mg of 4-trifluoromethylbenzaldehyde were used to synthesize the unsaturated amino acid (I"b) in 98% yield in a ratio cis/trans=10:90. White solid —R$_f$:0.33 (Ethyl acetate/petroleum ether 3:7+1% acetic acid). Enantiomeric excess >98%*−[α]$_D$=+40.9 (c=0.6; CHCl$_3$). IR (cm$^{-1}$): 3352 (N—H), 2973-2925 (C—H), 1710 (C=O), 1681 (C=O), 1615, 1521, 1433, 1415, 1392, 1367, 1326 (CF$_3$), 1287, 1267, 1252, 1159, 1108, 1084, 1069, 1046, 1025, 1016, 973, 951, 853, 834, 812, 779, 752, 693. $^1$H NMR (300 MHz, CDCl$_3$): δ (ppm)=1.44 (s, 9H, CH$_3$), 2.68-2.70 (m, 1H, CH$_2$), 2.76-2.80 (m, 1H, CH$_2$), 4.21-4.23 (m, 0.1H, CHN cis), 4.30-4.52 (m, 0.89 H CHN trans), 5.17 (d, J=7.8 Hz, 0.9H, NH trans), 5.71-5.88 (m, 0.1H, Hb'), 6.22-6.27 (m, 0.9H, Hb), 6.52 (d, J=15.6 Hz, 0.9H, Ha), 6.62 (d, J=11.4 Hz, 0.1H, Ha'), 7.35 (d, J=7.8 Hz, 0.2H, NH cis), 7.43 (d, J=8.1 Hz, 2H, Harom), 7.53-7.58 (m, 2H, Harom). $^{13}$C NMR (75 MHz, CDCl$_3$): δ (ppm)=27.2 (CH$_2$ cis ou trans), 28.2 (CH$_3$), 34.3 (CH$_2$ cis or trans), 53.0 (CHN cis or trans), 54.4 (CHN cis or trans), 80.6 (C(CH$_3$)$_3$ cis or trans), 82.1 (C(CH$_3$)$_3$ cis or trans), 125.3 (q, J=271.7 Hz, CF$_3$), 125.3 (q, J=6.8 Hz, Carom), 126.4 (Carom), 126.6 (Carom), 127.7 (CH=cis or trans), 128.2 (Carom), 128.6 (CH=), 128.8 (q, J=31.7 Hz, Carom), 129.5 (CH=cis or trans), 129.6 (CH=cis or trans), 132.8 (Carom). Mass exact calculated for C$_{17}$H$_{19}$F$_3$N$_2$Na$_1$O$_4$ [M+H]$^+$: 358.1272. found 358.1256. The enantiomeric purity was determined by HPLC on chiral column after esterification with TMSCHN$_2$ (Lux 5 μm cellulose-2, hexane:iPrOH 95:5, 1 mL·min$^{-1}$, λ=210 nm, 20° C., t$_R$ (cis (S))=6.9 min, t$_R$ (trans (S))=8.2 min, t$_R$ (cis (R))=10.6 min, t$_R$ (trans (R))=17.2 min)

F2.3. (S)-2-(t-butyloxycarbonylamino)-5-(4-nitrophenyl)pent-4-enoïc acid (I"c)

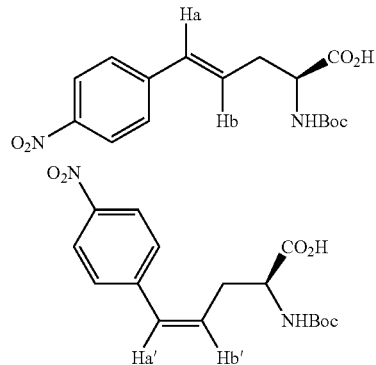

120 mg of phosphonium (II"a) and 60.4 mg of 4-nitrobenzaldehyde were used to afford the unsaturated amino acid (I"c) in 75% yield in a ratio cis/trans=15:85. Orange oil —R$_f$: 0.33 (Ethyl acetate/petroleum ether 3:7+1% acetic acid). Enantiomeric excess >98%*[α]$_D$=+33.8 (c=0.6; CHCl$_3$). IR (cm$^-$): 3487 (N—H), 3059-2817 (C—H), 1703 (C=O), 1484, 1453, 1436, 1413, 1386, (N—O), 1366 (N—O), 1311, 1220, 1167, 1107, 1064, 1024, 1002, 954, 883, 823, 742, 698. $^1$H NMR (300 MHz, CDCl$_3$): δ (ppm)=1.43 (s, 9H, CH$_3$), 2.65-2.78 (m, 1H, CH$_2$), 2.83-2.89 (m, 1H, CH$_2$), 4.54-4.56 (m, 1H, CHN), 5.2 (m, d, J=7.8 Hz, 0.85H, NH trans), 5.78-5.82 (m, 0.15H, Hb'), 6.30-6.54 (m, 0.85H, Hb), 6.56 (d, J=15.6 Hz, 0.85H, Ha), 6.68 (d, J=11.4 Hz, 0.15H, Ha'), 7.16 (d, J=7.8 Hz, 0.15H, NH cis), 7.46 (d, J=8.8 Hz, 2H, Harom), 8.14 (d, J=8.4 Hz, 2H, Harom). $^{13}$C NMR (75 MHz, CDCl$_3$): δ (ppm)=27.2 (CH$_3$), 28.7 (CH$_2$ cis), 35.1 (CH$_2$ trans), 51.9 (CHN trans), 53.2 (CHN cis), 79.6 (C(CH$_3$)$_3$ trans), 81.3 (C(CH$_3$)$_3$ cis), 122.6 (Carom cis), 122.9 (Carom trans), 125.8 (Carom trans), 128 (CH=trans), 129.8 (CH=cis), 130.2 (Carom cis), 131.1 (CH=trans), 133.8 (CH=cis), 142.2 (Carom trans), 145.6 (Carom cis), 145.9 (Carom trans), 149.9 (Carom cis), 154.4 (COO), 155.8 (COO), 174.9 (COO), 175.3 (COO). Mass exact calculated for C$_{16}$H$_{20}$N$_2$NaO$_6$ [M+Na]$^+$: 359.1214. found 359.1228. The enantiomeric purity was determined by HPLC after esterification with TMSCHN$_2$ (Lux 5 μm cellulose-2, hexane:iPrOH 90:10, 1 mL·min$^{-1}$, λ=210 nm, 20° C., t$_R$ (cis (S))=16.2 min, t$_R$ (trans (S))=20.4 min, t$_R$ (cis (R))=22.1 min, t$_R$ (trans (R))=34.2 min)

F2.4. (S)-2-(t-butyloxycarbonylamino)-5-(4-cyanophenyl)pent-4-enoïc acid (I"d)

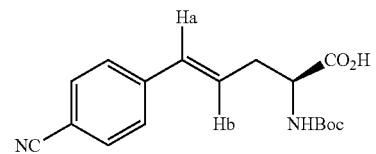

-continued

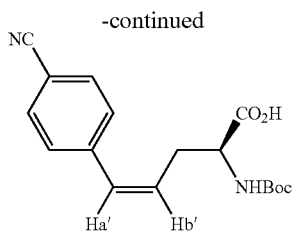

120 mg of phosphonium salt (II″a) and 52 mg of 4-cyanobenzaldehyde were used to synthesize the unsaturated amino acid (I″d) in 96% yield in a ratio cis/trans=20:80. White solid —$R_f$: 0.31 (Ethyl acetate/petroleum ether 3:7+1% acetic acid). Enantiomeric excess >98%*-$[\alpha]_D$=-21.5 (c=0.3; CHCl$_3$). IR (cm$^-$): 3416 (N—H), 3135-2865 (C—H), 2221 (CN), 1737 (C=O), 1662 (C=O), 1604, 1522, 1457, 1442, 1412, 1396, 1371, 1334, 1305, 1252, 1210, 1157, 1442, 1412, 1396, 1371, 1334, 1305, 1252, 1210, 1086, 1027, 974, 969, 951, 900, 850, 836, 805, 780, 745, 714, 642. $^1$H NMR (300 MHz, CDCl$_3$): δ (ppm)=1.43 (s, 9H, CH$_3$), 2.62-2.72 (m, 1H, CH$_2$), 2.78-2.88 (m, 1H, CH$_2$), 4.30-4.32 (m, 0.2H, CHN cis), 4.48-4.52 (m, 0.8H, CHN trans), 5.21 (d, J=8.1 Hz, 0.8H, NH trans), 5.73-5.86 (m, 0.2H, Hb'), 6.24-6.34 (m, 0.8H, Hb), 6.50 (d, J=15.6 Hz, 0.8H, Ha), 6.59 (d, J=11.4 Hz, 0.2H, Ha'), 6.72 (d, J=6.3 Hz, 0.2H, NH cis), 7.17-7.20 (m, 2H, Ph), 7.24-7.27 (m, 2H, Ph). $^{13}$C NMR (75 MHz, CDCl$_3$): δ (ppm)=27.2 (CH$_3$), 29.0 (CH$_2$ cis or trans), 35.0 (CH$_2$ cis or trans), 51.9 (CHN cis or trans), 53.1 (CHN cis or trans), 79.6 (C(CH$_3$)$_3$ cis or trans), 81.0 (C(CH$_3$)$_3$ cis), 109.6 (Carom cis), 109.7 (Carom trans), 117.8 (CN cis ou trans), 117.9 (CN cis or trans), 125.8 (C arom), 126.5 (CH=cis or trans), 127.1 (CH=cis or trans), 127.8 (Carom), 128.3 (Carom), 128.5 (Carom), 130.1 (Carom), 131.1 (Carom), 131.4 (Carom), 131.5 (CH=cis or trans), 132.3 (CH=cis or trans), 140.2 (Carom), 155.4 (COO), 174.9 (COO). Mass exact calculated for C$_{17}$H$_{20}$N$_2$NaO$_4$[M+Na]$^+$: 339.1315. found 339.1299.

The enantiomeric purity was determined by HPLC after esterification with TMSCHN$_2$ (Lux 5 µm cellulose-2, hexane:iPrOH 85:15, 1 mL min$^{-1}$, λ=210 nm, 20° C., $t_R$ (cis (S))=16.3 min, $t_R$ (trans (S))=19.2 min, $t_R$ (cis (R))=23.8 min, $t_R$ (trans (R))=32.1 min).

F2.5. (S)-2-(t-butyloxycarbonylamino)-5-(4-methoxyphenyl)pent-4-enoïc acid (I″e)

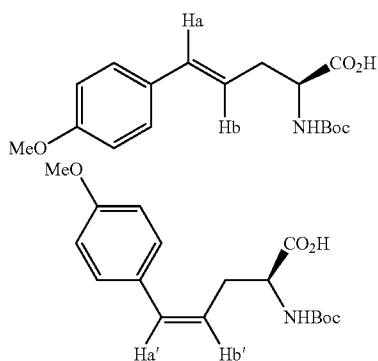

120 mg of phosphonium salt (Ira) and 136 mg (1 mmol, 5 eq) of 4-methoxybenzaldehyde were used to afford the amino acid (re) in 67% yield in a ratio cis/trans=24:76. Pale yellow oil —$R_f$: 0.42 (Ethyl acetate/petroleum ether 3:7+1% acetic acid). Enantiomeric excess >98%*-$[\alpha]_D$=+12.3 (c=0.5; CHCl$_3$). IR (cm$^{-1}$): 3288 (N—H), 2978-2838 (C—H), 1713 (C=O), 1578 (C=O), 1512, 1456, 1441, 1394, 1368, 1289, 1248, 1174 (O—CH$_3$), 1111, 1043, 968, 911, 839, 734, 633. $^1$H NMR (300 MHz, CDCl$_3$): δ (ppm)=1.44 (s, 9H, CH$_3$), 2.56-2.79 (m, 1.5H, CH$_2$ trans), 2.94-2.99 (m, 0.5H, CH$_2$ cis), 3.81 (s, 3H, OCH$_3$), 4.33-4.43 (m, 1H, CHN cis+trans), 5.03-5.13 (m, 1H, NH cis+trans), 5.52-5.58 (m, 0.24H, Hb'), 5.93-6.02 (m, 0.76H, Hb), 6.43 (d, J=15.6 Hz, 0.76H, Ha), 6.54 (d, J=11.4 Hz, 0.24H, Ha'), 6.83-6.89 (m, 2H, Harom), 7.17-7.22 (m, 1H, Harom), 7.29-7.32 (m, 1H, Harom). $^{13}$C NMR (75 MHz, CDCl$_3$): δ (ppm)=28.3 (CH$_3$), 31.1 (CH$_2$ cis), 35.7 (CH$_2$ trans), 53.1 (CHN), 55.3 (OCH$_3$), 80.5 (C(CH$_3$)$_3$ trans), 80.6 (C(CH$_3$)$_3$ cis), 113.8 (Carom), 114.0 (Carom), 121.1 (CH=), 123.9 (CH=), 125.3 (Carom), 127.5 (Carom), 128.3 (Carom), 129.0 (Carom), 129.7 (Carom), 130.0 (Carom), 132.2 (CH=), 133.7 (CH=), 137.9 (Carom), 155.8 (COO), 158.6 (Carom-OCH$_3$ cis), 159.2 (Carom-OCH$_3$ trans), 176.8 (COO). Mass exact calculated for C$_{17}$H$_{23}$N$_1$Na$_1$O$_5$ [M+Na]$^+$: 344.1468. found 344.1448.*The enantiomeric purity was determined by HPLC on chiral column after esterification with TMSCHN$_2$ (Lux 5 µm cellulose-2, hexane:iPrOH 95:5, 1.5 mL·min$^{-1}$, λ=254 nm, 20° C., $t_R$ (cis (R))=8.3 min, $t_R$ (trans (R))=10.4 min, $t_R$ (cis (S))=13.1 min, $t_R$ (trans (S))=16.7 min)

F2.6. (S)-2-(t-butyloxycarbonylamino)-5-(3,4-dimethoxyphenyl)pent-4-enoïc acid (I'f)

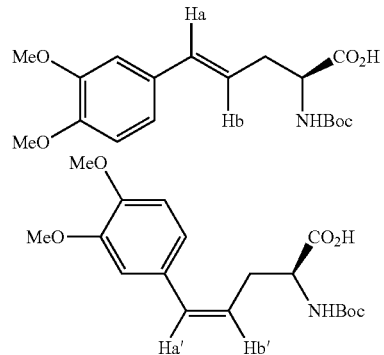

120 mg of phosphonium salt (II″a) and 200 mg (1.2 mmol, 6 eq) of 3,4-dimethoxybenzaldehyde were used to prepare the unsaturated amino acid (I″f) in 76% yield in a ratio cis/trans=20:80. Pale yellow oil —$R_f$: 0.44 (Ethyl acetate/petroleum ether 1:1+1% acetic acid). Enantiomeric excess >98%*-$[\alpha]_D$=+52.6 (c=0.5; CHCl$_3$). IR (cm$^-$): 3293 (N—H), 2975-2824 (C—H), 1743 (C=O), 1704 (C=O), 1604, 1515, 1463, 1393, 1265 (OCH$_3$), 1088, 1024, 964, 855, 783, 738, 656. $^1$H NMR (300 MHz, CDCl$_3$): δ (ppm)=1.43 (s, 9H, CH$_3$), 2.59-2.81 (m, 1.6H, CH$_2$ trans), 2.85-2.99 (m, 0.4H, CH$_2$ cis), 3.88 (s, 3H, OCH$_3$), 3.90 (s, 3H, OCH$_3$), 4.24-4.27 (m, 0.24H, CHN cis), 4.47 (m, 0.74H, CHN trans), 5.07 (d, J=7.8 Hz, 0.7H, NH trans), 5.52-5.60 (m, 0.2H, Hb'), 5.94-6.04 (m, 0.8H, Hb), 6.2 (sl, 0.2H, NH cis), 6.44 (d, J=15.6 Hz, 0.8H, Ha), 6.55 (d, J=11.4 Hz, 0.2H, Ha'), 6.79-6.92 (m, 3H, Harom). $^{13}$C NMR (75 MHz, CDCl$_3$): δ (ppm)=28.3 (CH$_3$)$_3$, 31.1 (CH$_2$ cis), 35.7 (CH$_2$ trans), 53.1 (CHN), 55.8 (OCH$_3$), 55.9 (OCH$_3$), 80.4 (C(CH$_3$)$_3$ trans), 81.7 (C(CH$_3$)$_3$ cis), 108.8 (Carom), 111.1 (Carom), 121.3 (CH=cis), 121.4 (CH=trans), 125.3 (Carom), 128.2 (Carom), 129 (Carom), 129.6 (Carom), 129.9 (Carom), 132.5

(CH=cis), 133.9 (CH=trans), 148.1 (Carom-OCH$_3$ cis), 148.6 (Carom-OCH$_3$ trans),148.8 (Carom-OCH$_3$ cis), 149.0 (Carom-OCH$_3$ trans), 155.6 (COO), 176.7 (COO). Mass exact calculated for C$_{18}$H$_{24}$NNa$_2$O$_6$ [M+2Na]$^+$: 396.1393. found 396.1403.*The enantiomeric purity was determined by HPLC after esterification with TMSCHN$_2$ (Lux 5 μm cellulose-2, hexane:iPrOH 95:5. 1.5 mL·min$^{-1}$, λ=254 nm, 20° C., t$_R$ (cis (R))=8.3 min, t$_R$ (trans (R))=10.4 min, t$_R$ (cis (S))=13.1 min, t$_R$ (trans (S))=16.7 min)

F2.7. (S)-2-(t-butyloxycarbonylamino)-5-furylpent-4-enoïc acid (I"g)

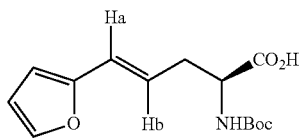

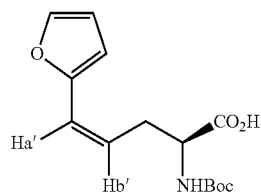

120 mg of phosphonium salt (II"a) and 38.4 mg of 2-furaldehyde were used to synthesize the unsaturated amino acid (I"g) in 80% yield. Pale yellow oil —R$_f$: 0.40 (Ethyl acetate/petroleum ether 3:7+1% acetic acid). Enantiomeric excess >98%*-Mu=+43.3 (c=0.4; CHCl$_3$). IR (cm$^-$): 3338 (N—H), 2978-2931 (C—H), 1780, 1694 (C=O), 1511, 1455, 1393, 1367, 1254, 1157 (C—O), 1349, 1017, 925, 863, 811, 735, 702, 653. $^1$H NMR (300 MHz, CDCl$_3$): δ (ppm)=1.45 (s, 9H, CH$_3$), 2.58-2.78 (m, 1H, CH$_2$), 2.90-3.16 (m, 1H, CH$_2$), 4.20-4.27 (m, 0.4H, CHN cis or trans), 4.34-4.48 (m, 0.6H, CHN cis or trans), 5.12-5.14 (m, 0.6H, NH cis or trans), 5.45-5.54 (m, 0.4H, Hb or Hb'), 6.00-6.10 (m, 0.6H, Hb or Hb'), 6.21 (d, J=3.3 Hz, 1H, Hfuryl), 6.35-6.41 (m, 3H, Ha, Ha', Hfuryl), 7.17-7.20 (m, 0.4H, NH cis or trans) 7.36 (dd, J=21.9, 1.2 Hz, 1H, Hfuryl). $^{13}$C NMR (75 MHz, CDCl$_3$): δ (ppm)=28.3 (CH$_3$)$_3$, 31.8 (CH$_2$ cis or trans), 35.5 (CH$_2$ cis or trans), 53.1 (CHN cis or trans), 54.5 (CHN cis or trans), 80.4 (C(CH$_3$)$_3$ cis or trans), 81.7 (C(CH$_3$)$_3$ cis or tans), 107.5 (Cfuryl cis or trans), 110.2 (Cfuryl cis or trans), 111.1 (Cfuryl cis or trans), 111.2 (Cfuryl cis or trans), 120.5 (CH=cis or trans), 122.2 (CH=cis or trans), 122.6 (CH=cis or trans), 123.1 (CH=cis or trans), 141.8 (Cfuryl cis or trans), 142.0 (Cfuryl cis or trans), 152.3 (Cfuryl cis or trans), 152.6 (Cfuryl cis or trans), 155.5 (COO), 155.7 (COO), 176.3 (COO), 176.8 (COO). Mass exact calculated for C$_{14}$H$_{18}$N$_1$O$_5$ [M+H]$^+$: 280.1190. found 280.1188.*The enantiomeric purity was determined by HPLC after esterification with TMSCHN$_2$ (Lux 5 μm cellulose-2, hexane:iPrOH 95:5.1 mL min$^{-1}$, λ=254 nm, 20° C., t$_R$ (cis+trans (S))=10.2 min, t$_R$ (cis or trans (R))=14.5 min, t$_R$ (cis or trans (R))=16 min)

F2.8. (S)-2-(t-butyloxycarbonylamino)-7-phenyl-hept-4-enoïc acid (I"h)

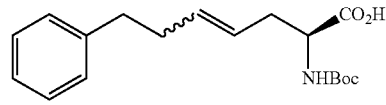 [SMILES: CC(C)(C)OC(=O)N[C@@H](CC=CCCc1ccccc1)C(=O)O]

120 mg phosphonium salt (II"a) and 120 mg (0.88 mmol, 4.4 eq) of 3-phenylpropanal were used to afford the unsaturated amino acid (I"h) in 57% yield. Orange solid —R$_f$: 0.48 (Ethyl acetate/petroleum ether 3:7+1% acetic acid). Enantiomeric excess >98%*-[α]$_D$=+54.0 (c=0.2; CHCl$_3$). IR (cm$^{-1}$): 3235 (N—H), 3077-2808 (C—H), 2326, 1652 (C=O), 1497, 1454, 1394, 1368, 1055, 983, 817, 736, 698, 649. $^1$H NMR (300 MHz, CDCl$_3$): δ (ppm)=1.46 (s, 9H, CH$_3$), 2.34-2.49 (m, 3H, CH$_2$), 2.57-2.72 (m, 3H, CH$_2$), 4.35-4.38 (m, 1H, CHN), 4.95 (d, J=7.2 Hz, 1H, NH), 5.32-5.40 (m, 1H, CH=), 5.62-5.68 (m, 1H, CH=), 7.11-7.23 (m, 3H, Harom), 7.27-7.34 (m, 2H, Harom). $^{13}$C NMR (75 MHz, CDCl$_3$): δ (ppm)=28.3 (CH$_3$), 29.2 (CH$_2$ cis or trans), 29.7 (CH$_2$ cis or trans), 30.9 (CH$_2$ cis or trans), 32.0 (CH$_2$ cis or trans), 34.3 (CH$_2$ cis or trans), 35.7 (CH$_2$ cis or trans), 53.0 (CHN), 79.2 (C(CH$_3$)$_3$), 123.3 (CH=cis or trans), 125.9 (CH=cis or trans), 128.3 (Carom), 128.5 (Carom), 128.7 (Carom), 133.4 (CH=cis or trans),134.8 (CH=cis or trans), 141.6 (Carom), 155.8 (COO), 176.9 (COO). Mass exact calculated for C$_{18}$H$_{25}$NNaO$_4$ [M+Na]$^+$: 342.1676. found 342.1647.*The enantiomeric purity was determined by HPLC after esterification with TMSCHN$_2$ (Lux 5 μm cellulose-2, hexane:iPrOH 95:5, 1 mL min$^{-1}$, λ=254 nm, 20° C., t$_R$ (cis or trans (S))=6.9 min, t$_R$ (cis or trans (S))=7.8 min, t$_R$ (cis or trans (R))=10.2 min, t$_R$ (cis or trans (R))=12.7 min).

F2.9. (S)-2-(t-butyloxycarbonylamino)-4-pentenoic acid (I"i)

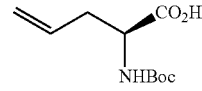

120 mg of phosphonium salt (II"a) and 12 mg of paraformaldehyde were used to afford the allylglycine (I"i) in 55% yield. Colorless oil —R$_f$: 0.39 (Ethyl acetate/petroleum ether 3:7+1% acetic acid). Enantiomeric excess >98%*-[α]$_D$=+13.5 (c=0.2; CHCl$_3$). IR (cm$^{-1}$): 3313 (N—H), 3082-2932 (C—H), 1703 (C=O), 1662 (C=O), 1509, 1439, 1394, 1368, 1250, 1157, 1050, 1024, 993, 920, 855, 778, 754, 739, 655. $^1$H NMR (300 MHz, CDCl$_3$): δ (ppm)=1.46 (s, 9H, CH$_3$), 2.57-2.67 (m, 2H, CH$_2$), 4.10-4.42 (m, 1H, CHN), 5.04 (d, J=7.5 Hz, 0.7H, NH), 5.16-5.36 (m, 2H, CH$_2$=), 5.69-5.87 (m, 1H, CH=), 6.12 (d, J=7.5 Hz, 0.3H, NH). $^{13}$C NMR (75 MHz, CDCl$_3$): δ (ppm)=27.4 (CH$_3$), 35.3 (CH$_2$), 51.8 (CHN), 79.3 (C(CH$_3$)$_3$), 118.4 (CH$_2$=), 131.1 (CH=), 155.5 (COO), 175.7 (COO). Mass exact calculated for C$_{10}$H$_{17}$NNaO$_4$ [M+Na]$^+$: 238.1050. found 238.1039.*The enantiomeric purity was determined by HPLC after esterification with TMSCHN$_2$ (Lux 5 μm cellulose-2, hexane:iPrOH 98:2, 1 mL min$^{-1}$, λ=210 nm, 20° C., t$_R$ (S)=12.2 min, t$_R$ (R)=20.2 min).

F2.10. (S)-2-(t-butyloxycarbonylamino)-6-phenyl-hex-4-enoïc acid (I"j)

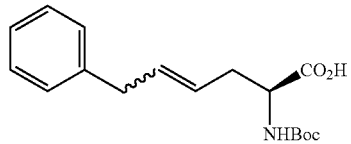 [SMILES: CC(C)(C)OC(=O)N[C@@H](CC=CCc1ccccc1)C(=O)O]

120 mg of phosphonium salt (II"a) and 48 mg of phenylacetaldehyde were used to afford the unsaturated amino acid (I"j) in 10% yield. Colorless oil. Enantiomeric excess >98%*-[α]$_D$=+49 (c=0.2; CHCl$_3$). IR (cm$^{-1}$): 3446, 3054, 2824, 1714, 1496, 1395, 1368, 1163, 1053, 741, 698, 602. Mass exact calculated for C$_{17}$H$_{23}$NNaO$_4$ [M+Na]$^+$: 328.1519. found 328.1502.*The enantiomeric purity was determined by HPLC after esterification with TMSCHN$_2$ (Lux 5 μm cellulose-2, hexane:iPrOH 97:3, 1 mL min$^{-1}$, λ=210 nm, 20° C., t$_R$ (cis or trans (S))=12.1 min, t$_R$ (cis or trans (S))=14.7 min, t$_R$ (cis or trans (R))=21.5 min, t$_R$ (cis or trans (R))=28.1 min)

F2.11. (S)-2-(t-butyloxycarbonylamino)-5-[4-(4,4,5,5-tetramethyl-[1,3,2]dioxaborolan-2-yl)]-pent-4-enoïc acid (I"k)

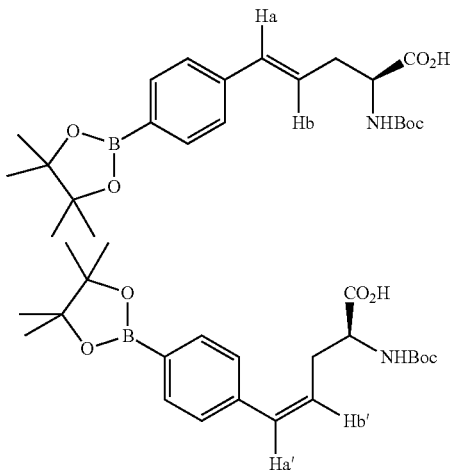

120 mg of phosphonium salt (II"a) and 93 mg of 4-(4,4,5,5-Tetramethyl-1,3,2-dioxaborolan-2-yl)benzaldehyde prepared by reaction of pinacol with 4-formylbenzeneboronic acid, were used to prepare the unsaturated amino acid (I"k) in 57% yield in a ratio cis/trans=25:75. Colorless oil —R$_f$: 0.40 (Ethyl acetate/petroleum ether 3:7+1% acetic acid). Enantiomeric excess >98%*-[α]$_D$=+12.8 (c=0.6; CHCl$_3$). IR (cm$^{-1}$): 3346 (N—H), 2979-2931 (C—H), 1714 (C=O), 1608, 1515, 1496, 1455, 1397, 1358, 1321, 1270, 1214, 1143 (C—O), 1089, 1052, 1019, 963, 859, 787, 696, 656, 607, 546, 540, 535, 524, 517. $^1$H NMR (300 MHz, CDCl$_3$): δ (ppm)=1.36 (s, 12H, (CH$_3$)$_2$), 1.44 (s, 9H, CH$_3$), 2.67-2.80 (m, 2H, CH$_2$), 4.48-5.13 (m, 1H, CHN), 5.16-6.18 (m, 1H, NH), 5.61-5.73 (m, 0.25H, Hb'), 6.10-6.25 (m, 0.75H, Hb), 6.51 (d, J=15.6 Hz, 0.75H, Ha), 6.63 (d, J=12.3 Hz, 0.25H, Ha'), 7.15-7.41 (m, 4H, Harom). $^{13}$C NMR (75 MHz, CDCl$_3$): δ (ppm)=24.8 ((CH$_3$)$_2$), 28.3 (CH$_3$), 31.2 (CH$_2$ cis), 35.9 (CH$_2$ trans), 53.1 (CHN trans), 54.4 (CHN cis), 80.4 (C(CH$_3$)$_3$ trans), 81.7 (C(CH$_3$)$_3$ cis), 83.8 (C(CH$_3$)$_2$), 116.0 (Carom), 124.8 (Carom), 125.3 (CH=cis), 125.6 (CH=trans), 126.4 (Carom), 128.0 (Carom), 128.2 (Carom), 129.0 (Carom), 129.4 (Carom), 131.6 (Carom), 132.5 (Carom), 134.2 (Carom), 134.8 (CH=cis or trans), 135.1 (CH=cis or trans), 137.9 (Carom), 139.5 (Carom), 155.6 (COO), 176.1 (COO). Mass exact calculated for C$_{22}$H$_{32}$BNNaO$_6$ [M+Na]$^+$: 440.2219. found 440.2215.*The enantiomeric purity was determined by HPLC after esterification with TMSCHN$_2$, (Lux 5 μm cellulose-2, hexane:iPrOH 90:10, 1 mL·min$^{-1}$, λ=210 nm, 20° C., t$_R$ (trans (S))=6.9 min, t$_R$ (cis (S))=7.8 min, t$_R$ (trans (R))=10.2 min, t$_R$ (cis (R))=12.7 min)

F2.12. (S)-2-(t-butyloxycarbonylamino)-5-(25,26,27,28-tetrapropoxycalix-4-arenyl)-4-enoïc acid (I"l)

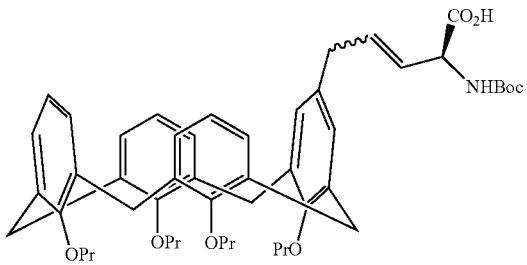

120 mg of phosphonium salt (II"a) and 248 mg aldehyde derived from calix-Plarene were used to prepare the unsaturated amino acid (I"l) in 25% yield. Colorless oil —R$_f$: 0.47 (Ethyl acetate/petroleum ether 3:7+1% acetic acid). Enantiomeric excess >98%*-[α]$_D$=+7.5 (c=0.4; CHCl$_3$). IR (cm$^-$): 3066 (N—H), 2957-2875 (C—H), 1716 (C=O), 1625, 1499, 1465, 1396, 1393, 1367, 1303, 1275, 1242, 1217, 1167, 1127 (OPr), 1086, 1039, 1005, 966, 917, 891, 831, 760, 726, 691, 665. $^1$H NMR (300 MHz, CDCl$_3$): δ (ppm)=0.98-1.03 (m, 12H, CH$_3$, OPr), 1.47 (s, 9H, CH$_3$), 1.94 (m, 8H, CH$_2$, OPr), 2.57-2.72 (m, 2H, CH$_2$), 3.16 (m, 4H, Ar—CH$_2$—Ar), 3.80 (m, 4H, CH$_2$O, OPr), 3.90 (m, 4H, CH$_2$O, OPr), 4.35 (d, J=3.3 Hz, 1H, CHN cis or trans), 4.45 (m, 4H, Ar—CH$_2$—Ar), 4.90 (d, J=7.8 Hz, 1H, NH), 5.03 (d, J=7.2 Hz, 1H, CHN cis or trans), 5.34 (m, 1H, CH=), 5.80 (m, 1H, CH=), 6.20-6.90 (m, 11H, Harom). $^{13}$C NMR (75 MHz, CDCl$_3$): δ (ppm)=10.1 (CH$_3$, OPr cis or trans), 10.2 (CH$_3$, OPr cis or trans), 10.4 (CH$_3$, OPr cis or trans), 10.5 (CH$_3$, OPr cis or trans), 23.1 (CH$_2$, OPr cis or trans), 23.2 (CH$_2$, OPr cis or trans), 23.3 (CH$_2$, OPr cis or trans), 23.4 (CH$_2$, OPr cis or trans), 28.3 (CH$_3$), 29.6 (CH$_2$ cis or trans), 29.7 (CH$_2$ cis or trans), 31.0 (Ar—CH$_2$—Ar), 53.1 (CHN cis or trans), 53.1 (CHN cis or trans), 76.7 (OCH$_2$, OPr), 76.8 (OCH$_2$, OPr), 80.4 (C(CH$_3$)$_3$), 115.3 (Carom cis or trans), 121.8 (Carom cis or trans), 121.9 (Carom cis or trans), 126.3 (Carom cis or trans), 126.5 (Carom cis or trans), 127.8-128.7 (m, Carom), 129.6 (Carom cis or trans), 130.1 (Carom cis or trans), 130.4 (Carom cis or trans), 132.8 (Carom cis or trans), 134.4 (Carom cis or trans), 134.5 (Carom cis or trans), 134.7 (Carom cis or trans), 135.5 (Carom cis or trans), 135.7 (Carom cis or trans), 156.3 (COO), 176.7 (COO). Mass exact calculated for C$_{10}$H$_N$N$_1$Na$_1$O$_4$ [M+Na]$^+$: 828.4446. found 828.4420.*The enantiomeric purity was determined by HPLC after esterification with TMSCHN$_2$ (Lux 5 μm cellulose-2, hexane:iPrOH 98:2, 0.8 mL·min$^{-1}$, λ=254 nm, 20° C., t$_R$ (cis or trans (S))=14.6 min, t$_R$ (cis or trans (S))=21.4 min, t$_R$ (cis or trans (R))=30.8 min, t$_R$ (cis or trans (R))=39.2 min)

F2.13. (S)-methyl-2-(t-butyloxycarbonylamino)-5-ferrocenylpent-4-enoate (I"m)

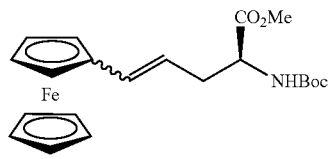

120 mg of phosphonium salt (II"a) and 214 mg (1 mmol, 5 eq.) of ferrocene-carboxaldehyde were stirred at 90° C. with 254 mg (1.2 mmol, 6 eq) of $K_3PO_4$ during 16 hours. The reaction mixture was hydrolyzed by distilled water (5 mL) and extracted with diethyl ether (3×5 mL). The aqueous layer was acidified with $KHSO_4$ (1M) until pH=3, and extracted with ethyl acetate (3×5 mL). The combined organic layers were dried over magnesium sulfate and the solvent was evaporated. The crude product was dissolved in 2 mL of a mixture toluene/methanol (3:2), and 0.13 mL (0.25 mmol) $TMSCHN_2$ were added. The reaction mixture was stirred 30 minutes at room temperature, and the solvent evaporated. The residue was purified by chromatography with ethyl acetate/petroleum ether (3:7) as eluent. Ferrocenyl amino ester (I"m) was obtained in 51% yield with a ratio cis/trans=50:50. Orange oil —$R_f$: 0.42 (Ethyl acetate/petroleum ether 1:4). $[\alpha]_D$=+133 (c=0.1; $CHCl_3$). IR ($cm^{-1}$): 3390 (N—H), 2927-2854 (C—H), 1779 (C=O), 1695 (C=O), 1509, 1455, 1392, 1366, 1251, 1158, 1106, 1048, 1023, 1001, 821, 734, 662. $^1H$ NMR (300 MHz, $CDCl_3$): δ (ppm)=1.46-1.47 (2s, 9H, $CH_3$ cis and trans), 2.47-2.87 (2m, 2H, $CH_2$), 3.76-3.79 (2s, 3H, $OCH_3$ cis and trans), 4.12-4.14 (2s, 5H, Fc, cis and trans), 4.20-4.24 (2m, 2H, Fc, cis and trans), 4.30-4.35 (2m, 2H, Fc, cis and trans), 4.38-4.47 (m, 1H, CHN), 5.06-5.12 (m, 1H, NH), 5.33-5.39 (m, 1H, CH=), 5.58-5.68 (m, 1H, CH=), 6.22 (d, J=15.6 Hz, 0.52H, CH=trans), 6.26 (d, J=11.8 Hz, CH=, cis). $^{13}C$ NMR (75 MHz, $CDCl_3$): δ (ppm)=28.3 ($CH_3$), 31.7 ($CH_2$), 35.8 ($CH_2$ cis or trans), 52.3 ($OCH_3$ cis or trans), 52.4 ($OCH_3$ cis or trans), 53.0 (CHN, cis or trans), 53.1 (CHN, cis or trans), 66.6 (CH, Fc, cis or trans), 66.7 (CH, Fc, cis or trans), 68.6 (CH, Fc cis or trans), 68.7 (CH, Fc, cis or trans), 68.8 (CH, Fc cis or trans), 68.9 (CH, Fc cis or trans), 69.0 (CH, Fc cis or trans), 69.3 (CH, Fc cis or trans), 81.0 ($C(CH_3)_3$), 82.7 ($C(CH_3)_3$), 120.4 (CH=cis or trans), 121.7 (CH=cis or trans), 130.1 (CH=cis or trans), 131.8 (CH=cis or trans), 155.2 (COO, cis or trans), 155.3 (COO, cis or trans), 172.6 (COO, cis or trans), 173 (COO, cis or trans). Mass exact calculated for $C_{21}H_{27}FeNNaO_4$ [M+Na]$^+$: 436.1182. found 436.1193.*The enantiomeric purity was determined by HPLC (Lux 5 μm cellulose-2, hexane:iPrOH 97:3, 0.8 mL $min^{-1}$, λ=254 nm, 20° C., $t_R$ (cis (S))=27.4 min, $t_R$ (trans (S))=30.7 min, $t_R$ (cis+trans (R))=43.1 min)

F2.14. bis-[(S)-2-(t-Butyloxycarbonylamino)pent-4-en-5-yl-oïc acid]-1,3-benzene (I"n)

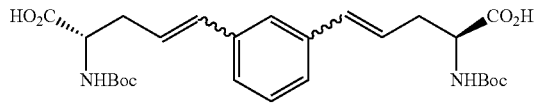 [SMILES: CC(C)(C)OC(=O)N[C@@H](CC=Cc1cccc(C=CC[C@H](NC(=O)OC(C)(C)C)C(=O)O)c1)C(=O)O]

120 mg phosphonium salt (II"a) and 13.4 mg (0.1 mmol, 0.5 eq.) of m-phthaldialdehyde were used to prepare the unsaturated amino acid (I"n) in 85% yield. White solid —$R_f$: 0.23 (Ethyl acetate/petroleum ether 3:7+1% acetic acid). Enantiomeric excess >98%*-$[\alpha]_D$=+82.6 (c=0.5; $CHCl_3$). IR ($cm^{-1}$): 3555 (N—H), 3407 (N—H), 3056-3407 (C—H), 2326, 2244, 2030, 1949, 1583 (C=O), 1573 (C=01493, 1471, 1462, 1431, 1296, 1273, 1241, 1180, 1129, 1108, 1070, 1022, 909, 851, 824, 795, 731, 698. $^1H$ NMR (300 MHz, $CDCl_3$): δ (ppm)=1.44 (s, 18H, $CH_3$), 2.59-2.89 (m, 4H, $CH_2$), 4.14-4.70 (m, 2H, CHN cis+trans), 5.26-5.32 (m, 1H, NH), 5.63-5.71 (m, 1H, CH=), 6.01-6.06 (m, 1H, CH=), 6.35-6.54 (m, 2H, CH=), 7.01-7.07 (m, 1H, NH), 7.08-7.11 (m, 2H, Harom), 7.14-7.18 (m, 2H, Harom). $^{13}C$ NMR (75 MHz, $CDCl_3$): δ (ppm)=28.3 ($CH_3$), 31.3 ($CH_2$), 35.7 ($CH_2$), 53.1 (CHN cis or trans), 54.5 (CHN cis or trans), 80.4 ($C(CH_3)_3$), 125.3 (Carom), 126.0 (CH=cis or trans), 126.1 (CH=cis or trans), 127.5 (CH=cis or trans), 127.9 (Carom), 128.3 (CH=cis or trans), 128.5 (CH=cis or trans), 129.0 (Carom), 132.4 (CH=cis or trans), 134.1 (CH=cis or trans), 137.0 (Carom), 137.1 (Carom), 137.9 (Carom), 155.6 (COO), 156.8 (COO), 175.9 (COO). Mass exact calculated for $C_{26}H_{36}N_2NaO_8$ [M+Na]$^+$: 527.2364; found 527.2372.* The enantiomeric purity was determined by HPLC after esterification with $TMSCHN_2$ and hydrogenation (Lux 5 μm cellulose-2, hexane: iPrOH 90:10, 1 mL.$min^{-1}$, λ=210 nm, 20° C., $t_R$ (SS)=14.3 min, $t_R$ (RS+SR)=21.7 min, $t_R$ (RR)=32.2 min).

F2.15. (S)-2-(t-butyloxycarbonylamino)-7-phenyl-hept-4,6-dienoïc acid (I"o)

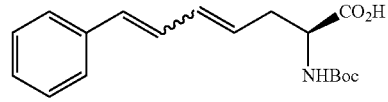 [SMILES: CC(C)(C)OC(=O)N[C@@H](CC=CC=Cc1ccccc1)C(=O)O]

120 mg of phosphonium salt (II"a) and 53 mg of trans-cinnamaldehyde were used to synthesize the unsaturated amino acid (I"o) in 77% yield. White solid -$R_f$: 0.53 (Ethyl acetate/petroleum ether 3:7+1% acetic acid). Enantiomeric excess >98%*-$[\alpha]_D$=+33.6 (c=0.8; $CHCl_3$). IR ($cm^{-1}$): 3319 (N—H), 3083-3853 (C—H), 1710 (C=O), 1496, 1450, 1393, 1368, 1251, 1159, 1056, 1027, 989, 948, 920, 857, 807, 778, 752, 731, 694. $^1H$ NMR (300 MHz, $CDCl_3$): δ (ppm)=1.44-1.47 (2s, 9H, $CH_3$ cis or trans), 2.47-2.94 (m, 1H, $CH_2$), 4.14-4.33 (m, 0.3H, CHN cis or trans), 4.45-4.53 (m, 0.7H, CHN cis or trans), 5.04-5.20 (m, 1H, CH=cis or trans or NH), 6.27-6.38 (m, 0.7H, CH=cis or trans or NH), 6.49-6.62 (m, 1H, CH cis or trans or NH), 6.76 (dd, J=10.2, 15.6 Hz, 0.7H, CH=cis or trans), 7.03 (dd, J=11.4, 15.6 Hz, 0.3H, CH=cis or trans), 7.18-7.36 (m, 5H, Harom). $^{13}C$ NMR (75 MHz, $CDCl_3$): δ (ppm)=27.3 ($CH_3$), 31.9 ($CH_2$ cis or trans), 35.6 ($CH_2$ cis or trans), 53.1 (CHN cis or trans), 54.6 (CHN cis or trans), 79.4 ($C(CH_3)_3$ cis or trans), 80.8 ($C(CH_3)_3$ ci or trans), 122.5 (Carom), 123.8 (CH=cis or trans), 124.0 (CH=cis or trans), 124.3 (Carom), 125.3 (Carom), 125.5 (Carom), 126.5 (Carom), 126.7 (Carom), 127.2 (Carom), 127.4 (Carom), 127.6 (Carom), 128 (Carom), 130.9 (CH=cis or trans), 131.4 (CH=cis or trans), 131.9 (CH=cis or trans), 133 (CH=cis or trans), 133.5 (CH=cis or trans), 133.6 (CH=cis or trans), 136.1 (Carom), 136.8 (Carom), 154.6 (COO), 155.7 (COO cis or trans), 175.2 (COO cis or trans), 175.5 (COO cis or trans). Mass exact calculated for $C_{17}H_{19}F_3N_2NaO_4$ [M−H]$^-$: 316.1554. found 316.1560.*The enantiomeric purity was determined by HPLC after esterification with TMSCHN$_2$ (Lux 5 μm cellulose-2, hexane:iPrOH 95:5, 1 mL min−1, λ=210 nm, 20° C., t$_R$ (cis or trans (S))=20.1 min, t$_R$ (cis or trans (S))=29 min, t$_R$ (cis or trans (R))=32.2 min, t$_R$ (cis or trans (R))=61.2 min).

F2.16. (S)-2-(t-butyloxycarbonylamino)-7-(4-azidophenyl)hept-4,6-dienoïc (I"p)

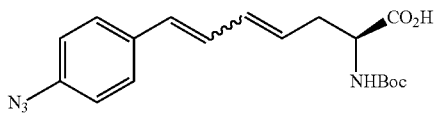 [SMILES: CC(C)(C)OC(=O)N[C@@H](CC=CC=Cc1ccc(N=[N+]=[N-])cc1)C(=O)O]

120 mg of phosphonium salt (II"a) and 69.2 mg of (E)-4-azidophenylprop-2-enal were used to afford the unsaturated amino acid (I"p) in 56% yield. Red solid —R$_f$: 0.43 (Ethyl acetate/petroleum ether 3:7+1% acetic acid). Enantiomeric excess >98%*–[α]$_D$=+81.6 (c=0.4; CHCl$_3$). IR (cm$^{-1}$): 3346 (N—H), 2925-2854 (C—H), 2114 (N$_3$), 1706 (C=O), 1598, 1504, 1454, 1393, 1367, 1284, 1259, 1157, 1127, 1053, 1025, 986, 948, 825, 789, 754, 699. $^1$H NMR (300 MHz, CDCl$_3$): δ (ppm)=1.43-1.46 (2s, 9H, CH$_3$ cis and trans), 2.62-2.90 (m, 2H, CH$_2$), 4.26-4.33 (m, 0.25H, CHN cis or trans), 4.44-4.46 (m, 0.75H, CHN cis or trans or NH), 5.42-5.50 (m, 0.55H, CH=cis or trans or NH), 5.67-5.77 (m, 0.5H, CH=cis or trans or NH), 6.24-6.38 (m, 1H, CH=cis or trans), 6.42-6.56 (m, 1H, CH=cis or trans), 6.65-6.70 (m, 0.53H, CH=cis or trans), 6.97 (dd, J=8.4, 3.0 Hz, 2H, Harom), 7.38 (dd, J=8.4, 13.2 Hz, 2H, Harom). $^{13}$C NMR (75 MHz, CDCl$_3$): δ (ppm)=27.3 (CH$_3$), 28.7 (CH$_2$ cis or trans), 29.5 (CH$_2$ cis or trans), 52.1 (CHN), 79.4 (C(CH$_3$)$_3$), 118.2 (Carom), 122.2 (Carom), 124.0 (CH=cis or trans), 124.3 (CH=cis or trans), 126.5 (Carom), 126.9 (Carom), 127.2 (CH=cis or trans),128.1 (CH=cis or trans), 130.0 (Carom), 131.6 (Carom), 131.7 (Carom), 132.3 (Carom), 133.1 (Carom), 133.5 (Carom), 137.9 (Carom), 138.1 (Carom), 154.5 (COO), 175.3 (COO). Mass exact calculated for C$_{18}$H$_{21}$N$_4$Na$_2$O$_4$ [M–H+2Na]$^+$=403.1358. found 403.1303.*The enantiomeric purity was determined by HPLC after esterification with TMSCHN$_2$ (Lux 5u cellulose-2, hexane:iPrOH 95:5, 1 mL min−1. λ=254 nm, 20° C., t$_R$ (cis or trans (S))=12.2 min, t$_R$ (cis or trans (S))+t$_R$ (cis or trans (R))=16.2 min, t$_R$ (cis or trans (R))=30.4 min)

F2.17. (S)-2-(t-butyloxycarbonylamino)-7-ethoxycarbonyl-4,6-dienoïc acid (I"q)

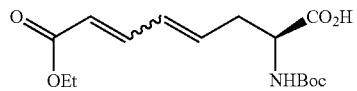 [SMILES: CCOC(=O)C=CC=CC[C@H](NC(=O)OC(C)(C)C)C(=O)O]

120 mg of phosphonium salt II"a and 26 mg of ethyl 4-oxo-2-butenoate were used to afford unsaturated aminoacid I"q in 58% yield as a pale yellow oil —Rf: 0.36 (Ethyl acetate/petroleum ether 3:7+1% acetic acid); $^1$H NMR (300 MHz, CDCl$_3$): δ (ppm)=1.22 (t, 3H, J=36.6 Hz, CH$_3$), 1.45 (s, 9H, (CH$_3$)$_3$), 2.40-2.79 (m, 2H, CH$_2$), 4.12 (q, J=7.54 Hz, CH$_2$), 4.32-4.39 (m, 1H, CHN), 4.93-4.99 (m, 1H, NH), 5.77 (d, 0.8H, J=13.9 Hz, CH=cis or trans), 5.87 (d, J=13.4 Hz, 0.2H, CH=cis or trans), 5.91-6.03 (m, 1H, CH=), 6.15-6.24 (m, 1H, CH=), 6.16-6.24 (m, 1H, CH=); $^{13}$C NMR (75 MHz, CDCl$_3$): δ (ppm)=14.2 (CH$_3$), 29.3 ((CH$_3$)$_3$), 39.9 (CH$_2$),52.8 (CHN), 60.5 (CH$_2$O), 80.5 (C(CH$_3$)$_3$), 121.1 (CH=cis or trans), 122.9 (CH=cis or trans), 128.8 (CH=cis or trans), 130.9 (CH=cis or trans), 132.1 (CH=cis or trans), 136.6 (CH=cis or trans), 138.5 (CH=cis or trans), 143.8 (CH=cis or trans), 155.5 (COO), 167.1 (COO).

F2.18. (S)-2-(t-butyloxycarbonylamino)-7-dimethylhept-4,6-dienoïc acid (I"r)

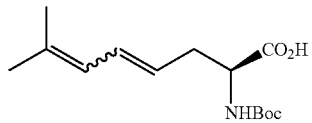 [SMILES: CC(C)=CC=CC[C@H](NC(=O)OC(C)(C)C)C(=O)O]

120 mg of phosphonium salt II"a and 84 mg of 3-methyl-2-butenal were used to afford the unsaturated amino acid I"r in 70% yield as a colorless oil —Rf: 0.51 (Ethyl acetate/petroleum ether 3:7+1% acetic acid)-[α]$_D$=+70.7 (c=0.75; CHCl$_3$); $^1$H NMR (300 MHz, CDCl$_3$): δ (ppm)=1.36 (s, 9H, (CH$_3$)$_3$), 1.68 (d, J=5.82 Hz, 6H, CH$_3$), 2.51-2.66 (m, 2H, CH$_2$), 4.19-4.33 (m, 2H, CHN,) 4.89-5.01 (m, 1H, NH), 5.31-5.49 (m, 1H, CH=), 5.72 (d, 0.8H, J=11.16 Hz, CH=cis or trans), 5.95 (d, J=12.1 Hz, CH=cis or trans), 6.21-6.32 (m, 1H, CH=); $^{13}$C NMR (75 MHz, CDCl$_3$): δ (ppm)=25.9 (CH$_3$), 26.3 (CH$_3$), 28.3 ((CH$_3$)$_3$), 29.7 (CH$_2$ cis or trans), 30.0 (CH$_2$ cis or trans), 53.7 (CHN), 80.1 (C(CH$_3$)$_3$), 119.8 (CH=cis or trans), 121.8 (CH=cis or trans), 124.4 (CH=cis or trans), 124.6 (CH=cis or trans), 128.0 (CH=cis or trans), 128.5 (CH=cis or trans), 130.8 (CH=cis or trans), 134.8 (C=cis or trans), 137.0 (C=cis or trans), 155.8 (COO), 176.7 (COO); Mass exact calculated for C$_{14}$H$_{22}$NO$_4$ [M–H]$^+$: 268.1543. found 268.1550.

F2.19. (S)-2-(t-butyloxycarbonylamino)-7-(4-nitrophenyl)hept-4,6-dienoïc acid (I"s)

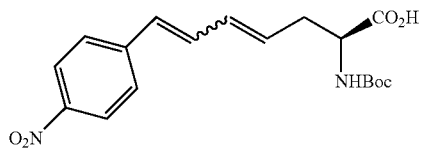 [SMILES: CC(C)(C)OC(=O)N[C@@H](CC=CC=Cc1ccc([N+](=O)[O-])cc1)C(=O)O]

120 mg of phosphonium salt II"a and 53 mg of 4-nitro-trans-cinnamaldehyde were used to synthesize the unsaturated amino acid I"s in 70% yield as a yellow solid —Rf: 0.46 (Ethyl acetate/petroleum ether 3:7+1% acetic acid)-Enantiomeric excess >98%*–[α]$_D$=+61.6 (c=0.25; CHCl$_3$); $^1$H NMR (300 MHz, CDCl$_3$): δ (ppm)=1.34-1.7 (2s, 9H, CH$_3$ cis or trans), 2.47-2.94 (m, 1H, CH$_2$), 4.25-4.39 (m, 1H, CHN), 4.99-4.01 (m, 1H, NH), 5.51-5.60 (m, 0.2 H, CH=), 5.75-5.85 (m, 0.8H, CH=cis or trans), 6.21-6.31 (m, 1H, CH=cis or trans), 6.45 (d, 0.8H, J=15.9 Hz, CH=cis or trans), 6.52 (d, 0.2 H, J=15.6 Hz, CH=cis or trans), 6.76-6.85 (m, 1H, CH=cis or trans), 7.41 (d, J=8.7 Hz, 1.6H, H$_{arom}$ cis or trans), 7.45 (d, J=8.74 Hz, 0.4H, H$_{arom}$), 8.08-8.10 (2d, 2H, J=8.7, 9.0 Hz, H$_{arom}$); $^{13}$C NMR (75 MHz, CDCl$_3$): δ (ppm)=28.3 (CH$_3$), 35.7 (CH$_2$), 53.0 (CHN), 80.6 (C(CH$_3$)$_3$, 123.6 (CH=cis or trans), 124.1 (CH=cis or trans), 125.3 (CH=cis or trans), 126.6 (CH=cis or trans), 126.9 (CH=cis or trans), 127.8 (CH=cis or trans), 128.2 (CH=cis or trans), 129.0 (CH=cis or trans), 129.6 (CH=cis or trans), 131.3 (CH=cis or trans), 131.5 (CH=cis or trans), 132.8 ($C_{arom}$), 133.9 (CH=cis or trans), 143.6 ($C_{arom}$), 143.7 ($C_{arom}$), 146.7 ($C_{arom}$), 146.8 ($C_{arom}$), 155.5 (COO), 176.1 (COO); Mass exact calculated for $C_{18}H_{21}N_2O_6$1M−HT:361.1391. found 361.1394.

The enantiomeric purity was determined by HPLC after esterification with TMSCHN$_2$ (Lux 5 μm cellulose-2, hexane:iPrOH 85:15, 0.8 mL min−1, λ=254 nm, 20° C., $t_R$ (cis or trans (S))=16.8 min, $t_R$ (cis or trans (S))=22.2 min, $t_R$ (cis or trans (R))=30.9 min, $t_R$ (cis or trans (R))=35.8 min)

F2.20. (S)-2-(t-butyloxycarbonylamino)-7-(2-thiophenyl)hept-4,6-dienoïc acid (I"t)

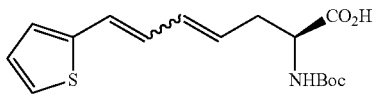 [SMILES: CC(C)(C)OC(=O)N[C@@H](CC=CC=Cc1cccs1)C(=O)O]

120 mg of phosphonium salt II"a and 55 mg of thiophene propenal were used to synthesize the unsaturated amino acid I"t in 80% yield as a pale yellow solid —Rf: 0.40 (Ethyl acetate/petroleum ether 3:7+1% acetic acid)-Enantiomeric excess >98%*−[α]$_D$=+61.6 (c=0.25; CHCl$_3$); $^1$H NMR (300 MHz, CDCl$_3$): δ (ppm)=1.37 (s, 9H, CH$_3$), 2.49-2.66 (m, 2H, CH$_2$), 4.34-4.36 (m, 1H, CHN), 4.98-5.01 (m, 1H, NH), 5.54-5.56 (m, 0.17 H, CH=), 5.62-5.65 (m, 0.83H, CH=cis or trans), 6.11-6.19 (m, 1H, CH=cis or trans), 6.42-6.52 (m, 1H, CH=cis or trans), 6.87-6.90 (m, 2H, CH=cis or trans), 7.06-7.08 (m, 1H, CH=cis or trans), 7.10-7.11 (m, 1H, CH=cis or trans); $^{13}$C NMR (75 MHz, CDCl$_3$): δ (ppm)=28.3 (CH$_3$), 29.7 (CH$_2$), 53.1 (CHN), 80.5 (C(CH$_3$)$_3$ 123.2 (CH=cis or trans), 124.3 (CH=cis or trans), 124.7 (CH=cis or trans), 124.9 (CH=cis or trans), 125.3 (CH=cis or trans), 125.8 (CH=cis or trans), 126.2 (CH=cis or trans), 126.9 (CH=cis or trans), 127.5 (CH=cis or trans), 128.1 (CH=cis or trans), 128.2 (CH=cis or trans), 128.9 (CH=cis or trans), 129 (CH=cis or trans), 132.1 (CH=cis or trans), 134.1 (CH=cis or trans), 134.2 (CH=cis or trans), 155.6 (COO), 176.5 (COO); Mass exact calculated for $C_{16}H_{20}NO_4S$ [M−H]$^-$: 322.1108. found 322.1111.

*The enantiomeric purity was determined by HPLC after esterification with TMSCHN$_2$ (Lux 5u cellulose-2, hexane: iPrOH 90:10, 0.8 mL min−1, λ=254 nm, 20° C., $t_R$ (cis or trans (S))=9.6 min, $t_R$ (cis or trans (S))=11.4 min, $t_R$ (cis or trans (R))=13.1 min, $t_R$ (cis or trans (R))=19.2 min).

F2.21 (S)-2-(t-butyloxycarbonylamino)-7-(2-furyl)hept-4,6-dienoïc acid (I"a)

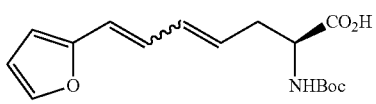 [SMILES: CC(C)(C)OC(=O)N[C@@H](CC=CC=Cc1ccco1)C(=O)O]

120 mg of phosphonium salt II"a and 50 mg of furyl propenal were used to synthesize the unsaturated amino acid I"u in 73% yield as a yellow solid —Rf: 0.50 (Ethyl acetate/petroleum ether 3:7+1% acetic acid)-Enantiomeric excess >98%*−[α]$_D$=+236 (c=0.12; CHCl$_3$); $^1$H NMR (300 MHz, CDCl$_3$): δ (ppm)=1.37 (s, 9H, CH$_3$), 2.52-2.68 (m, 2H, CH$_2$), 4.31-4.33 (m, 1H, CHN), 4.99-5.05 (m, 1H, NH), 5.34-5.37 (m, 0.17 H, CH=), 5.57-5.67 (m, 0.83H, CH=cis or trans), 6.10-6.18 (m, 1H, CH=cis or trans), 6.42-6.52 (m, 1H, CH=cis or trans), 6.87-6.90 (m, 2H, CH=cis or trans), 7.06-7.08 (m, 1H, CH=cis or trans), 7.10-7.11 (m, 1H, CH=cis or trans); $^{13}$C NMR (75 MHz, CDCl$_3$): δ (ppm)=28.3 (CH$_3$), 29.7 (CH$_2$), 53.1 (CHN), 80.3 (C(CH$_3$)$_3$) 108.3 (CH=cis or trans), 108.9 (CH=cis or trans), 111.5 (CH=cis or trans), 111.6 (CH=cis or trans), 119.3 (CH=cis or trans), 119.6 (CH=cis or trans), 121.4 (CH=cis or trans), 122.1 (CH=cis or trans), 125.2 (CH=cis or trans) 127.0 (CH=cis or trans), 127.9 (CH=cis or trans), 128.2 (CH=cis or trans) 129.0 (CH=cis or trans), 132.2 (CH=cis or trans), 134.2 (CH=cis or trans), 142.1.2 (CH=cis or trans), 142.3 (CH=cis or trans), 153.0 (COO), 176.2 (COO); Mass exact calculated for $C_{16}H_{20}NO$ [M−H]$^-$: 306.1336. found 306.1338.

*The enantiomeric purity was determined by HPLC after esterification with TMSCHN$_2$ (Lux 5 μm cellulose-2, hexane: iPrOH 95:5, 0.8 mL·min−1, λ=254 nm, 20° C., $t_R$ (cis or trans (S))=14.3 min, $t_R$ (cis or trans (S))=16.9 min, $t_R$ (cis or trans (R))=21.3 min, $t_R$ (cis or trans (R))=29.4 min)

F.3. Wittig Reaction with Ketone

Synthesis of 2-((t-butyloxycarbonylamino)-6,6,6-trifluoro-5-phenylhex-4-enoic acid (II"v)

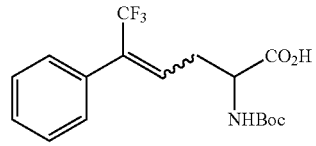 [SMILES: CC(C)(C)OC(=O)NC(CC=C(c1ccccc1)C(F)(F)F)C(=O)O]

120 mg of phosphonium salt (II"a) and 35 mg of trifluoromethylacetophenone were used to afford the unsaturated amino acid I"v as a yellow solid in 81% yield with a cis/trans ratio of 37:63 (81% yield); mp=38-40° C.; Rf: 0.62 (Ethyl acetate/petroleum ether 3:7+1% acetic acid); [α]$_D$=+40.9 (c 0.6, CHCl$_3$); $^1$H NMR (300 MHz, CDCl$_3$): 1.18 (s, 9H, CH$_3$), 2.35-2.38 (m, 0.44H, CH$_2$), 2.0.56 (m, 0.38H, CH$_{27}$), 2.74-2.84 (m, 0.66H, CH$_2$), 2.84-2.99 (m, 0.63H, CH$_2$), 4.17-4.36 (m, 1H, CHN), 5.07 (d, 0.6H, J=6.3 Hz, NH), 5.90 (t, 0.64H, J=7.5 Hz, CH=), 6.28 (t, 0.31H, J=7.5 Hz, CH=),7.08-7.31 (m, 5H, Harom); $^{13}$C NMR (75 MHz, CDCl$_3$) δ 22.7, 28.2, 29.3, 29.7, 31.5, 32, 52.7, 53.0, 80.6, 82.3, 108.7, 125.3 (q, J=276.2 Hz), 125.5 (q, J=10.8 Hz), 128.2, 128.3, 128.4, 128.6, 129, 129.1, 129.6, 131.6, 134.7, 135.1, 135.9, 155.5, 156.6, 174.8, 175.7; FTIR cm$^{-1}$ (neat): 3348, 2965-2918, 1731, 1678, 1587, 1518, 1501, 1432, 1376, 1334, 3319, 1272, 1261, 1244, 1154, 1110, 1080, 1066, 1041, 1018. HRMS (ESI-Orbitrap) Calcd for $C_{17}H_{19}F_3NO_4$ [M−H]$^-$ λ=358.1264. found 358.1261.

G. Optimization of the Synthesis of Phosphonium Salts (II')

Synthesis of Phosphonium Salts Derivatives (II') was Optimized with the Following compounds (a)

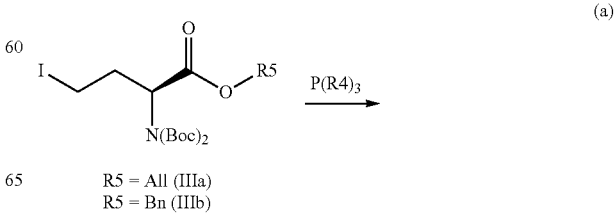

R5 = All (IIIa)
R5 = Bn (IIIb)

-continued

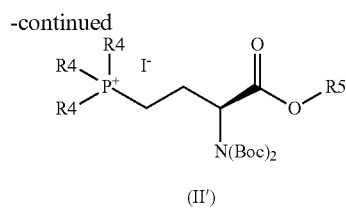

(II')

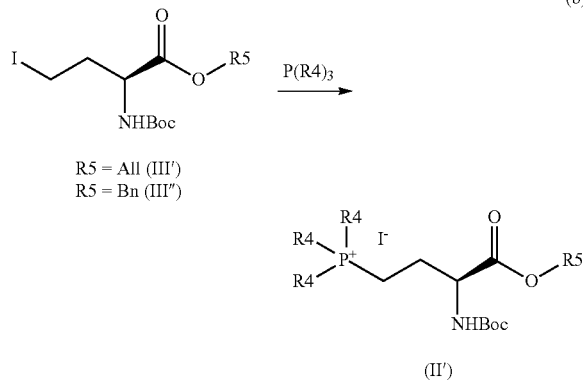

| entry | iodoaminoester R5 | (R4)₃P R4 | Conditions | (II') | yield % |
|---|---|---|---|---|---|
| 1 | All | (IIIa) | cHex | THF/CH₃CN/RT | (II'e) | 79 |
| 2 | All | (IIIa) | Ph | no solvent/2 h/55° C. | (II'f) | 66 |
| 3 | All | (IIIa) | Ph | no solvent/2 h/80° C. | (II'f):1 | 70 (85:15) |
| 4 | All | (III') | Ph | no solvent/2 h/80° C. | (II'a) | 72 |
| 5 | Bn | (III") | Ph | no solvent/2 h/80° C. | (II'g) | 70 |
| 6 | All | (III') | 4-CF₃Ph | no solvent/3 h/80° C. | (II'b) | 39 |

| entry | iodoaminoester R5 | (R4)₃P R4 | Conditions | (II') | yield % |
|---|---|---|---|---|---|
| 7 | All | (III') | 4-MeOPh | THF/2 h/80° C. | (II'c) | 70 |
| 8 | All | (III') | 4-F—Ph | no solvent/24 h/80° C. | (II'd) | 63 |

Thus, tricyclohexylphosphine was quaternized by the iodo amino ester (Ma) in a THF/CH₃CN mixture at room temperature, to afford the phosphonium salt (We) enantiomeric ally pure with 79% yield (Table 2, entry 1). When triphenylphosphine is quaternized with iodo amino ester (Ma), at 50° C. under neat conditions during 2 h, the phosphonium salt (II'f) was obtained in 66% yield (entry 2). When this quaternization is carried out at 80° C., a mixture of mono-N-protected phosphonium salt (II'f) and N,N-diprotected phosphonium salt 1 was obtained, in a ratio 85:15 (entry 3).

When the iodo amino ester mono-N-protected (III') was used to quaternize triphenylphosphine, the corresponding phosphonium salt (II'a) was isolated in 72% yield, after heating 2 h at 80° C. without solvent (entry 4). When the iodo amino ester (III") reacts with triphenylphosphine, the corresponding phosphonium salts (II'g) was obtained with 70% yield (entry 5). In the case of the quaternization of tri-(4-trifluoromethylphenyl)phosphine or the tri-(4-methoxyphenyl)phosphine with iodo amino ester (III'), the corresponding phosphonium salt (II'b) (or II'c) were obtained in 39 and 70% yield, respectively (entries, 6.7). Finally, heating at 80° C. for 24 h iodo derivative (III') reacts with tri-(4-fluorophenyl) phosphine to afford the corresponding phosphonium salt (II'd) in 63% yield (entry 8).

H. Optimization of the Synthesis of Compounds (I') and (I")

H.1.1. Use of Strong Bases

Conditions of the Wittig reaction leading to compounds (I) have been explored in presence of a strong base and benzaldehyde (PhCHO) as aldehyde reactant:

| Entry | Phosphonium salt | Conditions of deprotonation | PhCHO (equiv.) | Conditions of Wittig reaction | Product Yield (%) |
|---|---|---|---|---|---|
| 1 | (II'f) | t-BuLi (3 eq.) −78° −> 0° C./1 h | 0.9 | adding PhCHO at 78° C. then RT° C./16 h | 15 |
| 2 | (II"f) | t-BuLi (3 eq.) −78° −> −55° C./1 h | 1 | adding PhCHO at 78° C. then RT° C./16 h | 26 |
| 3 | (II'a) | t-BuLi (1.9 eq.) −78° −> 0° C./1 h | 0.9 | adding PhCHO at −78° C., then RT° C./2 h | 15 |
| 4 | (II'a) | LDA (3 eq.) −78° −> 0° C./1 h | 0.9 | adding PhCHO at −78° C., then RT° C./2 h | 20 |
| 5 | (II'a) | LiHMDS (3 eq.) −78° −> 0° C./1 h | 0.9 | adding PhCHO at −78° C., hen RT° C./2 h | 30 |
| 6 | (II"a) | t-BuLi (3 eq.) −78° −> −55° C./1 h | 1 | adding PhCHO at 78° C. then RT° C./16 h | 10 |

Deprotonation of the phosphonium salt (III'f) (N(Boc)$_2$) with an excess of t-BuLi at −78° C. then at room temperature, before addition of benzaldehyde at −78° C. and reaction at room temperature, give the corresponding unsaturated amino ester with 15% yield and 80:20 Cis/Trans ratio (Table 3, entry 1). In the case of phosphonium salt (II'a) (NHBoc), deprotonation with t-BuLi, LiHMDS or LDA, in similar conditions, then reaction with benzaldehyde, lead to the corresponding amino ester with yield up to 30% (entries 3-5). In the same conditions, amino acid phosphonium salts (II"f) and (II"a), lead to corresponding γ-δ unsaturated amino acids with respectively 26% and 10% yield (entries 2, 6).

H.1. Use of Weak Bases

As it was possible that the phosphonium salt can serve as phase transfer agent able to activate the Wittig reaction with a weak inorganic base, the reaction with benzaldehyde was studied in these conditions. The results obtained depending on the phosphonium salts, base or phase transfer conditions were presented below:

| Entry | P+ salt | PhCHO (equiv.) | Base (equiv.) | Solvent, conditions | Yield % (% cis:trans) | e.e. (%) |
|---|---|---|---|---|---|---|
| 1 | (II"a) | 1.5 | Cs$_2$CO$_3$ (6 eq.) | EtOH 90° C. overnight | 6 | — |
| 2 | (II"a) | 1.5 | Cs$_2$CO$_3$ (6 eq.) | THF 67° C. overnight | 8 | — |
| 3 | (II"a) | 1.5 | Cs$_2$CO$_3$ (6 eq.) | DMF 90° C. overnight | 33 | — |
| 4 | (II"a) | 1.5 | Cs$_2$CO$_3$ (6 eq.) | PhCl 90° C. 48 h | 65 | 99 |
| 5 | (II"a) | 1.5 | Li$_3$PO$_4$ (6 eq.) | PhCl 90° C. overnight | 6 | — |
| 6 | (II"a) | 1.5 | NaH (3 eq.) | PhCl 90° C. overnight | 5 | — |
| 7 | (II"a) | 1.5 | NEt$_3$ (3 eq.) | PhCl 90° C. overnight | 0 | — |
| 8 | (II"a) | 1.5 | K$_3$PO$_4$ (6 eq.) | PhCl 90° C. overnight | 70 (30:70) | >99 |
| 9 | (II"a) | 1.2 | K$_2$CO$_3$ (1.2 eq.) | 0.8 eq. H$_2$O/ MeOH 65° C. overnight | 7 | — |
| 10 | (II"a) | 1.2 | K$_2$CO$_3$ (1.2 eq.) | 0.8 eq. H$_2$O/ dioxane 90° C. overnight | 58 | >99 |
| 11 | (II"a) | 1.2 | K$_3$PO$_4$ (6 eq.) | 0.8 eq. H$_2$O/ MeOH 90° C. overnight | 48 (20:80) | >99 |
| 12 | (II"a) | 1.2 | K$_3$PO$_4$ (6 eq.) | dioxane 90° C. overnight | 72 (30:70) | >99 |
| 13 | (II"f) | 1 | Cs$_2$CO$_3$ (5 eq.) | PhCl/50° C. overnight | 60 | >99 |
| 14 | (II"f) | 1.5 | Cs$_2$CO$_3$ (2 eq.) | PhCl/50° C. overnight | 87 | >99 |
| 15 | (II'a) | 1.5 | Cs$_2$CO$_3$ (6 eq.) | PhCl/50° C. overnight | 86 (12:88) | 83 |
| 16 | (II'a) | 1.5 | Cs$_2$CO$_3$ (6 eq.) | PhCl/40° C. overnight | 39 | 88 |
| 17 | (II'a) | 1.5 | Cs$_2$CO$_3$ (6 eq.) | PhCl/RT ° C. H$_2$O (1 eq.)/ 3 h 30 | 90 | 83 |

When the amino acid phosphonium salt (II"a) is heated overnight in ethyl alcohol (or THF) with the benzaldehyde (1.5 equiv.) in presence of 6 equivalents of Cs$_2$CO$_3$ γ-β unsaturated aminoacids are obtained with low yields (<8%, entries 1, 2). If the reaction is performed with Cs$_2$CO$_3$ in DMF or chlorobenzene at 90° C., γ-δ unsaturated amino acids are obtained respectively with 33% and 65% yield (entries 3, 4). The use of Li$_3$PO$_4$, NaH or triethylamine (weak organic base) in chlorobenzene at 90° C., did not lead to the formation of the product (entries 5-7). Better results were achieved when the amino acid phosphonium salt (II"a) is heated overnight in chlorobenzene with benzaldehyde in presence of 6 equivalents of K$_3$PO$_4$ (entry 8). γ-δ unsaturated amino acid is then isolated with 70% yield in a 70:30 trans/cis ratio. HPLC analysis on chiral column of the corresponding methyl ester derivative shows that the γ-βunsaturated amino acids are obtained enantiomerically pure in these conditions (entry 8). Similarly, when the reaction is performed with K$_3$PO$_4$ in dioxane at 90° C., the expected compound is isolated in 72% yield (70:30 trans:cis ratio) with ee >99% (entry 12).

When using K$_2$CO$_3$ as base in presence of a trace of water, using methanol as solvent provides low yields (7%, entry 9). However, when using K$_2$CO$_3$ as base in presence of a trace of water in dioxane as solvent a yield of 58% is obtained (entry 10). When using K$_3$PO$_4$ in place of K$_2$CO$_3$ in dioxane, comparable yields were obtained (48%, entry 11).

In the case of amino acid phosphonium salt (II"f) (N,N (Boc)$_2$), the heating with benzaldehyde (1 equiv.) overnight in chlorobenzene at 50° C. in presence of 5 equivalent of Cs$_2$CO$_3$, give γ-δ unsaturated amino acids enantiomerically pure with 60% yield (entry 13). If this reaction was performed in the same conditions of solvent and temperature, but in presence of 1.5 and 2 equivalents of benzaldehyde and Cs$_2$CO$_3$ respectively, the amino acid is obtained with 87% yield (entry 14).

In the phase transfer conditions, amino ester phosphonium salt (II'a) reacts also with benzaldehyde to give the corresponding γ-δ unsaturated amino ester (entries 15-17). After heating overnight in chlorobenzene at 50° C. in presence of 6 equivalent of Cs$_2$CO$_3$, the product is obtained with 86% yield as a trans/cis mixture in 88:12 ratio (entry 15). HPLC analysis on chiral column shows that in these conditions, γ-δ unsaturated amino ester is obtained with 83% e.e. (entry 15). When the reaction was performed at 40° C., the yield obtained for the product decreases to 39% whereas enantiomeric excess increases to 88% (entry 16).

When the aminoester phosphonium salt (II'a) reacts with benzaldehyde in chlorobenzene in presence of one equivalent of water, γ-δ unsaturated amino ester is obtained after 3 h30 in 90% yield and with 83% of enantiomeric excess (entry 17). The partial racemization (83-88% e.e.) observed in the case of the use of amino ester phosphonium salt, can be explained again by a deprotonation in a position of the ester (reagents or procucts), in basic conditions.

I. Application of Compounds (I)

1.1. Complexation: (S)-2-(t-butyloxycarbonylamino)-7-phenylhept-4,6-dienoate methyl ferricarbonyl The diene derivatives (I"o) was used for the preparation of a new amino acid pentacarbonyl iron complexe:

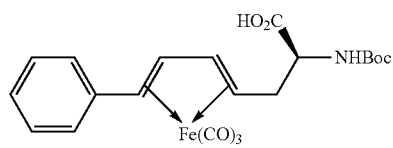

A solution of 62 mg of aminoester (I"o) (0.19 mmol) in 2 mL of dry di-n-butyl ether, were introduced 0.11 mL of Fe(CO)$_5$ (0.85 mol, 4.5 eq). The reaction mixture was heated at 130° C., during 16 h under argon, and evaporated under vacuum. The crude product was purified by chromatography on neutral alumina with ethyl acetate/petroleum ether (1:4) as eluent to afford (S)-2-(t-butyloxycarbonylamino)-7-phenyl-hept-4,6-dienoate methyl ferricarbonyl in 42% yield. Orange oil —R$_f$: 0.39 (Ethyl acetate/petroleum ether 1:4). [α]$_D$=+23 (c=0.3; CHCl$_3$). IR (cm$^{-1}$): 3499 (N—H), 3028-2927 (C—H), 2363, 2143 (CO), 2041 (CO), 1749 (C=O), 1715 (C=O), 1689, 1625, 1599, 1577, 1528, 1493, 1448, 1437, 1348, 1312, 1252, 1212, 1168, 1155, 1119, 1071, 1040, 1012, 989, 947, 912, 861, 794, 757, 732, 694, 622, 609, 559, 540. $^1$H NMR (300 MHz, CDCl$_3$): δ (ppm)=1.44-1.49 (4s, 9H, CH$_3$), 2.08-2.12 (2m, 1H, CH$_2$), 2.60-2.90 (4m, 1H, CH$_2$), 3.75-3.83 (4s, 3H, OCH$_3$), 4.40-4.56 (2m, 1H, CHN), 5.08-5.22 (2m, 1H, NH), 5.44 (dd, 1H, J=4.2, 5.1 Hz, CH=), 5.67-5.79 (2m, 1H, CH=), 6.28-6.37 (m, 1H, CH=), 6.55 (2d, 1H, J=8.1 Hz, J=7.8 Hz, CH=), 6.80 (2dd, J=2.7, 5.1 Hz, J=1.8, 5.7 Hz, CH=), 7.18-7.48 (m, 5H, Harom). $^{13}$C NMR (75 MHz, CDCl$_3$): δ(ppm)=28.3 (CH$_3$), 30.1 (CH$_2$), 30.9 (CH$_2$), 52.4 (CHN), 52.5 (CHN), 123.5 (CH=ou Carom), 123.9 (CH=ou Carom), 125.0 (CH=ou Carom), 126.1 (Carom), 126.3 (Carom), 126.5 (Carom), 127.5 (Carom), 127.8 (Carom), 128.6 (Carom), 132.7 (Carom), 134.5 (CH=ou Carom), 137.2 (Carom). Mass exact calculated or C$_{22}$H$_{25}$Fe$_1$N$_1$Na$_1$O$_7$ [M+Na]$^+$: 494.0873. found 494.0843.

1.2. Use of (I″k) in Suzuki-Miyaura Coupling

The boronato amino acid (I″k) may be used as reactant in Suzuki-Miyaura coupling:

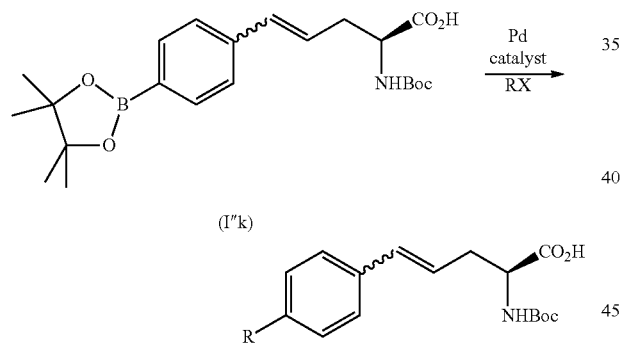

(I″k)

1.3. Use of (I″k) to Synthesize Trifluoroborate Derivatives

The boronato amino acid (I″k) may be reacted with fluoride ions to give trifluoroborate derivatives that may be used in IRM or PET medical imaging:

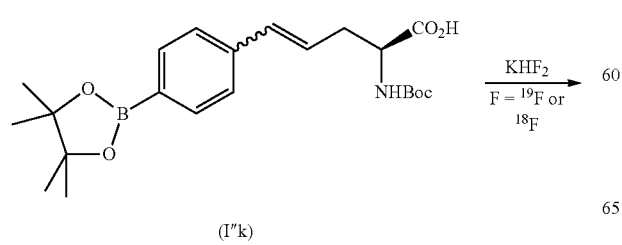

(I″k)

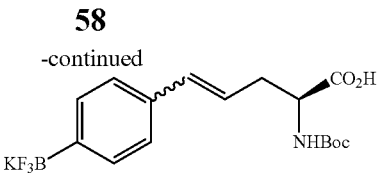

1.4. Use of (I″p) in Click Chemistry

The azido amino acid (I″p) may be used for drafting functionalized aklynes by click chemistry:

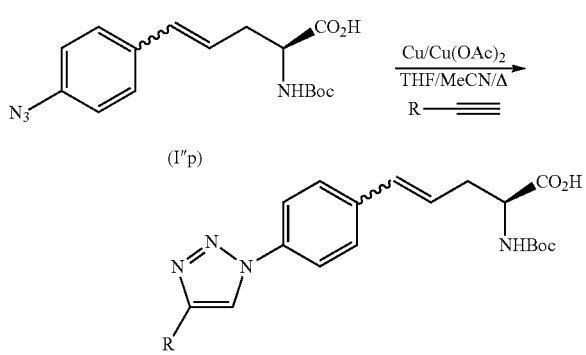

The invention claimed is:
1. A process for producing a compound of formula (I),

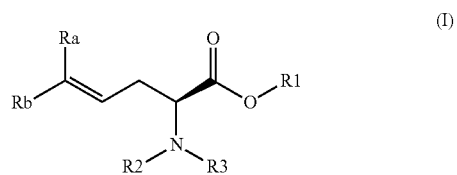

comprising performing a Wittig reaction by reacting a phosphonium salt of general formula (II)

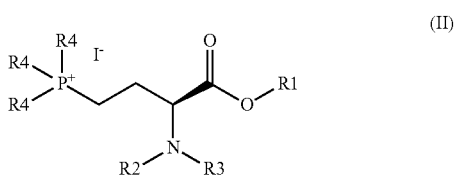

wherein
R1 represents a hydrogen atom or R5, wherein R5 is a substituted or unsubstituted group selected from the group consisting of alkyl, cycloalkyl, aryl, and alkenyl,
R2 and R3 may be the same or different and each represents a hydrogen atom or a substituted or unsubstituted group selected from the group consisting of alkyl, cycloalkyl, aryl, alkenyl, and —COR, wherein R is a substituted or unsubstituted group selected from the group consisting of alkyl, cycloalkyl, aryl, alkenyl, alkyloxy, cycloalkyloxy, and aryloxy, and
R4 represents a substituted or unsubstituted group selected from the group consisting of alkyl, cycloalkyl, aryl, and alkenyl;

with compound (IV), wherein compound (IV) is selected from the group consisting of a ketone or aldehyde of formula RaCORb, an imine of formula RaRbC=NRc, a [Ra, Rb]-trisubstituted trioxane, and a RaRbC(OH)(SO$_3$Na), wherein Ra and Rb may be the same or different and each represents a hydrogen atom or a substituted or unsubstituted group selected from the group consisting of alkyl, alkenyl, cycloalkyl, aryl, metallocenyl and —COR, wherein R is a substituted or unsubstituted group selected from the group consisting of alkyl, cycloalkyl, aryl, alkenyl, alkyloxy, cycloalkyloxy and aryloxy, and wherein Rc represents a hydrogen atom, a substituted or unsubstituted group selected from the group consisting of alkyl, cycloalkyl, and aryl or an electro-attractive group;

in the presence of a weak base selected from the group consisting of Cs$_2$CO$_3$, Li$_3$PO$_4$, NaH, K$_3$PO$_4$ and K$_2$CO$_3$, and a solvent suitable for phase transition conditions selected from the group consiting of chlorobenzene, dichloromethane, chloroform, dichlorobenzene, dichloroethane, and dixoane, resulting in said compound of formula (I).

2. The process according to claim 1, for producing a compound of formula (I'),

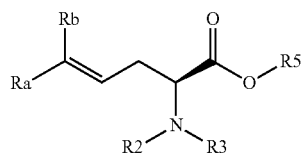
(I')

comprising:

(a) quaternization of a phospine P(R4)$_3$ with an iodo derivative of general formula (III)

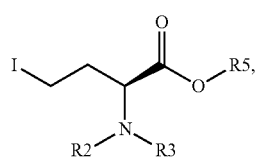
(III)

wherein Ra, Rb, R2, R3, R4 and R5 are as defined in claim 1, resulting in the phosphonium salt of formula (II')

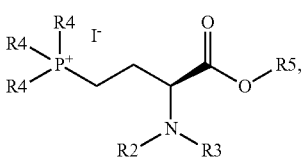
(II')

and (b) performing the Wittig reaction by reacting the phosphonium salt of formula (II') with the compound (IV).

3. The process according to claim 1, for producing a compound of formula (I"),

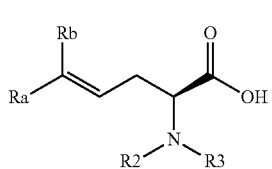
(I")

comprising:

a) quaternization of a phosphine P(R4)$_3$ with an iodo derivative of general formula (III)

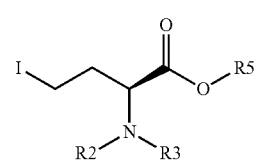
(III)

wherein Ra, Rb, R2, R3, R4 and R5 are as defined in claim 1, resulting in a phosphonium salt of formula (II')

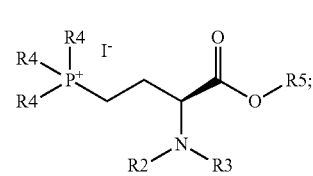
(II')

b) deprotecting the carboxylic acid function of said phosphonium salt (II'), resulting in the corresponding phosphonium salt of formula (II")

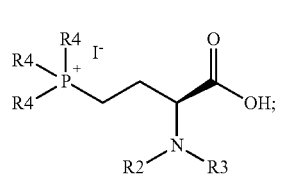
(II")

and (c) performing the Wittig reaction by reacting the phosphonium salt of formula (II") with the compound (IV).

4. The process according to claim 1, wherein R2 is a hydrogen atom, R3 is a Boc group, R4 is phenyl and R5 is allyl.

5. The process according to claim 1, wherein the weak base is one or more of K$_3$PO$_4$, Cs$_2$CO$_3$ or K$_2$CO$_3$.

6. The process according to claim 1, wherein R1 is selected from the group consisting of hydrogen atom, allyl group and benzyl group.

7. The process according to claim 1, wherein R2 is a hydrogen atom or Boc and R3 is Boc.

8. The process according to claim 1, wherein the phosphine P(R4)$_3$ is selected from the group consisting of tricyclohexylphosphine, triphenylphosphine, trifurylphosphine, tri(4-methoxyphenyl)phosphine, tri(4-trifluoromethylphenyl)phosphine, tri(4-fluorophenylphosphine) and tri(4-chlorophenyl)phosphine.

9. The process according to claim 1, wherein RaCORb is selected from the group consisting of benzaldehyde, 4-trifluoromethylbenzaldehyde, 4-nitrobenzaldehyde, 4-cyanobenzaldehyde, 4-methoxybenzaldehyde, 3,4-dimethoxybenzaldehyde, 2-furaldehyde, 3-phenylpropanal, paraformaldehyde, phenylacetaldehyde, 4-(4,4,5,5-tetramethyl-1,3,2dioxaborolan-2-yl)benzaldehyde, aldehyde derived from calix-[4]-arene, ferrocene-carboxaldehyde, m-phthaldialdehyde, transcinnamaldehyde, (E)-4-azidophenylprop-2-enal, 4-oxo-2-butenoate, 3-methylbutenal, 4-nitro-trans-cinnamaldehyde, thiophene propenal, furyl propenal, and trifluoromethylacetophenone.

10. The process according to claim 3, wherein R5 is an allyl group and wherein deprotecting the carboxylic acid function of compound (II') is performed in presence of $Pd_2(dba)_3$, dppe and $HNEt_2$ at room temperature.

11. A process for manufacturing an iodo derivative (III) of general formula (III')

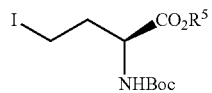

wherein R5 is a substituted or unsubstituted group selected from the group consisting of alkyl, cycloalkyl, aryl, and alkenyl,
comprising:
protecting the acid function of the lateral chain of L aspartic acid by transformation into monoester by esterification with methanol;
protecting the amino function with a Boc group;
protecting the remaining acid function by esterification in the presence of the bromide derivative R5-Br to lead to the corresponding diester;
further protecting the amino function with a second Boc group;
reducing the terminal ester in aldehyde using DIBAL;
further reducing the aldehyde group with $NaBH_4$ to lead to the N,O protected homoserine derivative;
reacting with iodine in the presence of triphenylphosphine and imidazole at room temperature to lead to the N-diprotected aminoester;
reacting with NaI in presence of $CeCl_3$ at room temperature and further hydrolysing to obtain the N-monoprotected compound of formula (III').

12. A compound of general formula (I)

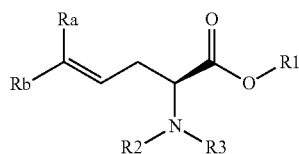

wherein
Ra and Rb may be the same or different and each represents a hydrogen atom or a substituted or unsubstituted group selected from the group consisting of alkyl, alkenyl, cycloalkyl, aryl, metallocenyl and —COR, wherein R is a substituted or unsubstituted group selected from the group consisting of alkyl, cycloalkyl, aryl, alkenyl, alkyloxy, cycloalkyloxy and aryloxy;
R1 represents a hydrogen atom;
R2 and R3 may be the same or different and represent each a hydrogen atom or a substituted or unsubstituted group selected from the group consisting of alkyl, cycloalkyl, aryl, alkenyl, and —COR, wherein R is a substituted or unsubstituted group selected from the group consisting of alkyl, cycloalkyl, aryl, alkenyl, alkyloxy, cycloalkyloxy, and aryloxy;
provided that when Ra is an aryl group or a group comprising an aryl substituent, Rb is not an aryl group or a group comprising an aryl substituent;
provided that when Ra is a unsubstitued or alkyl-substituted α, ω-alkylene having from 0 to 3 carbon atoms substituted by a phosphino, phosphonyl or phosphono group, Rb is not selected from the group consisting of hydrogen, alkyl, haloalkyl, hydroxyalkyl, alkoxyalkyl, arylalkyl, akenyl and aryl;
provoided that when R1{R2, R3} is {H, H}, then {Ra, Rb} is not {H, H}; and
provided that when {R2, R3} is {Troc, H} or {H, Troc}, then {Ra, Rb} is not {H, —CH=CH—CH(ME)$_2$ } or {—CH=CH—CH(Me)$_2$, H}.

13. A compound of general formula (II)

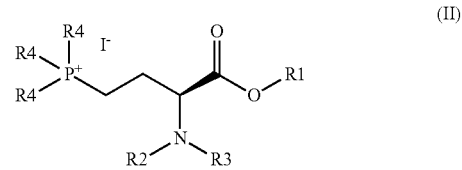

wherein
R1 represents a hydrogen atom or R5, wherein R5 is a substituted or unsubstituted group selected from the group consisting of alkyl, cycloalkyl, aryl, and alkenyl;
R2 and R3 may be the same or different and each represents a hydrogen atom or a substituted or unsubstituted group selected from the group consisting of alkyl, cycloalkyl, aryl, alkenyl, and —COR, wherein R is a substituted or unsubstituted group selected from the group consisting of alkyl, cycloalkyl, aryl, alkenyl, alkyloxy, cycloalkyloxy, and aryloxy; and
R4 represents a substituted or unsubstituted group selected from the group consisting of alkyl, cycloalkyl, aryl, and alkenyl.

14. A compound of general formula (III)

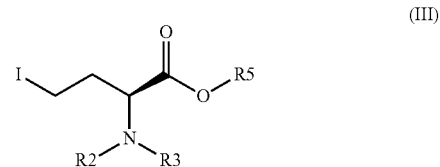

wherein
R2 and R3 may be the same or different and each represents a hydrogen atom or a substituted or unsubstituted group selected from the group consisting of alkyl, cycloalkyl, aryl, alkenyl, and —COR, wherein R is a substituted or unsubstituted group selected from the group consisting of alkyl, cycloalkyl, aryl, alkenyl, alkyloxy, cycloalkyloxy, and aryloxy;
R5 represents a substituted or unsubstituted group selected from the group consisting of alkyl, cycloalkyl, aryl, and alkenyl;

provided that when R5 is methyl, R2 and R3 are not both Boc groups;

provided that when R5 is benzyl, {R2, R3} is not {H, Boc} or {Boc, H};

provided that when R5 is ethyl, {R2, R3} is not {H,C(=O)—O—CH$_2$-Ph} or {C(=O)—O—CH$_2$-Ph,H}.

15. A library of two or more compounds of formula (I) according to claim 12.

* * * * *